US010906169B1

(12) United States Patent
Bashir et al.

(10) Patent No.: US 10,906,169 B1
(45) Date of Patent: Feb. 2, 2021

(54) MUSCLE-POWERED BIOLOGICAL MACHINES

(71) Applicant: The Board of Trustees of the University of Illinois, Urbana, IL (US)

(72) Inventors: Rashid Bashir, Champaign, IL (US); Ritu Raman, Champaign, IL (US); Caroline Cvetkovic, Darien, IL (US)

(73) Assignee: BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 340 days.

(21) Appl. No.: 15/793,300

(22) Filed: Oct. 25, 2017

Related U.S. Application Data

(60) Provisional application No. 62/412,884, filed on Oct. 26, 2016, provisional application No. 62/455,882, filed on Feb. 7, 2017.

(51) Int. Cl.
| | | |
|---|---|---|
| *G01N 33/50* | (2006.01) | |
| *B25J 9/00* | (2006.01) | |
| *A61L 27/38* | (2006.01) | |
| *B25J 9/16* | (2006.01) | |
| *A61F 2/08* | (2006.01) | |
| *C12N 5/00* | (2006.01) | |
| *C12N 5/071* | (2010.01) | |
| *C12N 5/077* | (2010.01) | |
| *C12N 5/0793* | (2010.01) | |
| *G03F 7/00* | (2006.01) | |
| *C12N 13/00* | (2006.01) | |
| *A61L 27/52* | (2006.01) | |
| *A61F 2/02* | (2006.01) | |
| *A61N 1/36* | (2006.01) | |
| *A61N 5/06* | (2006.01) | |

(52) U.S. Cl.
CPC .............. *B25J 9/0009* (2013.01); *A61F 2/08* (2013.01); *A61L 27/383* (2013.01); *A61L 27/3826* (2013.01); *A61L 27/3891* (2013.01); *A61L 27/3895* (2013.01); *A61L 27/52* (2013.01); *B25J 9/1615* (2013.01); *C12N 5/0062* (2013.01); *C12N 5/0619* (2013.01); *C12N 5/0658* (2013.01); *C12N 5/0697* (2013.01); *C12N 13/00* (2013.01); *G01N 33/5061* (2013.01); *G01N 33/5088* (2013.01); *G03F 7/0037* (2013.01); *A61F 2/022* (2013.01); *A61F 2002/0894* (2013.01); *A61F 2210/0076* (2013.01); *A61N 1/36003* (2013.01); *A61N 5/0622* (2013.01); *C12N 2503/02* (2013.01); *C12N 2503/04* (2013.01); *C12N 2506/02* (2013.01); *C12N 2506/1323* (2013.01); *C12N 2513/00* (2013.01)

(58) Field of Classification Search
CPC .................................. B25J 9/0009; A61F 2/08
See application file for complete search history.

(56) References Cited

U.S. PATENT DOCUMENTS

| 6,488,872 B1 | 12/2002 | Beebe |
|---|---|---|
| 2002/0022884 A1 | 2/2002 | Mansmann |
| 2007/0141647 A1 | 6/2007 | Park |

OTHER PUBLICATIONS

Yamamoto et al., Functional evaluation of artificial skeletal muscle tissue constructs fabricated by a magnetic force-based tissue engineering technique, Tissue Engineering part A, vol. 17, p. 107-113. (Year: 2011).*
Morimoto et al., Three-dimensional neuron-muscle constructs with neuromuscular junctions, Biomaterials, vol. 34, p. 9413-9419. (Year: 2013).*
Melchels et al., "A review on stereolithography and its applications in biomedical engineering" Biomaterials, 31:6121-30 (2010).
Raman et al., "Sterolithographic 3D Bioprinting for Biomedical Applications", Essentials of 3D Biofabrication and Translation, 89-121 (2015).
Raman et al., "High-Resolution Projection Microstereolithography for Patterning of Neovasculature", Adv. Healthc. Mater. 1-10 (2015).
Sears, "A Review of Three-Dimensional Printing in Tissue Engineering", Tissue Eng. Part B, 22(4):298-310 (2016).
Peltola et al., "A review of rapid prototyping techniques for tissue engineering purposes", Ann. Med. 40, 268-280 (2008).
Bajaj et al., "3D Biofabrication Strategies for Tissue Engineering and Regenerative Medicine", Annu. Rev. Biomed. Eng. 16:247-276 (2013).
Kamm et al., "Creating Living Cellular Machines", Ann. Biomed. Eng., 42:445-459 (2014).
Feinberg "Biological Soft Robotics", Annu. Rev. Biomed. Eng., 17:243-65 (2015).
Chan et al., "Utilization and control of bioactuators across multiple length scales", Lab Chip, 14:653-670 (2014).
Sambasivan et al., "Adult Skeletal Muscle Stem Cells", Vertebrate Myogenesis, 56:191-213 (2015).
Duffy et al., "Engineered skeletal muscle tissue for soft robotics: fabrication strategies, current applications, and future challenges" Nanomed. Nanobiotechnol, 6:178-195 (2014).
Bian et al., "Mesoscopic hydrogel molding to control the 3D geometry of bioartificial muscle tissues", Nat. Protoc. 4:1522-34 (2009).
Cvetkovic et al. "Three-dimensionally printed biological machines powered by skeletal muscle", Proc. Natl. Acad. Sci., 111(28):10125-30 (2014).

(Continued)

*Primary Examiner* — Taeyoon Kim
*Assistant Examiner* — Tiffany M Gough
(74) *Attorney, Agent, or Firm* — DLA Piper LLP US

(57) ABSTRACT

The present disclosure provides a biological machine comprising a skeleton comprising at least one hydrogel strip and at least two hydrogel bases, and at least one bioactuator, the at least one bioactuator comprising at least one muscle ring, the muscle ring comprising skeletal muscle cells, wherein the muscle ring is tethered around the at least two pillars. The muscle ring can comprises skeletal muscle, and skeletal muscle innervated with motor neurons, allowing chemical control of muscle contraction. Methods of making the biological machine is also provided.

15 Claims, 19 Drawing Sheets
(19 of 19 Drawing Sheet(s) Filed in Color)

(56) References Cited

OTHER PUBLICATIONS

Raman et al. "Optogenetic skeletal muscle-powered adaptive biological machines", Proc. Natl. Acad. Sci., 113(13):3497-3502 (2016).
Feinberg et al. "Muscular thin films for building actuators and powering devices", Science, 317:1366-70 (2007).
Nawroth et al. "A tissue-engineered jellyfish with biomimetic propulsion", Nat. Biotechnol., 30:792-7 (2012).
Chan et al., "Multi-material bio-fabrication of hydrogel cantilevers and actuators with stereolithography", Lab Chip, 12:88-98 (2012).
Chan et al. "Development of miniaturized walking biological machines", Sci. Rep., 2:857 (2012).
Park et al., "Phototactic guidance of a tissue-engineered soft-robotic ray", Science, 353:158-162 (2016).
Bian et al., "Engineered skeletal muscle tissue networks with controllable architecture", Biomaterials, 30:1401-12 (2009).
Hinds et al., "The role of extracellular matrix composition in structure and function of bioengineered skeletal muscle", Biomaterials, 32:3575-83 (2011).
Sakar et al., "Formation and optogenetic control of engineered 3D skeletal muscle bioactuators", Lab Chip, 12(23):4976-85 (2012).
Rangarajan et al., "Use of Flow, Electrical, and Mechanical Stimulation to Promote Engineering of Striated Muscles", Ann. Biomed. Eng., 42(7):1391-1405 (2014).
Dennis et al., Excitability and contractility of skeletal muscle engineered from primary cultures and cell lines. Am. J. Physiol. Cell Physiol., 280:C288-C295 (2001).
Herr et al., "A swimming robot actuated by living muscle tissue", J. Neuroeng. Rehabil., 1-9 (2004).
Kaur et al., "Cell lines: Valuable tools or useless artifacts", Spermatogenesis, 2(1):1-5 (2012).
Chan et al., "Three-dimensional photopatterning of hydrogels using stereolithography for long-term cell encapsulation", Lab Chip, 10:2062-70 (2010).
Neiman et al., "Photopatterning of hydrogel scaffolds coupled to filter materials using stereolithography for perfused 3D culture of hepatocytes", Biotechnol. Bioeng., 112(4):777-787 (2015).
Raman et al., "3D printing enables separation of orthogonal functions within a hydrogel particle", Biomed. Microdevices 18, 49 (2016).
Novosel et al., "Vascularization is the key challenge in tissue engineering", Adv. Drug Deliv. Rev., 63:300-11 (2011).
Barolet, "Light-Emitting Diodes (LEDs) in Dermatology", Semin. Cutan. Med. Surg., 27:227-238 (2008).
Moreira et al., "Application of high brightness LEDs in the human tissue and its therapeutic response", Applied Biomedical Engineering (eds. Gargiulo, G.D. & McEwan, A.) Ch. 1 (InTech) 3-20 (2011).
Donnelly et al., "A novel bioreactor for stimulating skeletal muscle in vitro", Tissue Eng. Part C. Methods, 16:711-718 (2010).
Powell et al., "Mechanical stimulation improves tissue-engineered human skeletal muscle", Am. J. Physiol. Cell Physiol., 283:C1557-65 (2002).
Uzel et al. "Microfluidic device for the formation of optically excitable, three-dimensional, compartmentalized motor units", Sci. Adv., 2:1-13 (2016).
Duan et al., "Insulin-like growth factors (IGFs), IGF receptors, and IGF-binding proteins: roles in skeletal muscle growth and differentiation",. Gen. Comp. Endocrinol., 167:344-51 (2010).

* cited by examiner

| Exercise Training Regimen Combining Mechanical and Optical Stimulation |||
|---|---|---|
| Day | Static Mechanical Stimulation | Dynamic Optical Stimulation |
| 1-3 | Bio-Bot tethered to underlying glass slide | No Optical Stimulation |
| 4-12 | Bio-Bot tethered to underlying glass slide | 490 nm pulse stimulation at 1.9 mW mm$^{-2}$ — Daily Stimulation Regimen: 1 Hz (5 min), Rest (2 min), 2 Hz (5 min), Rest (2 min), 4 Hz (5 min) |

FIG. 10

MUSCLE-POWERED BIOLOGICAL MACHINES

PRIORITY

This application claims the benefit of U.S. Ser. No. 62/412,884, filed on Oct. 26, 2016, and U.S. Ser. No. 62/455,882, filed on Feb. 7, 2017, both of which are incorporated herein by reference in their entireties.

STATEMENT REGARDING FEDERALLY SPONSORED RESEARCH OR DEVELOPMENT

This invention was made with government support under CBET-0939511 and DGE-1144245 awarded by the National Science Foundation. The government has certain rights in the invention.

BACKGROUND

Biological materials have the ability to sense, process, and respond to a range of dynamic environmental signals in real-time. This capability allows biological systems to demonstrate complex behaviors such as self-assembly, self-organization, self-healing, self-replication, and constant adaptation of composition and functionality to best suit their environment. Recent advances in manufacturing technologies, such as 3D printing, combined with progress in the field of biomaterials, have synergistically produced robust approaches for manufacturing complex 3D structures from biological materials[1-3]. This has driven fundamental advances in the fields of tissue engineering and regenerative medicine by providing a method of reverse engineering native tissues and organs[4-6].

Thus far, use of these technologies has primarily been limited to replicating biological structures found in nature while largely neglecting applications in forward engineered biological systems capable of non-natural functional behaviors. Bio-integrated robots, or bio-bots, built using a combination of biological and synthetic materials have the potential to develop enhanced functional attributes as compared to robots made with traditional synthetic materials alone[7,8]. The dynamically adaptive nature of biological materials makes them ideal candidates for serving as the building blocks of "smart" responsive machines and systems for a variety of applications.

Nearly all machines require actuators, modules that convert energy into motion, to produce a measurable output in response to varied input stimuli[9]. Skeletal muscle is a natural actuator, capable of generating larger forces from more compact structures than actuators made from synthetic materials, and designed to be modular and adaptive to changing environmental loads[10-12].

The first demonstrations of bio-integrated machines, composed of synthetic skeletons coupled to biological actuators, employed the autonomous contraction of engineered cardiac muscle as a source of power[15-19]. The continuous beating of cardiac muscle does not provide "on-off" control over such machines, motivating the development herein of bio-integrated machines powered by skeletal muscle. Until now, bio-integrated machines suited to applications that required force production at the millimeter- to centimeter-scale have not been described.

BRIEF SUMMARY

Embodiments provide biological machines. The biological machines can comprise a skeleton comprising two or more hydrogel pillars having top and bottom base end surfaces, wherein the two or more hydrogel pillars are coupled to one or more hydrogel beams at their top base end surfaces, wherein the hydrogel beam extends between the two or more hydrogel pillars; and at least one layered tissue ring comprising a first ring shaped layer comprising differentiated myoblasts in a gel; and a second ring shaped layer comprising motor neurons; wherein the first and second layers are fused into a layered tissue ring. The layered tissue ring can surround the two or more pillars. The two or more hydrogel pillars can have caps on their bottom base end surfaces. The differentiated myoblasts can be elongated, contractile myotubes. Biological machines can achieve active force generation of about 150, 200, 300 or more μN or about 0.3, 0.4, 0.5 or more kPa and can be capable of locomotion. The one or more layered tissue rings can have motor neuron induced muscle contraction. The layered tissue rings can contract in response to electrical stimulation, chemical stimulation, optical stimulation, or combinations thereof. The integrated motor neurons can be responsive to at least one excitatory neurotransmitter such as glutamate. The layered tissue ring can comprise neuromuscular junctions. The one or more of the cells of the layered tissue ring can express one or more heterologous light-sensitive proteins.

An embodiment of provides layered tissue rings. A layered tissue ring can comprise a first ring shaped layer comprising differentiated myoblasts in a gel; and a second ring shaped layer comprising motor neurons in a gel, wherein the first and second layers are fused into a layered tissue ring. The differentiated myoblasts can be skeletal muscle cells. The layered tissue ring can have motor neuron induced muscle contraction and can comprise neuromuscular junctions. One or more of the cells of the layered tissue ring can express one or more heterologous light-sensitive proteins.

Another embodiment provides a mold containing a layered tissue ring. It comprises a mold in the shape of a ring and, within the mold, a layered tissue ring comprising a first ring shaped layer comprising differentiated myoblasts in a gel; and a second ring shaped layer comprising motor neurons in a gel; wherein the first and second layers are fused into a layered tissue ring, and wherein the layered tissue ring is compacted into the mold.

Still another embodiment provides methods of making layered tissue rings. The methods comprise adding myoblasts and a gel solution to a ring mold and allowing the myoblasts to differentiate into mature muscle fibers. Embryoid bodies and a gel solution are added to the ring mold. The embryoid bodies are allowed to differentiate into motor neurons, such that a layered tissue ring is formed.

Yet another embodiment provides methods of making biological machines. The methods comprise making two or more hydrogel pillars coupled to one or more hydrogel beams with a stereo-lithographic apparatus or a molding apparatus and polymerizable liquid materials, making a layered tissue ring, and surrounding the two or more pillars with the layered tissue ring.

An embodiment provides methods of inducing biological machines to locomote. The methods comprise contacting a portion of a layered tissue ring or the entire layered tissue ring with light, electrical pulses, or a chemical capable of inducing contraction of the layered tissue ring such that the biological machine locomotes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings, wherein:

FIG. 10. Muscle ring exercise training regimen. Protocol for stimulating bio-bots using a static mechanical stimulus (imposed by tethering the bio-bot to an underlying glass coverslip) starting Day 1, immediately after ring transfer, and a dynamic optical stimulus starting Day 4, after transferring the bio-bots to differentiation medium).

through the formation of embryoid bodies (EBs) (c-d), and then combined with the engineered muscle tissue and ECM proteins (e) on 3D printed hydrogel devices (f-g). Scale bars, 50 μm (b and d), 500 μm (c), and 10 μm (d, inset).

Figure 12:
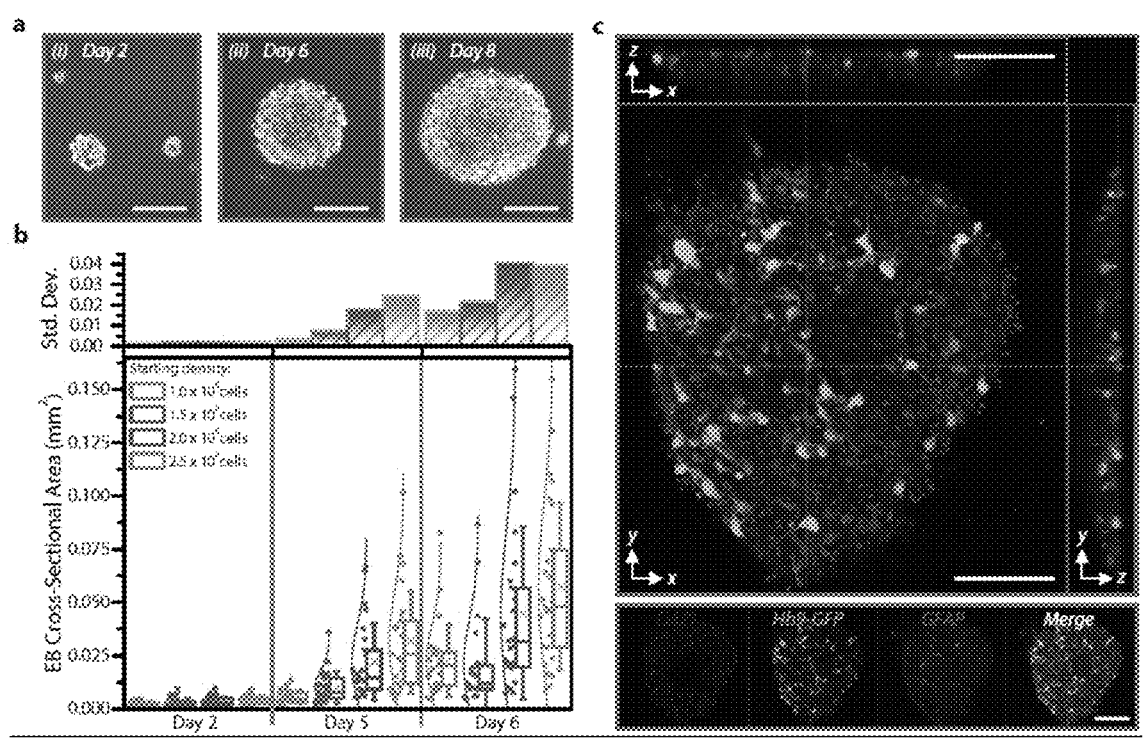

FIG. 12 panels a-c. (a) EBs aggregated more cells, grew in diameter, and became more spherical over time (shown at (i) day 2, (ii) day 6, and (iii) day 8 of differentiation). (b) Embryoid bodies (EBs) increased in size over a week of differentiation. The starting cell density of HBG3 mESCs influenced the size of mature EBs, with a larger initial density resulting in larger average cross-sectional area, as well as a larger range (standard deviation) of diameters of resulting EBs. Box plots represent $25^{th}$, $50^{th}$, and $75^{th}$ percentiles, with average values marked as (x) and whiskers representing ±standard deviations. Data are presented (along with normal distribution curves) to the left of the boxes (n=20-25 EBs per density and time point). (c) Confocal images (xy, large box; xz; yz) of an EB (day 8 of differentiation) demonstrated the presence of Hb9-GFP$^+$ motor neurons (green) as well as glia (red) throughout the entire EB. All scale bars, 100 μm.

Figure 13:
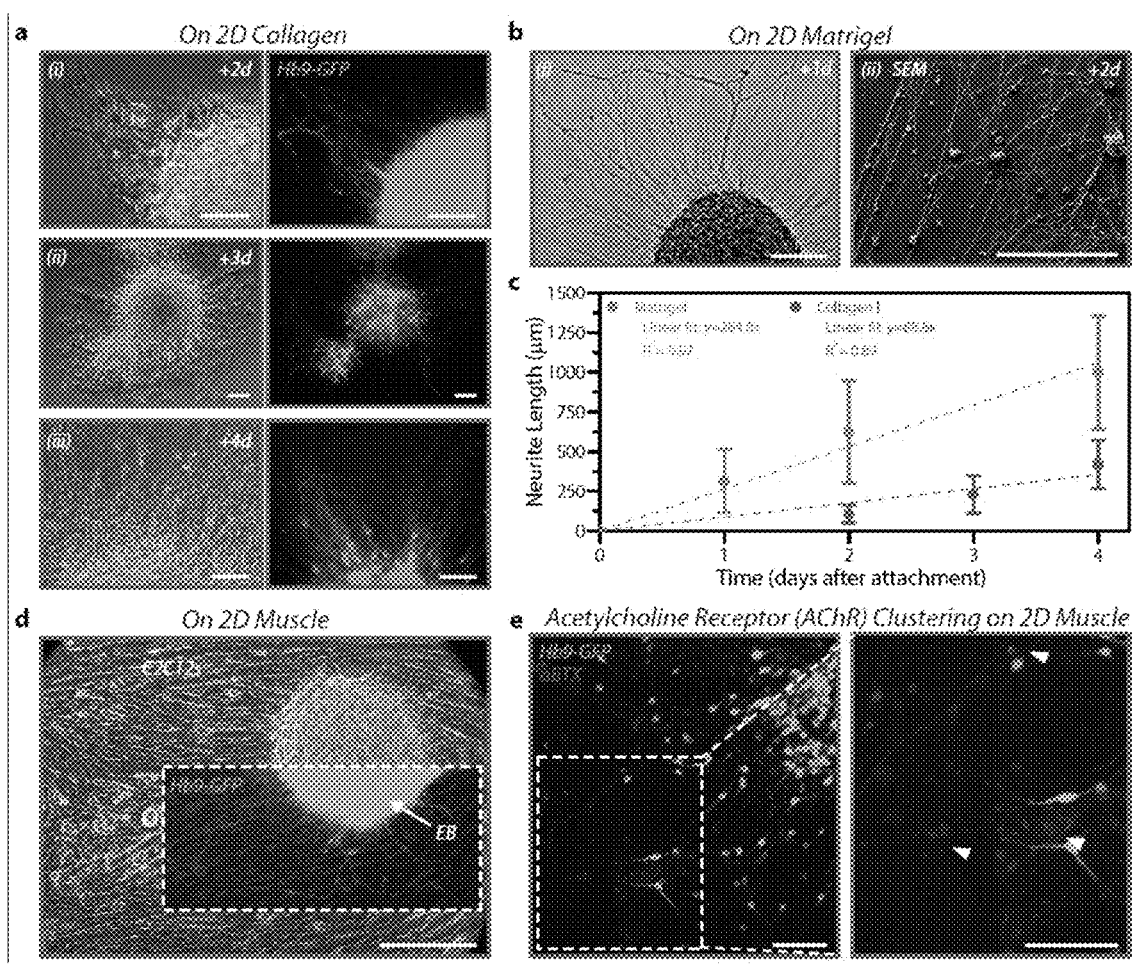

FIG. 13 panels a-e. Differentiated embryoid bodies attached readily to 2D ECM-coated substrates such as (a) collagen I (shown after (i) 2, (ii) 3, and (iii) 4 days of attachment) and (b) Matrigel™ (shown after (i) 1 and (ii) 2 days of attachment). All scale bars, 100 μm. (c) The EBs extended GFP$^+$ neurites from motor neurons across the surface of the gels upon attachment. Plot represents mean±standard deviation (n=103-298 neurites from 3-7 images per time point). (d) EBs also attached to 2D cultures of differentiating C2C12s and extended neurites across the surface of the myotubes (shown after 1 day of attachment). Scale bar, 200 μm. (e) Clusters of post-synaptic acetylcholine receptors (AChRs, red, stained with alpha-bungarotoxin) were visible near the termination of neurite extensions on myotubes, 5 days after co-culture. Scale bars, 100 μm.

Figure 14:
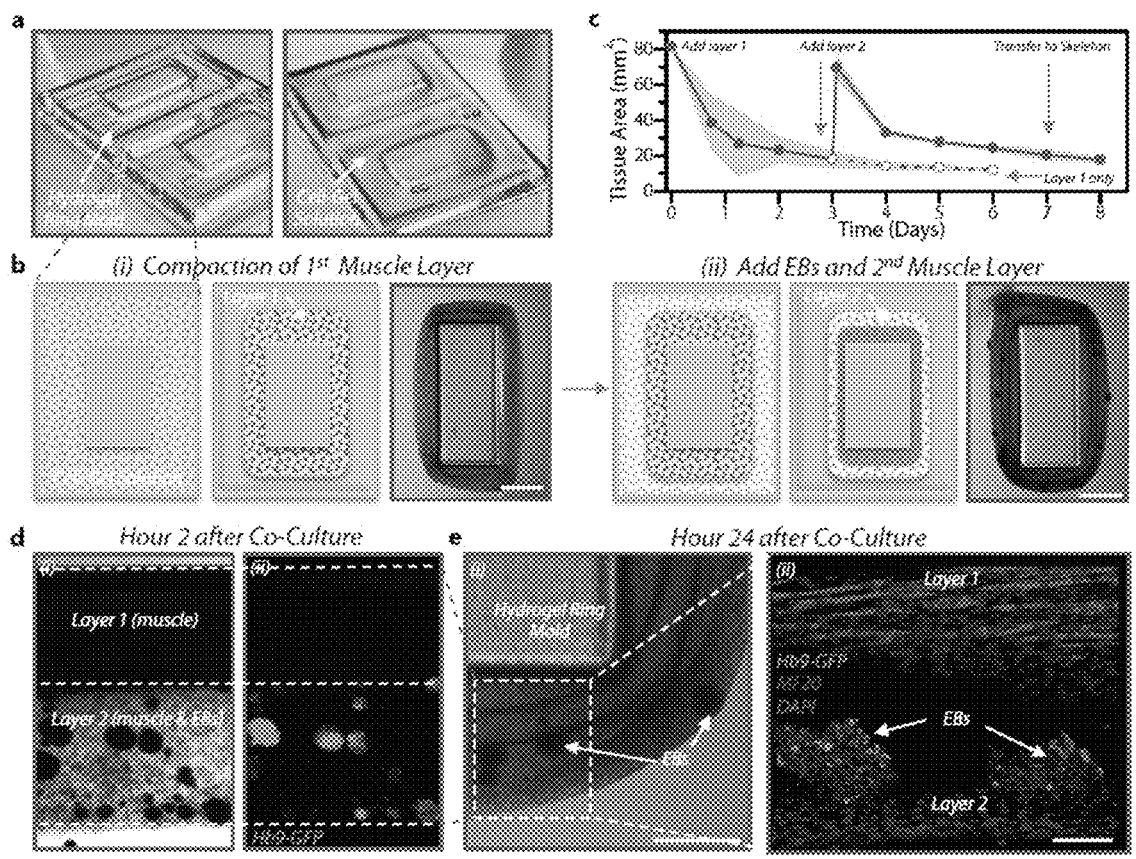

FIG. 14 panels a-e. (a) A 3D printed hydrogel structure was used as a mold to guide the formation of a liquid cell-gel solution into a solid engineered muscle tissue. (b) Schematic of two-layer muscle-neuron ring system. (i) The first layer, consisting of myoblasts and ECM proteins, compacted to form a solid muscle ring. (ii) After 3 days, cell-gel solution containing differentiated EBs was added to the mold and compacted around (and fused to) the first layer to form a second layer. Both images are shown 48 hours after cell seeding for each layer. Scale bars, 2 mm. (c) As the cell-gel solution compacted to form a muscle ring, the cross-sectional tissue area decreased over time. Plot represents mean±standard deviation (shaded area; n=3-6 rings per time point). (d) Compaction of layer 2 brought the EBs in close contact with differentiated muscle in layer 1. (i) Phase contrast and (ii) fluorescent images demonstrated the presence of EBs in layer 2, 2 hours after co-culture. Scale bar, 1 mm. (e) (i) Phase and (ii) confocal images of the two-layer system 24 hours after co-culture demonstrated multinucleated myotubes in layer 1 and GFP$^+$ motor neurons in the EBs in layer 2. Scale bar, (i) 1 mm and (ii) 100 μm.

Figure 15:
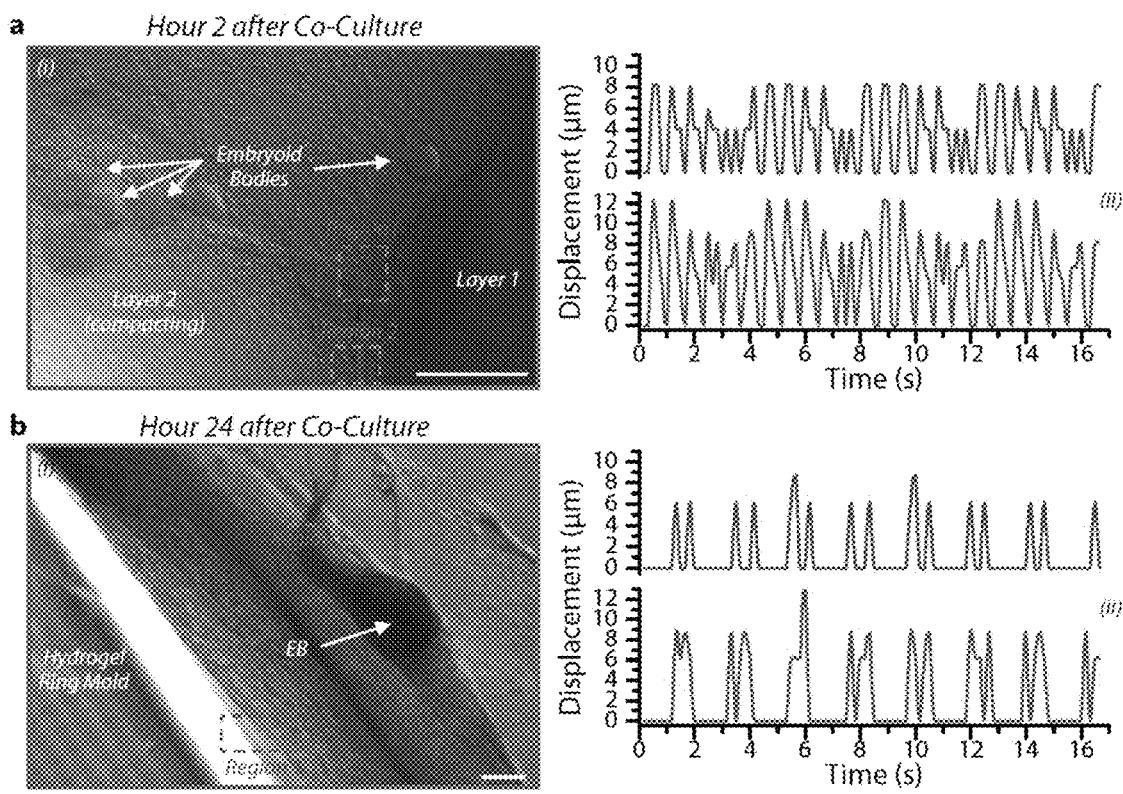

FIG. 15 panels a-b. Spontaneous contraction of the muscle in layer 1 was observed (a) 2 hours and (b) 24 hours after the addition of layer 2 containing EBs to the hydrogel ring molds. (i) Phase contrast images demonstrating two regions where spontaneous contraction was observed. (ii) Displacement was measured for two regions of muscle contraction, which followed a periodic pattern and varied slightly depending on proximity to EBs. Frequency of contraction decreased between hours 2 and 24. All scale bars, 200 μm.

Figure 16:
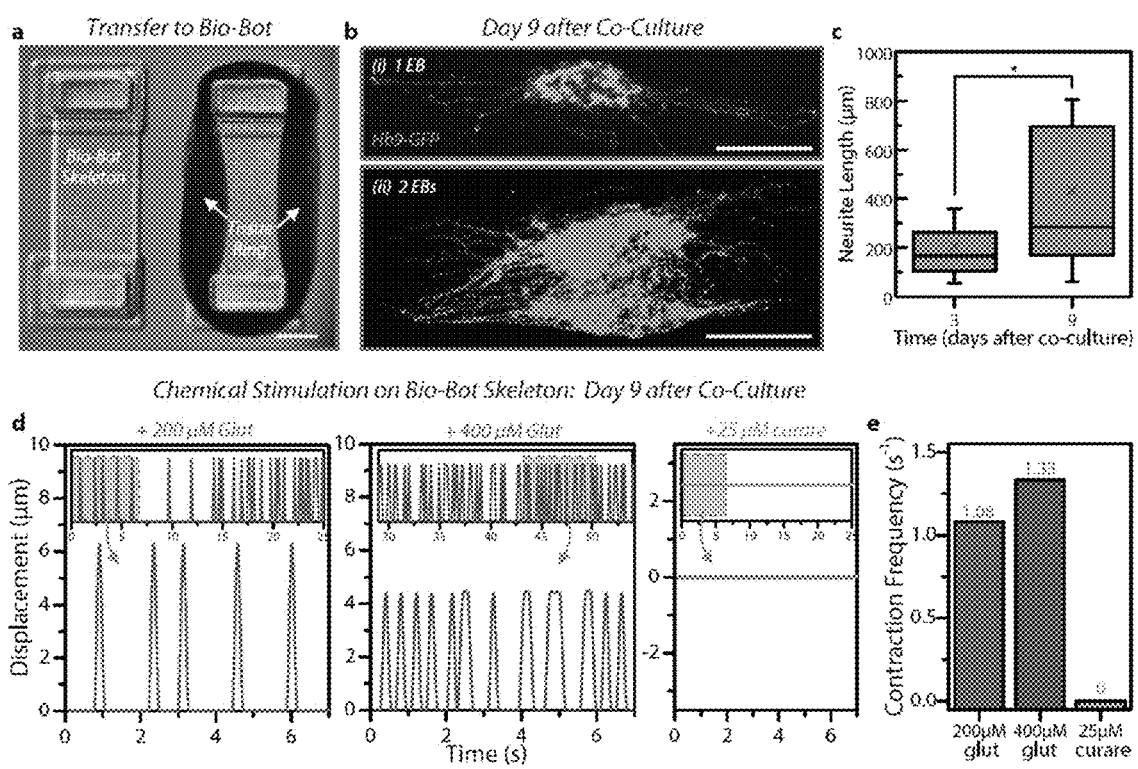

FIG. 16 panels a-e. (a) Muscle-neuron tissue rings were transferred to 3D printed bio-bot skeletons, made of a beam (chemically tethered to an underlying glass slide) connecting two pillars. Top view; scale bar, 1 mm. (b) Soon after the addition of layer 2, (i) single or (ii) groups of EBs began to extend neurites outward through the tissue (shown here 9 days after co-culture). Scale bars, 200 μm. (c) Neurite growth from EBs in tissue rings significantly increased over time. Box plots represent $25^{th}$, $50^{th}$, and $75^{th}$ percentiles, with average values marked as (x) and whiskers representing ±standard deviations (n=51-185 neurites from 4-10 EBs per time point). (d) Video recordings demonstrated that site-specific innervation of a group of muscle fibers allowed for muscle contraction via chemical stimulation, with the frequency of contraction increasing with glutamate concentration. The addition of 25 μM curare halted the contractions, indicating that muscle contraction was motor neuron-induced. (e) The frequency of contraction increased with glutamate concentration (from 1.08 to 1.33 contractions/s with 200 and 400 μM glutamate, respectively). After the addition of 25 μM curare, the frequency decreased to 0 observed contractions. Plot represents mean values.

Figure 17:
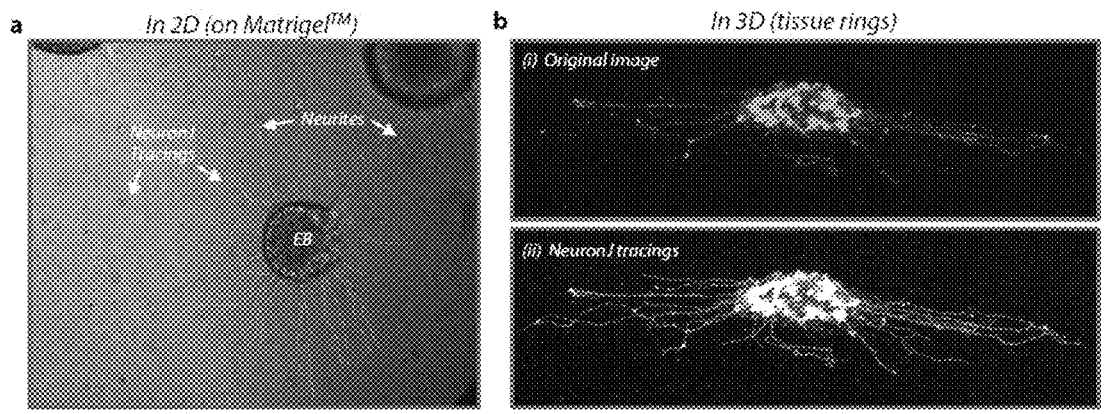

FIG. 17 panels a-b. Shows neurite growth distances in 2D (a) and 3D (b).

Figure 18:
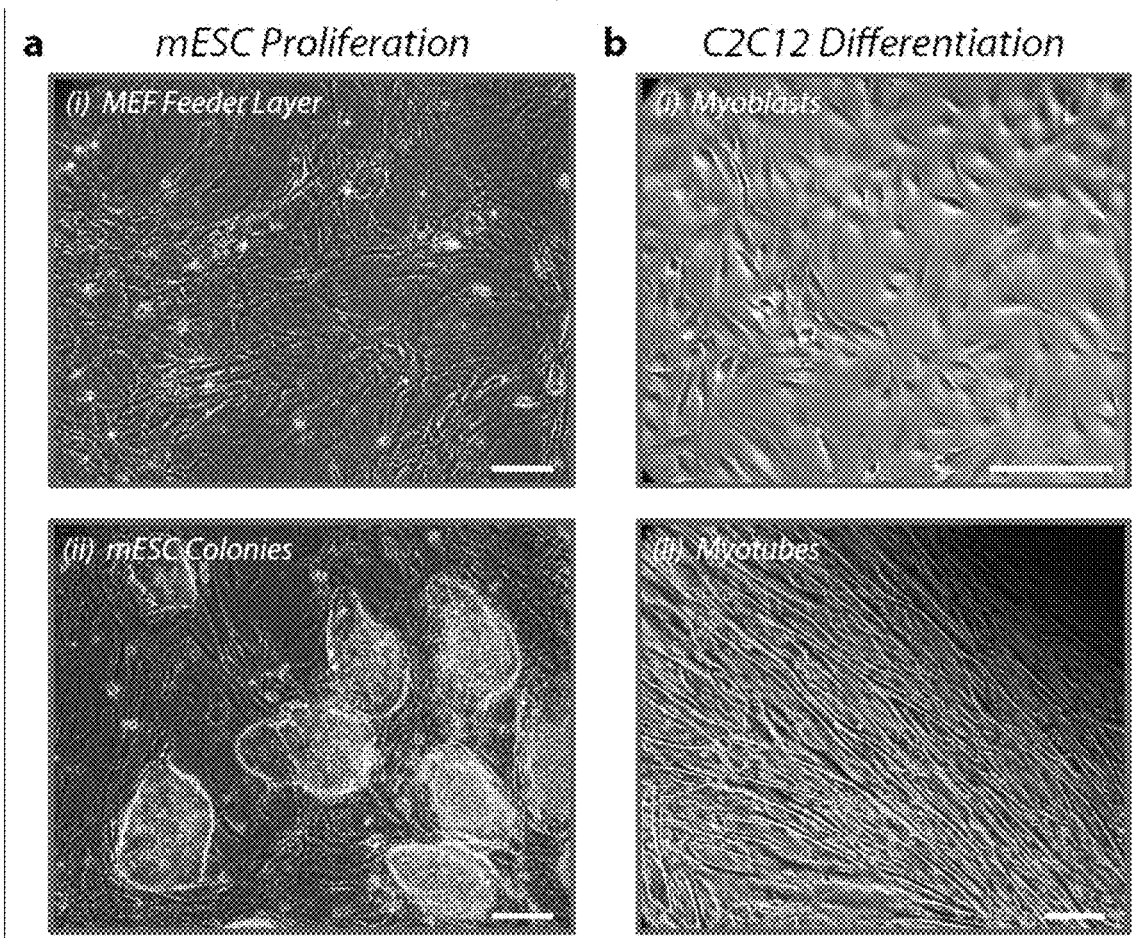

FIG. 18 panels a-b. Shows confluency of mESC cells (a) and C2C12 cells (b).

Figure 19:
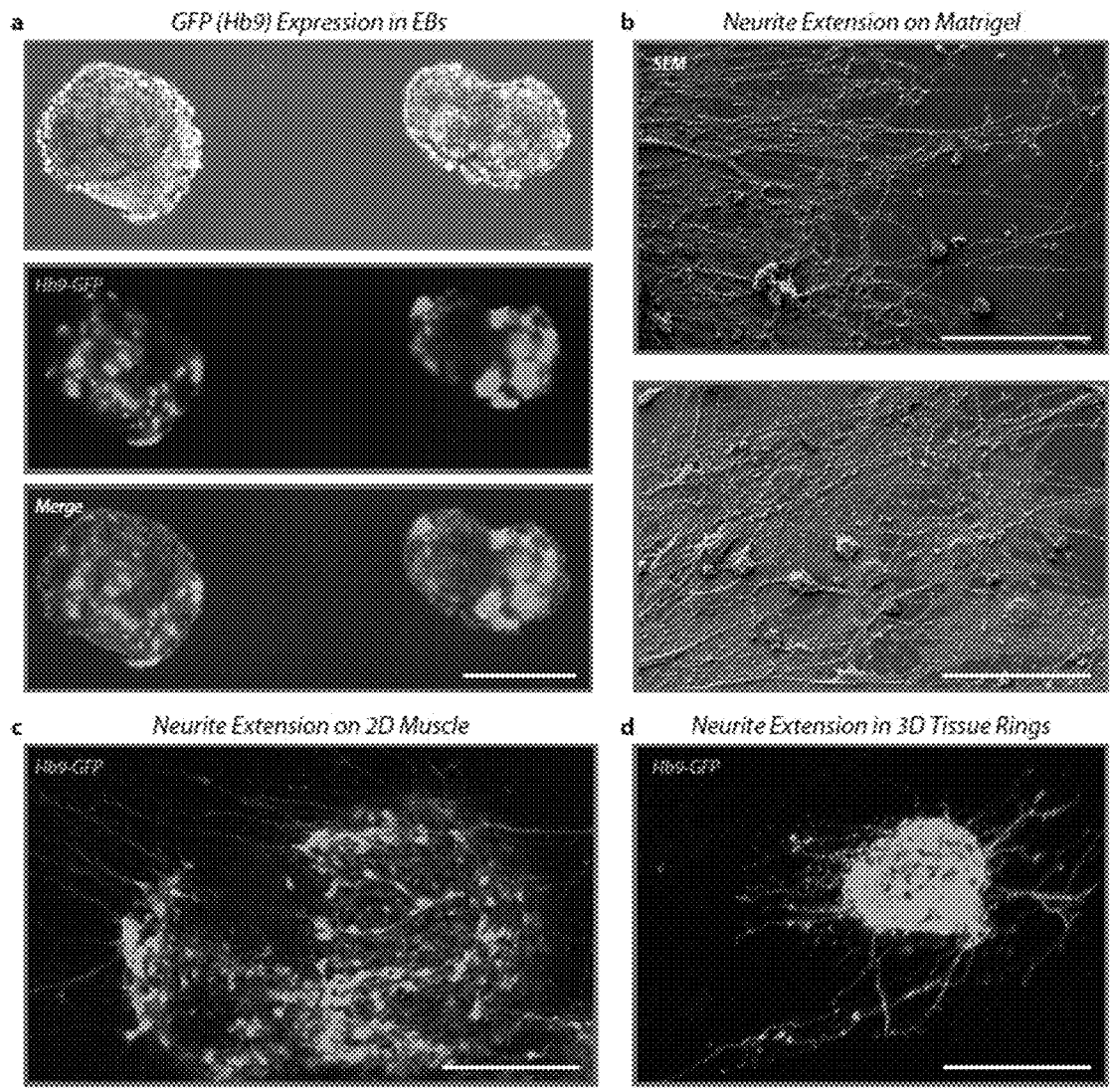

FIG. 19 panels a-d. Visual confirmation of differentiation of MNs without the addition of exogenous factors or antibodies. Cells express green fluorescent protein (GFP) under the control of the postmitotic motor neuron-specific Hb9 promoter.

Figure 20:
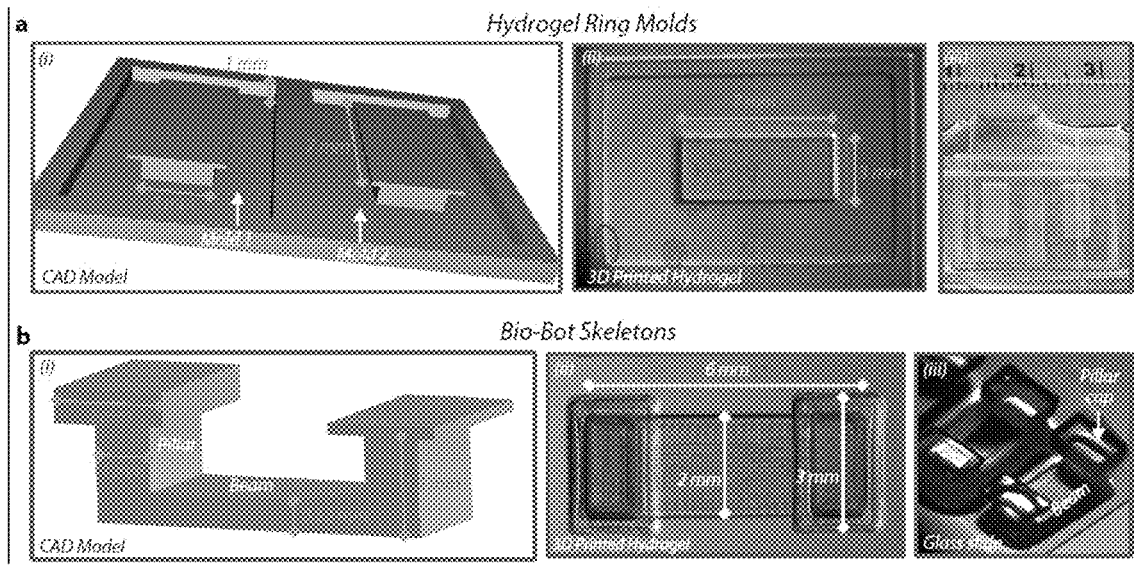

FIG. 20 panels a-b Shows the mold containing rectangular-shaped wells that forced the compacting cells and ECM into a ring-shaped tissue.

Figure 21:
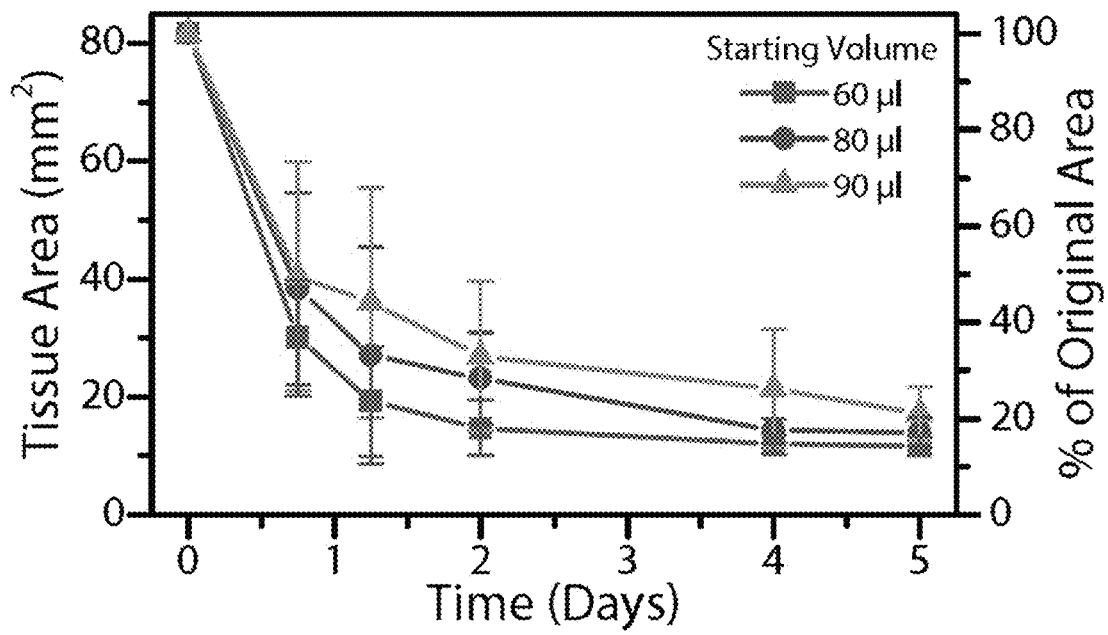

FIG. 21. Shows the cross sectional tissue area with different initial volumes.

While the compositions and methods disclosed herein are susceptible to various modifications and alternative forms, exemplary embodiments thereof are shown by way of example in the drawings and are herein described in detail. It should be understood, however, that the description of exemplary embodiments is not intended to limit the compositions and methods to the particular forms disclosed, but on the contrary, the intention is to cover all modifications, equivalents and alternatives falling within the spirit and scope of the compositions and methods as defined by the embodiments above and the claims below. Reference should therefore be made to the embodiments above and claims below for interpreting the scope of the compositions and methods.

DETAILED DESCRIPTION

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

Unless defined otherwise, all technical and scientific terms used herein have the same meaning as commonly understood by one of skill in the art to which the compositions and methods pertain.

Overview

The present disclosure describes a repeatable and customizable approach to 3D printing injection molds for engineered muscle and mechanical bio-bot skeletons. Seeding and differentiating muscle actuators within these molds are described. Methods of mechanically coupling muscle actuators to printed skeletons are described to accomplish functional output behaviors when stimulated with external signals. The convergence of the two disciplines of tissue engineering and 3D printing thus enables the iterative design and rapid fabrication of adaptive forward engineered biological machines whose functionality can be tuned to suit a variety of applications in health, security, and the environment.

Figure 1:
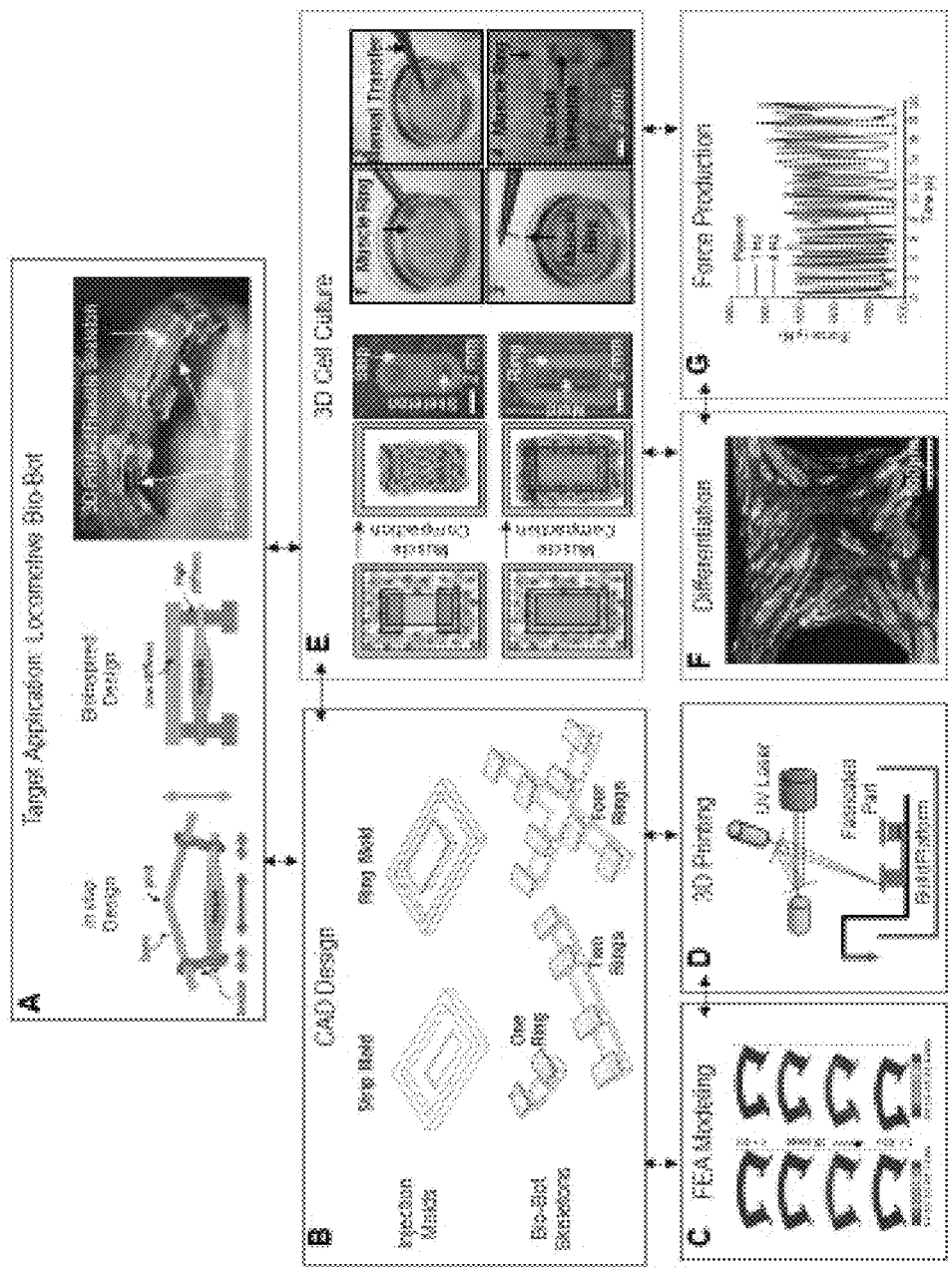
FIG. 1 panels A-G. Bio-bot design process overview. (A) Bio-bot design is inspired by biological design in the body. Bio-bot skeletons and muscle bioactuator injection molds are designed using computer aided design (CAD) software (B) (Procedural Steps 1-2), tested using finite element analysis (FEA) software (C) (Procedural Steps 26,29), and manufactured via stereolithographic 3D printing (D) (Procedural Steps 3-10). Layered tissue rings (also called muscle rings and actuators herein) are tissue engineered and coupled to bio-bot skeletons (E) (Procedural Steps 11-16), and assessed via immunohistochemical staining (F) (Procedural Step 30) and externally stimulated force production (G) (Procedural Steps 19-29). Each step of the design process (A-G) is iterative, and feedback from each step is used to improve the functionality of the bio-bot with every iteration. Figures adapted from Cvetkovic et al.[13] and Raman et al.[14].

In this protocol, a modular and step-wise approach to designing, fabricating, and controlling skeletal muscle-powered locomotive biological machines at the millimeter- to centimeter-scale is presented (FIG. 1). Stereolithographic 3D printing can be used to iteratively design and custom manufacture soft robotic devices for a variety of purposes. These 3D printed devices, when coupled to tissue engineered skeletal muscle actuators (i.e., layered tissue rings), can drive locomotion across 2D surfaces and can be designed to suit a variety of applications.

The design of 3D printed skeletons was inspired by the architecture of the musculoskeletal system in vivo. In the body, skeletal muscle is tethered to bones via tendons, and contraction of the muscle drives articulation of the bones across flexible joints. The bio-bot skeleton is thus composed of a flexible beam, mimicking an articulating joint, with for example, two pillars at each end, which serve as anchor points for tissue engineered muscle. In the first iteration of our bio-bot design[13], this skeleton was placed inside a 3D printed injection mold, which served as a template for a solution of skeletal muscle cells in a suspension of natural hydrogels. Cells seeded within this hydrogel matrix, meant to mimic the extracellular matrix in vivo, applied traction forces to compact into a dense 3D tissue, or "muscle strip", over time. When differentiated over the course of several days, the muscle strips became capable of controllable contraction in response to external electrical pulse stimuli. By introducing asymmetry into the 3D printed skeleton via a change in the length of one of the pillars, electrically stimulated contraction was shown to drive directional locomotion of muscle-powered bio-bots in the direction of the longer pillar.

A muscle strip encircles, for example, two pillars, but comprises a solid strip between the two pillars. That is a muscle strip encircles two pillars, and the muscle tissue is solid between the two pillars. See FIG. 2A. In contrast, a layered muscle ring as described herein, encircles the two pillars, but the tissue of the ring does not meet between the two pillars. Instead, a hole or opening of the ring is present between the pillars. See FIG. 2A.

Figure 2:
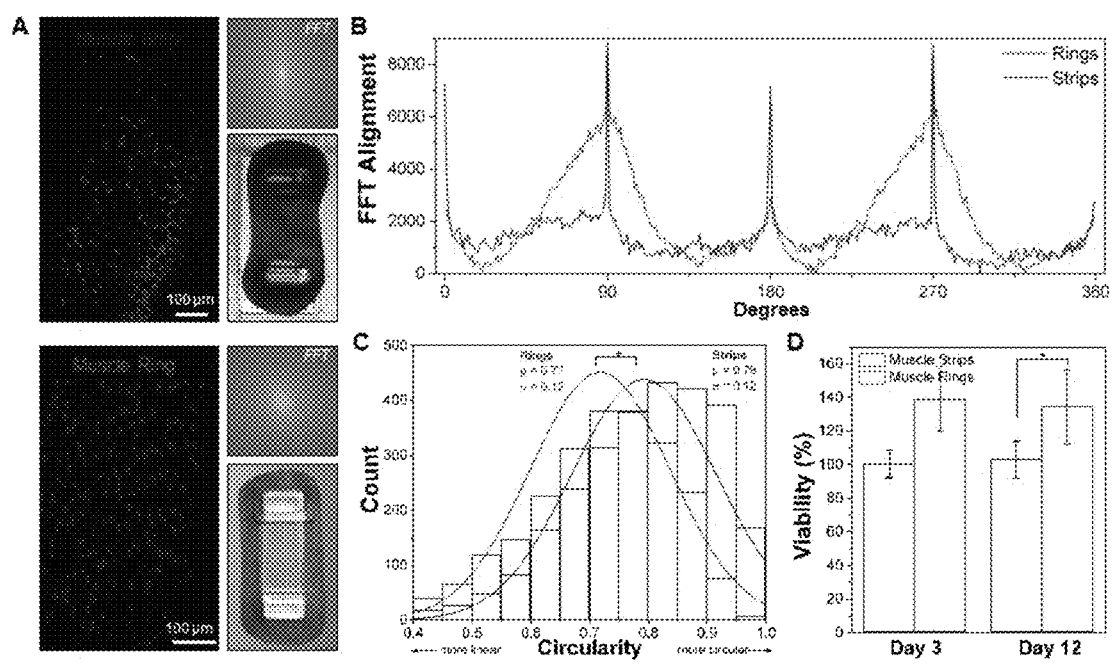
FIG. 2 panels A-D. Cellular orientation and morphology in layered tissue rings versus strips. (A) A comparison of muscle strip and muscle ring designs and the effect on cellular orientation. (B) Analysis of overall nuclear alignment (representative of myofiber orientation) was performed with FFT analysis of DAPI-stained regions of both tissue designs at day 12. While both curves have peaks at 90° and 270° (the common longitudinal axis of the bio-bot), muscle rings display a wider average distribution (and increased area under the curve) around these axes, indicating a higher degree of local and global alignment as compared to muscle strips. FFT curves represent averages of individual FFT analyses (n=8 regions analyzed for muscle rings, n=5 for muscle strips, with 2 samples per design; individual curves are shown in FIG. 9. (C) The circularity significantly decreased in muscle rings compared to muscle strips, revealing a more elongated nuclear profile and higher degree of alignment along the length of the ring (n=16 total regions analyzed for muscle rings, n=8 for muscle strips, containing images from 2 different z-planes; both from 2 samples each). Data from normal distributions represent mean values±standard deviations; individual data points are shown in FIG. 9; *=p<0.05. (D) Cellular viability, determined by a MTS assay, was statistically increased on day 12 for muscle rings versus strips. Columns and error bars represent mean values±standard deviations; *=p<0.05.
Figure 3:
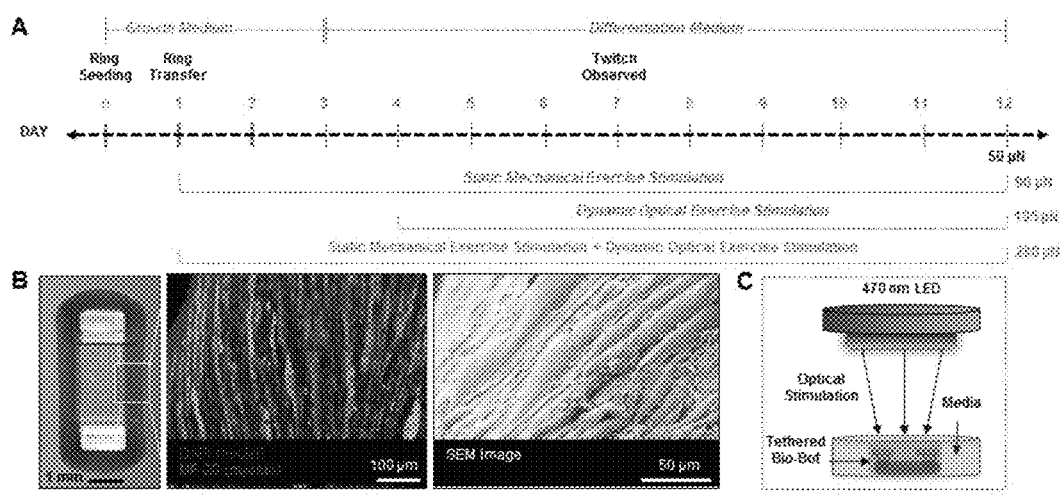
FIG. 3 panels A-C. Muscle differentiation protocol. (A) Timeline of muscle maturation, indicating the effect of biochemical and mechanical exercise signals on muscle functionality. Functionality is assessed via comparison of muscle active tension force production in response to optical stimulation at 1 Hz. (B) Immunohistochemical and scanning electron microscopy (SEM) images of mature myotubes within differentiated muscle rings, showing a dense population of contractile myotubes with a high degree of local alignment. (C) Schematic of optimal exercise stimulation protocol, which combines both a static mechanical stimulus (imposed by tethering the bio-bot to an underlying glass coverslip) and a dynamic optical pulse stimulus.
Figure 9:
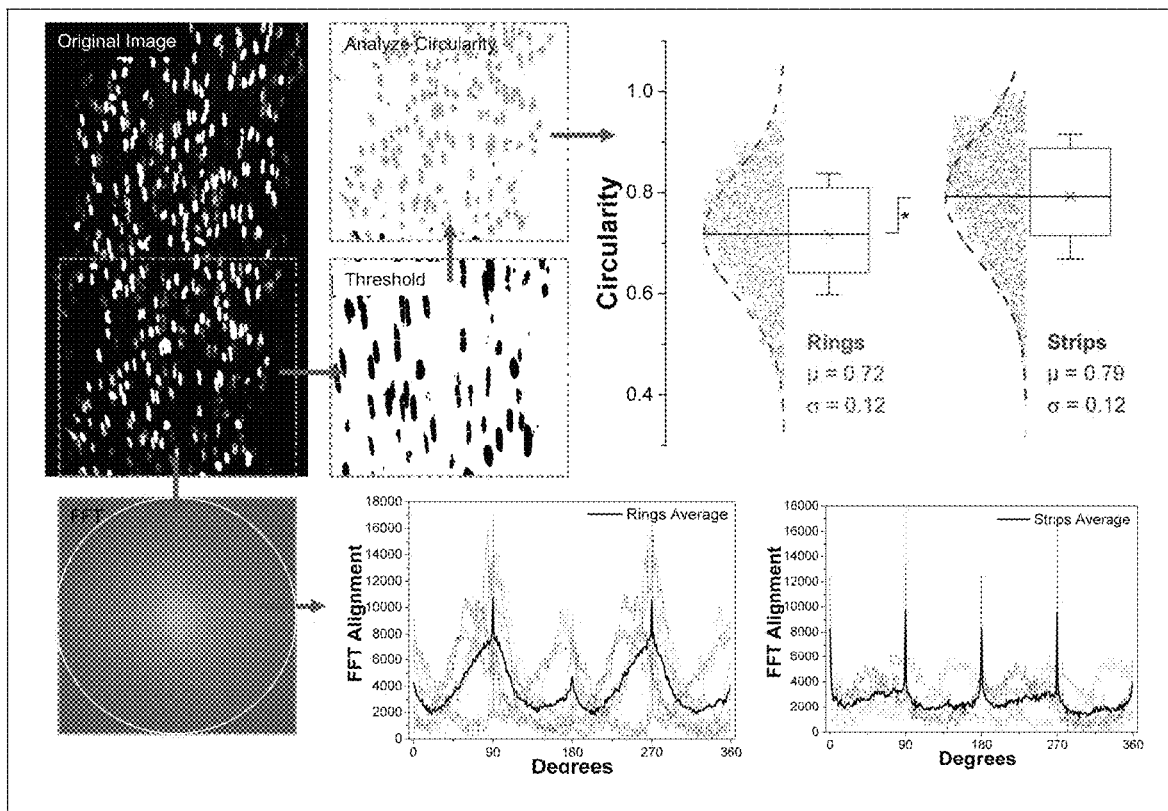
FIG. 9. Cellular alignment and circularity analysis. Starting with a fluorescent image of cellular nuclei, convert the image to binary. To calculate circularity, apply a threshold to the binary image and use the Analyze Particles feature in ImageJ to bin and plot the circularity (1=circular; 0=linear) for each data set. To compute alignment, perform FFT analysis on similarly-oriented images and plot the results (radial sums) as a function of degrees. (See Supplementary Method 3 for more information.) Circularity plots represent all data points from FIG. 2c (n=2312 total nuclei for muscle rings; n=2702 for muscle strips). Data from normal distributions represent mean values±standard deviations; *=p<0.05. FFT Alignment plots represent individual curves for muscle ring and strip samples; averaged data are shown in bold black lines on each plot (and plotted together for comparison in FIG. 2b).

U.S. patent application Ser. No. 14/486,375 discusses previous bio-bot compositions and is hereby incorporated by reference. The previous design of these bio-bots has at least two significant limitations. First, the muscle tissue strip was engineered in a way that permanently tethered it to the bio-bot skeleton, making it difficult to adapt the methodology for different skeleton designs. Second, since electrical stimulation drove contraction of the entire body of muscle tissue, locomotion was only enabled by introducing permanent and one-directional asymmetry into the skeleton design. To target the first limitation, the 3D printed injection mold was designed to produce skeletal muscle "rings" which could be manually transferred to any of a wide variety of bio-bot skeletons. These rings produce passive and active tension forces similar to those generated by muscle strips. Analysis of the myotubes' nuclear orientation and morphology within the muscle tissue rings (also called layered tissue rings or actuators herein) revealed a higher degree of cellular alignment, metabolic activity (and cellular viability), and nuclear elongation in muscle rings as compared to the muscle strips (FIGS. 2 and 9). Alignment of myotubes along the longitudinal axis of the bio-bot provided an axis along which the majority of the mature muscle fibers contracted synchronously upon stimulation, a characteristic of hierarchical skeletal muscle in vivo. Layered tissue rings are three-dimensional (3D) aggregates of cells, which are different from two-dimensional (2D) monolayer cells cultured on flat and rigid substrates.

Figure 11:
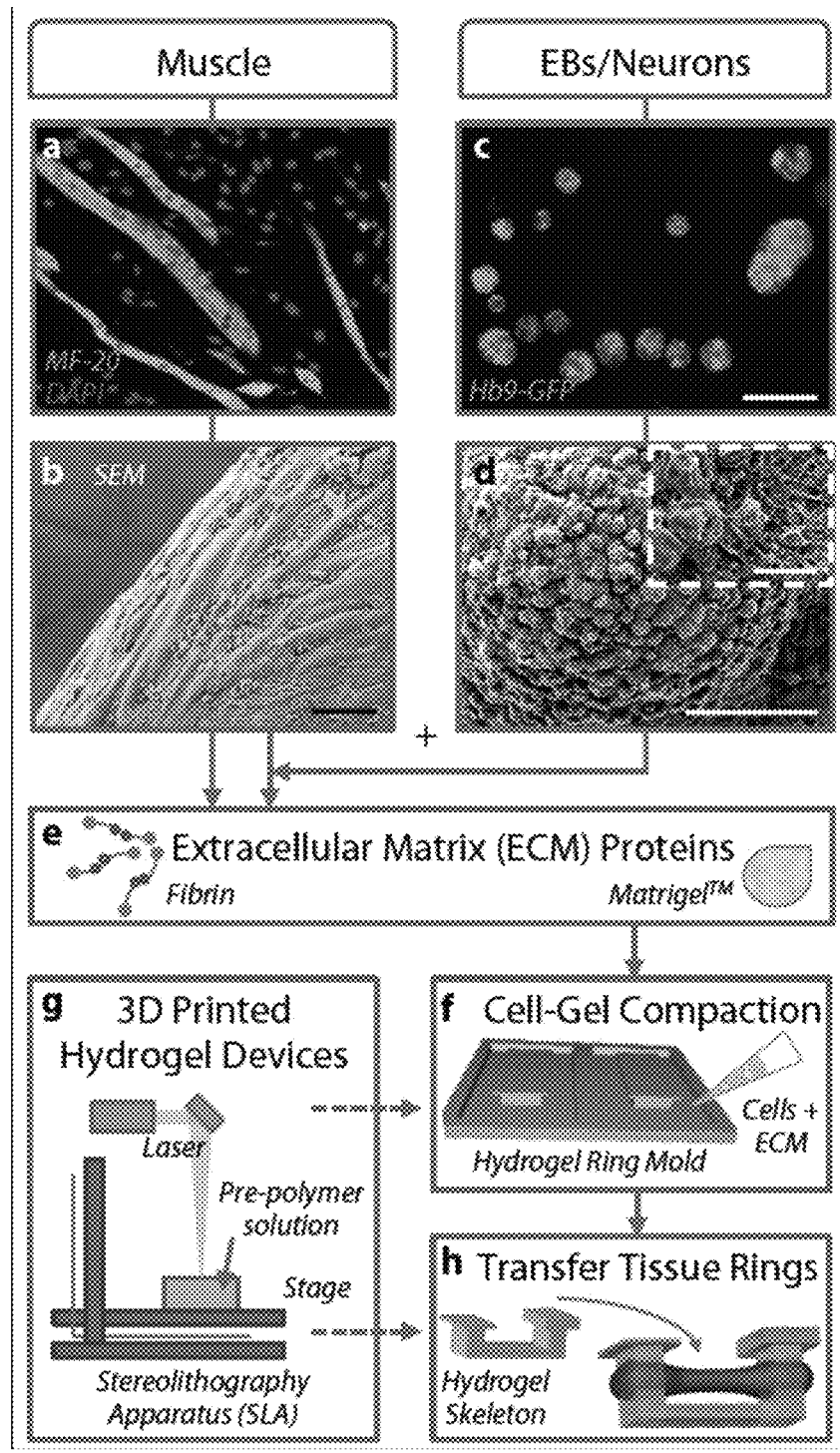
FIG. 11 panels a-h. Skeletal muscle cells and motor neurons were combined into a fabricated 3D co-culture system. C2C12 myoblasts were differentiated into multinucleated myotubes (a), and combined with extracellular matrix (ECM) proteins to create an engineered muscle ring tissue (b). In parallel, mouse embryonic stem cells (HBG3 mESCs) were differentiated into motor neurons (MNs)

To target the second design limitation, the technique of optogenetics was employed to genetically engineer a light-responsive skeletal muscle cell line that could be stimulated to contract by for example, pulses of 470 nm blue light. The resultant optogenetic muscle rings were coupled to multi-legged bio-bot skeletons with symmetric geometric designs. Localized stimulation of contraction, rendered possible by the greater spatiotemporal control of light stimuli over electrical stimuli, can be used to drive directional locomotion and 2D rotational steering. Additionally, a skeletal muscle having integrated motor neurons was used, allowing for the contraction of the muscle ring to be controlled chemically (e.g. with glutamate). A modular cellular system is also disclosed, made up of multi-layered tissue rings containing integrated skeletal muscle and motor neurons (MNs) embedded in an extracellular matrix (ECM). The first layer contains differentiated skeletal muscle myotubes (FIG. 11a) mixed with ECM to form an engineered muscle tissue ring (FIG. 11b). Simultaneously, MNs are differentiated from mouse embryonic stem cells through the formation of EBs, spherical aggregations of cells grown in suspension culture (FIG. 11c-d). The EBs are mixed with ECM proteins (FIG. 11e) to form a second tissue layer that integrated with the differentiated muscle tissue ring to create a co-culture amenable to both cell types. After the multi-layered rings sequentially compacted and fused together (FIG. 11f), they can be placed on a stationary hydrogel skeleton that had been 3D printed in parallel (FIG. 11g-h).

The use of stereolithographic 3D printing (an additive rapid prototyping technique) to create a flexible yet integrated tissue arrangement allows for iterative design modifications on a range of length scales. This system demonstrates functional NMJ behavior and controllable outputs including engineered muscle contraction upon applied chemical stimulation, and permits control over physical, mechanical, and biochemical cues.

The present disclosure also provides a method for overcoming some of the challenges associated with innervating 3D muscles. MN-containing embryoid bodies are integrated into a cellular system to achieve outputs representative of a functional NMJ. A ring tissue design with directional force production allows for a physiological neuron-muscle co-culture with greater potential for innervation in 3D, while an adaptable fabrication system provides physical cues and structural support for maturation and synergy of both neurons and muscle in a relevant engineered tissue system. By allowing the two major cell types to differentiate in parallel before combining them into one co-culture system, a flexible platform is created in which cells and tissues can be combined with 3D printed scaffolds in a modular and user-friendly manner.

Compaction in a hydrogel ring mold or transfer of layered tissue rings to the skeleton does not hinder the further maturation of either major cell type. C2C12s differentiated into mature myotubes in the presence of IGF-1, whose use accelerates muscle differentiation in 3D engineered systems in a physiologically relevant manner. Forcing the tissue to compact and differentiate in this constrained environment results in greater myotube alignment along the longitudinal axis, as this static mechanical cue imposed during muscle development contributes to improved functionality and force production. Compacting means that the cross-sectional tissue depth reduces such that the myotubes and motor neurons are brought closer together. The design and fabrication of an instructive environment for this cellular system were achieved with the use of stereolithographic 3D printing. This manufacturing technology has widely been utilized for applications in tissue engineering not only due to the user's control over specific design, geometric, and mechanical parameters, but also for its ability to fabricate biomaterials (hydrogels whose properties can mimic cells' natural micro-environments) and also encapsulate various cell types in three dimensions, in a short time frame and on a range of length scales.

Mammalian NMJ forms as a result of mutually stimulating signaling from both MNs and skeletal muscle fibers. Neurons can provoke the post-synaptic terminal site at the muscle, and likewise, skeletal fibers can induce pre-synaptic differentiation on neurons. One outcome is the clustering of AChRs, which are uniformly distributed throughout myotubes but become greatly concentrated at the post-synaptic membrane, due to both AChR redistribution throughout the membrane and increased synthesis. Another outcome is the extension and branching of the neuron's axon into a motor nerve terminal that can release neurotransmitters (such as ACh) at the NMJ. Both outcomes were observed, signifying functional NMJ formation. The extension of neurites across 2D surfaces (FIG. 13) indicates the potential to extend neurites throughout engineered tissues and innervate the skeletal muscle. Indeed, a similar phenomenon was observed in 3D multi-layered tissue rings (FIG. 16b).

In a functioning NMJ, muscle contraction is induced by an excitatory neurotransmitter that is released from a MN at the synaptic cleft between cells, which binds to a post-synaptic receptor, and depolarizes the cell on which it acts, thus increasing that cell's excitability and probability of firing an action potential. When the nicotinic neurotransmitter ACh binds to its specific membrane receptor (AChR) on the muscle cell, it initiates an intracellular signaling cascade resulting in the release of calcium ions from the sarcoplasmic reticulum in the muscle fiber, terminating in actin-myosin contraction. Before ACh is released, however, the MN must be chemically stimulated by an excitatory neurotransmitter that induces a neuronal action potential. Various studies have reported the use of glutamate in chemical activation of neuromuscular systems with high success, as it is a major excitatory neurotransmitter in the mammalian nervous system. It is demonstrated herein that site-specific innervation of a group of muscle fibers in the multi-layered tissue rings allowed for muscle contraction via chemical stimulation of MNs, with the frequency of contraction increasing with glutamate concentration. The decrease in displacement per contraction followed a physiological relationship between force output and frequency for functional skeletal muscle, the engineered tissue ring had less time to return to baseline tension between each successive stimulus as the frequency of neuronal firing increased. Because the addition of curare terminated the contractions, it was confirmed that both the muscle contraction was MN-induced as well as the presence of a functional NMJ.

Target applications include, for example, micro-scale tissue fabrication for organ-on-a-chip mimics of neurodegenerative diseases or drug screening for neuromuscular diseases in an autonomous platform.

Locomotive Biological Machines

A "biological machine" or "bio-bot" is a set of sub-components comprising living cells and cell-instructive micro-environments that interact to perform a range of prescribed tasks. Examples of prescribed tasks include sensing, information processing, transport, protein expression, and actuation. By combining clusters of different cell types, such as neurons, muscle cells, and endothelial cells, complex biological machines can be created for specific applications in health, security, and the environment. Exemplary biological machines include organ mimics for drug testing, biological robots for replication and repair, and implantable systems for drug sensing, synthesis, and release. Biological machines can have an actuation module for locomotion including controlled directional movement, referred to as an autonomous "bio-bot". Actuation produced by a cluster of muscle cells, optionally in combination with other cell types, can be used to power the bio-bot. Lithographic technology can be integrated with appropriate biomaterials to spatially organize, for example, muscle cells and neurons on a bio-bot with desired geometry, mechanics, and cell adhesion molecules for optimal and robust locomotion. A bio-bot can comprise a skeleton and one or more layered tissue rings.

Skeleton

A skeleton can be made up of one or more hydrogel beams, pillars, caps, other hydrogel structures, or combinations thereof. Hydrogel beams, pillars, caps, and other hydrogel structures are made of a hydrogel, such as a photopolymerizable hydrogel. Hydrogels can be made up of natural materials or synthetic materials or combinations thereof. Suitable hydrogels can be made up of, for example, collagen, fibrin, chitosan, hyaluronic acid, chondroitin sulfate, alginate, agar/agarose polyethylene (PE), polyethylene glycol (PEG), polyethylene oxide (PEO), polyethylene glycol diacrylate (PEGDA), poly(ethylene glycol)-dimethacrylate (PEGDMA), polyacrylamide, polylysine, oligo(poly (ethylene glycol) fumarate) (OPF), polydimethylsiloxane (PDMS), polypropylene (PP), poly(propylene fumarate) (PPF), poly(N-isopropylacrylamide) (PNIPA, PNIPAAm, NIPA, PNIPAA or PNIPAm), poly(lactic) acid (PLA), poly-L-lactide (PLLA), polyvinyl acetate (PVA), polysulfone, polyvinylchloride (PVC), polytetrafluoroethylene (PTFE), polyetheretherketone (PEEK), poly(lactic-co-glycolic acid) (PLGA), poly(propylene fumarate) (PPF), poly(aldehyde guluronate), Polycaprolactone (PCL), polyphenylene oxide (PPO), PEO-PPO-PEO, PLGA-PEG, PLGA, PEG-PLLA-PEG, PCL-PEG-PCL, PCLA-PEG-PCLA, PEG-PCL-PEG, acrylated forms of polyethylene glycol, acrylated forms of polydimethylsiloxane, acrylated forms of polyacrylamide, or combinations thereof.

In one embodiment the hydrogel beam, pillar, cap, or any other hydrogel structure described herein is made of a biocompatible hydrogel that can break down over time within for example, a mammalian body. For example, a hydrogel structure can comprise a PEG hydrogel with degradable units. PEG can be rendered degradable by short peptides in its backbone for enzymatic cleavage by cells on or with the hydrogel (Adelöw et al., *Biomaterials*, 2008, 29(3), 314-326) or by making a copolymer with a hydrolytically degradable polymer like PLA (Metters et al., *Polymer*, 2000, 41, 3993-4004). In another embodiment a hydrogel is a mixture of PEG diacrylate (PEGDA) and acrylic-PEG-collagen (PC). Collagen I can be modified on the lysine groups with acrylic groups to UV cross-link to the PEG backbone in the presence of a photoinitiator.

In one embodiment a hydrogel beam is an elongated shape such as rectangular shape with a length, width, and a thickness. The length of the elongated beam is greater than the width. The length of the hydrogel beam can be about 0.075, 0.1, 0.5, 1, 2, 3, 4, 5, 6, 7, 8, 9, 10, 11, 12, 13, 14, 15, 20, 30, 40, 50, 100, 200, 300, 400, 500 or more mm (or any range between about 0.075 and about 500 mm) or about 500, 400, 300, 200, 100 50, 40, 30, 20, 15, 14, 13, 12, 11, 10, 9, 8, 7, 6, 5, 4, 3, 2, 1, 0.5, 0.1, 0.075 mm or less (or any range between about 500 mm and about 0.075 mm). The width of the beam can be about 0.05, 0.1, 0.5, 1, 2, 3, 4, 5, 6, 7, 8, 9, 10, 11, 12, 13, 14, 15, 20, 30, 40 50, 100, 200, 300, 400 or more mm (or any range between about 0.05 and about 400 mm) or about 500, 400, 300, 200, 100, 50, 40, 30, 20, 15, 14, 13, 12, 11, 10, 9, 8, 7, 6, 5, 4, 3, 2, 1, 0.5, 0.1, 0.05 mm or less (or any range between about 400 mm and about 0.05 mm). The thickness of the beam can be about 50, 60, 70, 80, 90, 100, 125, 150, 175, 200, 225, 250, 275, 300, 325, 350, 375, 400, 425, 450, 475, 500, 525, 550, 575, 600, 650, 700, 750, 1,000, 2,000, 3,000 μm or more (or any range between about 50 and about 3,000 μm) or 3,000, 2,000, 1,000, 750, 700, 650, 600, 575, 550, 525, 500, 475, 450, 425, 400, 375, 350, 325, 300, 275, 250, 225, 200, 175, 150, 125, 100, 90, 80, 70, 60, 50 μm or less (or any range between about 3,000 and about 50 μm). The height of the beam can be about 0.05, 0.1, 0.5, 1, 2, 3, 4, 5, 6, 7, 8, 9, 10, 11, 12, 13, 14, 15, 20, 30, 40 50, 100, 200, 300, 400 or more mm (or any range between about 0.05 and about 400 mm) or about 500, 400, 300, 200, 100, 50, 40, 30, 20, 15, 14, 13, 12, 11, 10, 9, 8, 7, 6, 5, 4, 3, 2, 1, 0.5, 0.1, 0.05 mm or less (or any range between about 400 mm and about 0.05 mm).

A hydrogel beam can be any shape or size, including for example, rectangular, ovoid, triangular, or circular. A hydrogel beam can be, in general, an elongated shape. The hydrogel beam has an upper and lower surface. The upper and lower surfaces (or any hydrogel surface described herein) can be generally smooth or can be textured or non-textured. Examples of surface textures include ridges, hills, grooves, mesas/plateaus, terraces, trenches, surface pores, and so forth. Nanotextures have at least one dimension that is less than 100 nm in length. For example, a ridge or trench that is 10 nm wide by 50 microns long is a nanostructure, because it is has at least one dimension (e.g., its width), which is less than 100 nm in length.

The elastic moduli of the hydrogel pillars, beams, caps, or other hydrogel structures can be about 100, 200, 300, 400, 500, 600, 700, 800, 900, 1,000 kPa or more (or any range between about 100 and about 1,000 kPa) or about 1,000, 900, 800, 700, 600, 500, 400, 300, 200, 100 kPa or less (or any range between about 1,000 and about 100 kPa). In an embodiment, a hydrogel beam can have a kPa of about 5, 10, 15, 20, 22, 25, 30, 35, 40, 45, 50, 55, 60, 65, 70, 75, 80, 90, 100, 150, 200, 250 or more (or any range between about 5 and about 250) or about 250, 200, 150, 100, 90, 80, 75, 70, 65, 60, 55, 50, 45, 40, 35, 30, 25, 22, 20, 15, 10, 5 or less (or any range between about 250 and about 5).

A hydrogel beam, pillar, cap, or other structure can be made of a hydrogel, such as a photopolymerizable hydrogel (e.g. PEGDA) of weight average molecular weight (Mw) of about 500, 1,000, 1,250, 1,500, 1,750, 2,000, 2,225, 2,500, 2,750, 3,000, 3,250, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000 Mw or more (or any range between about 500 and about 8,000 Mw) or 8,000, 7,750, 7,500, 7,250, 7,000, 6,750, 6,500, 6,250, 6,000, 5,750, 5,500, 5,250, 5,000, 4,750, 4,500, 4,250, 4,000, 3,750, 3,500, 3,400, 3,250, 3,000, 2,750, 2,500, 2,225, 2,000, 1,750, 1,500, 1,250, 1,000, 500 Mw or less (or any range between about 8,000 or about 500 Mw). The weight average molecular weight of the pillars, beams and caps of a hydrogel structure can all be the same or they can be different for each of the pillars, beams and caps.

The hydrogel beam, pillars, caps, or other structures can have a swelling ratio (Q) of about 2, 4, 5, 7, 10, 12, 15, 17, 20, 22, 25, 27, 30, 32, 35, 37, 40, 42, 45 or more (or any range between about 2 and about 45) or a swelling ratio of about 45, 42, 40, 37, 35, 32, 30, 27, 25, 22, 20, 17, 15, 12, 10, 7, 5, 4, 2, or less (or any range between about 45 and 5 about 2). The average pore size of the hydrogel beam, pillars, or other structures can be about 2, 3, 4, 5, 6, 7, 8, 9, 10, 11, 12, 13, 14, 15, 16, 17, 18, 19, 20, 25, 30 or more nm (or any range between about 2 and about 30 nm) or about 30, 25, 20, 19, 18, 17, 16, 15, 14, 13, 12, 11, 10, 9, 8, 7, 6, 5, 4, 3, 2 or less nm (or any range between about 30 and about 2 nm).

In an embodiment the hydrogel beams, pillars, caps, and other structures (including a skeleton) has a viscosity of about 4.0, 4.5, 4.6, 4.7, 4.8, 4.9, 5.0, 5.1, 5.2, 5.3, 5.4, 5.5, or 5.6 E-3 mPa·s (or a range between about 4.0 and 5.6 mPa·s.

Skeleton Structure

A skeleton can comprise one or more hydrogel pillars attached to one or more hydrogel beams. One or more of hydrogel pillars can have the same height as other hydrogel pillars of a skeleton or can have different heights than the other hydrogel pillars. Additionally or alternatively, one or more hydrogel caps can have the same thickness as other caps of a skeleton or can have different thicknesses than the other caps. These alternative heights and thicknesses can provide asymmetry for one type of locomotion of a bio-bot. In one embodiment, at least half of the pillars or caps will be higher or thicker than the other half of pillars and caps. The bio-bot will locomote toward the direction of the higher/thicker pillars and caps.

Figure 4:
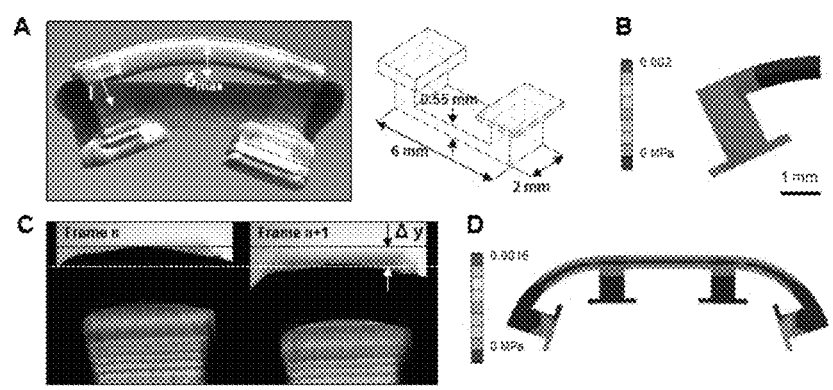
FIG. 4 panels A-D. Calculation and FEA verification of passive and active tension force production. (A) Side-view images of bio-bots (left) and geometric parameters of bio-bot skeletons (right) are used to derive the passive tension force produced by muscle ring bioactuators. (B) The calculated value of passive tension force produced can be verified via finite element analysis (FEA) simulations. (C) Top-view videos of bio-bots stimulated via electrical or optical pulse signals are used to derive the active tension force produced by muscle ring bioactuators. (D) The calculated values of active tension force produced can be verified via finite element analysis (FEA) simulations.

A hydrogel pillar can be any shape, for example, square, rectangular or ovoid. A hydrogel pillar can have a length and width. See FIG. 4. The length and width can be about 0.050, 0.075 0.1, 0.5, 1, 2, 3, 4, 5, 6, 7, 8, 9, 10, 11, 12, 13, 14, 15, 20, 30, 40, 50, 100, 200, 400, 500 or more mm (or any range between about 0.05 and about 500 mm) or about 500, 400, 300, 200, 100, 50, 40, 30, 20, 15, 14, 13, 12, 11, 10, 9, 8, 7, 6, 5, 4, 3, 2, 1, 0.5, 0.1, 0.075, 0.05 mm or less (or any range between about 400 mm and about 0.05 mm). The width of a hydrogel beam can be same or the width of a hydrogel pillar can be smaller or larger than the width of the hydrogel beam.

A cap can be coupled to the bottom base surface of a pillar and can be any shape, for example, square, rectangular or ovoid. The cap has a length, width, and a thickness. The length and the width of the cap are each greater than the length and width of the pillar to which it is coupled. The length and width of the cap can be about 0.060, 0.075 0.1, 0.5, 1, 2, 3, 4, 5, 6, 7, 8, 9, 10, 11, 12, 13, 14, 15, 20, 30, 40, 50, 100, 200, 300, or more mm (or any range between about 0.06 and about 300 mm) or about 300, 200, 100, 50, 40, 30, 20, 15, 14, 13, 12, 11, 10, 9, 8, 7, 6, 5, 4, 3, 2, 1, 0.5, 0.1, 0.075, 0.06 mm or less (or any range between about 300 mm and about 0.06 mm). The thickness of the cap can be about 25, 50, 60, 70, 80, 90, 100, 125, 150, 175, 200, 225, 250, 275, 300, 325, 350, 375, 400, 425, 450, 475, 500, 525, 550, 575, 600, 650, 700, 750, 1,000, 2,000, 3,000 µm or more (or any range between 25 about 3,000 µm) or 3,000, 2,000, 1,000, 750, 700, 650, 600, 575, 550, 525, 500, 475, 450, 425, 400, 375, 350, 325, 300, 275, 250, 225, 200, 175, 150, 125, 100, 90, 80, 70, 60, 50 µm or less (or any range between about 3,000 and about 50 µm). In one embodiment all pillars within a skeleton have a cap on their bottom base surfaces.

A skeleton can have two or more pillars (e.g. 2, 3, 4, 5, 6, 7, 30 8, 9, 10, 15, 20, 26, 30, 36, 40, 46, 50 or more (or any range between about 2 and 50 pillars), which can be separated by about 0.1, 0.5, 1, 2, 3, 4, 5, 6, 7, 8, 9, 10, 15, 20, 25, 25 30, 40, 45, 50 mm or more (or any range between about 0.1 and about 50 mm) or about 50, 40, 30, 25, 20, 15, 10, 9, 8, 7, 6, 5, 4, 3, 2, 1, 0.5, 0.1 mm or less (or any range between about 50 and about 45 mm) as measured between the outer edges of the pillars.

Methods of Making Skeleton

Embodiments provide methods of making biological machines. Two or more hydrogel pillars can be coupled to a hydrogel beam using, for example, a stereo-lithographic apparatus and polymerizable liquid materials. The two or more pillars can then be surrounded with a layered tissue ring.

A skeleton of a locomotive biological machine can be made by any methods known in the art. In one embodiment, the hydrogel structures of locomotive biological machines can be made using, for example, a stereo-lithographic apparatus ("SLA"). A SLA is a rapid prototyping tool used to produce models, prototypes, and patterns by repetitive deposition and processing of individual layers. It uses an ultraviolet laser (at, for example, 325 nm) to directly write on and polymerize photosensitive liquid materials based on a computer-aided design (CAO)-based digital blueprint, sliced into a collection of 20 cross-sectional layers, and processed into a real part using layer-by-layer polymerization. The thickness of each layer can be about 25, 50, 75, 100, 125, 25 150, 175, 200 or more µm (or any range between about 25 and 200 µm) or about 200, 175, 150, 125, 100, 75, 50, 25 or less µm (or any range between about 100 and 20 µm). The automated, high-throughput process can be particularly useful for the development of cellular systems due to its multi-material capability, which has been used with photo-polymerizable hydrogels to pattern cells or proteins at precise locations on the 30 structure. Because of their excellent spatial control, it is possible to create 3D structures with multi-cellular components that are required for complex tissue function A hydrogel solution, such as a photopolymerizable hydrogel and a photoinitiator can be added to a culture dish at specific volumes and at specific positions. Photoinitiators can be, for example, 1-[4-(2-hydroxyethoxy)-phenyl]-2-hydroxy-2-methyl-1-propane-1-one (Irgacure 2959), 1-hydroxy-cyclohexyl-phenyl-ketone (Irgacure 184), 2-hydroxy-2-methyl-1-phenyl-1-propanone (Darocur 1173), methybenzoylformate (Darocur MBF), oxy-phenyl-acetic acid 2-[2 oxo-2 phenyl-acetoxy-ethoxy]-ethyl ester and oxy-phenyl-acetic 2-[2-hydroxy-ethoxy]-ethyl ester (Irgacure 754), alpha, alphadimethoxy-alpha-phenylacetopheone (Irgacure 651), 2-benzyl-2-(dimethylamino)-1-[4-(4-morpholinyl)-1-propanone (Irgacure 369), 2-Methyl-1-[4-(methylthio)phenyl]-2-Methyl-1-[4-(methylthio)phenyl] (Irgacure 907), Phosphine oxide, phenyl bis (2,4,6)-trim-ethyl benzoyl) (Irgacure 819), Bis (eta 5-2,4-cyclopenta-dien-1-yl) (Irgacure 784), Idonium (Irgacure 250), acetophenone, anisoin, anthraquinone, anthraquinone-2-sulfonic acid, (benzene) tricarbonylchromium, benzyl, benzoin, benzoin ethyl ether, benzoin isobutyl ether, benzoin methyl ether, benzophenone, 3,3',4,4'-benzophenonetetracarboxylic dianhydride, 4-benzolbiphenyl, 2-benzyl-2-(dimethyl-amino)-4'morpholinobutyrophenone, 4,4'-bis(diethylamino) benzophenone, 4,4'bis(methylamino)benzophenone, camphorquinone, 2-chloroth ioxanthen-9-one (cumene) cyclopentadienyliron (ii) hexafluorophosphate, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone, 3,4-dimethylbenzophenone, diphenyl(2,4,6-trimethylbenzoyl)phosphine oxide, 4'-ethoxyacetophenone, 2-ethylantraquinone, ferrocene, 3'-hydroxyacetophenone, 4'-hydroxyacetophenone, 3-hydroxyacetophenone, 4-hydroxyacetophenone, 1-hydroxy-2-methylpropiophenone, 2-methylbenzophenone, 3-methylbenzophenone, 2-methyl-4'-(methylthio)-2-morphol inopropiophenone, phenanthrenequinone, 4'-phenoxyacetophenone, thioxanthen-9-one, triarylsulfonium hexafluoroantimonate, triarylsulfonium hexafluorophosphate, (DSG), Dithiobis[succinimidyl propionate] (DSP), Disuccinimidyl suberate (DSS), Disuccinimidyl tartarate (DST), 3,3'-Dithiobis[sulfosuccinimidylpropionate] (DTSSP), Ethylene glycol bis[succinimidylsuccinate] (EGS), Ethylene glycol bis [sulfosuccinimidylsuccinate] (Sulpho-EGS), Tris-succinimidyl am inotriacetate (TSAT), 1-Ethyl-3-[3-dimethylaminopropyl]carbodiimide hydrochloride (EDC), N-hydroxysuccinimide (NHS), (N-hydroxysulfosuccinim-ide) (Sulfo-NHS), dicyclohexylcarbodiimide (DCC), Sulfo-succinimidyl (4-iodoacetyl)aminobenzoate (Sulfo-SIAB), Succinimidyl (4-iodoacetyl)aminobenzoate (SIAB), Succinimidyl 3-(bromoacetamido)propionate (SBAP), Succinimidyl iodoacetate (SIA), Sulfosuccinimidyl 4-(N-maleim-idomethyl)cyclohexane-1-carboxylate (Sulfo-SMCC), Succinimidyl 4-(N-maleimidomethyl)cyclohexane-1-car-boxylate (SMCC), Succinimidyl 4-(N-maleimidomethyl)cy-clohexane-1-carboxy-(6-amidocaproate) (LC-SMCC), N-epsilon-Maleimidocaproyl-oxysulfosuccinimide ester (Sulfo-EMCS), N-epsilon-Malemidocaproyl-oxysuccinim-ide ester (EMCS), N-gammaMaleimidobutyryl-oxysulfos-uccinimide ester (Sulfo-GMBS), N-gam ma-Maleimidobu-tyryloxysuccinimide ester (GMBS), N-kappa-Maleimidoundecanoyl-oxysulfosuccinimide ester (Sulfo-KMUS), m-Maleimidobenzoyl-N-hydroxysulfosuccinimide ester (Sulfo-MBS), m-Maleimidobenzoyl-N-hydroxysuc-cinimide ester (MBS), Succinimidyl 4-(pmaleimidophenyl) butyrate (SMPB), Sulfo-SMPB, N-alpha-Maleim idoacet-oxysuccinimide ester (AMAS), N-beta-Maleim idopropyl-oxysuccinimide ester (BMPS), Succinimidyl 6-[(beta-male-imidopropionamido)hexanoate] (SMPH), Succinimidyl-3-(2-pyridyldithio)propionate (SPOP), Sulfosuccinimidyl 6-[3'-(2-pyridyldithio)propionamido]hexanoate (Sulfo-LC-SPOP), 4-Succinimidyloxycarbonyl-5 alpha-methyl-alpha (2-pyridyldithio)toluene (SMPT), N-beta-Maleimidopropi-onic acid hydrazide (BMPH), N-epsilon-Maleimidocaproic acid hydrazide (EMCH), N-kappaMaleimidoundecanoic acid hydrazide (KMUH), 4-(4-N-Maleimidophenyl)butyric acid hydrazide (MPBH), 3-(2-Pyridyldithio)propionyl hydrazide (POPH), p-Maleimidophenyl isocyanate (PMPI), 1,4-Bismaleimidobutane (BMB), Bismaleimidohexane (BMH), Bismaleimidoethane (BMOE), Oithiobismaleimi-doethane (OTME), Tris(2-maleimidoethyl)amine (TMEA) or combinations thereof.

One or more types of cells, one or more cell-binding proteins, one or more additional proteins or combinations thereof can be added to the pre-polymerization solution of any of the hydrogel structures.

An ultraviolet laser beam can be used to selectively cross-link the hydrogel beams and hydrogel pillars00 at specified energy doses. The energy doses of the laser can be varied by controlling the scan speed. Laser exposure energies can be about 50, 100, 150, 200, 250, 300, 350, 400, 450, 500, 550, 600, 650, 700, 750, 800, 850, 950, 1,000 mJ cm$^{-1}$ or more (or any range between about 50 and about 1,000) or about 1,000, 950, 900, 850, 800, 750, 700, 650, 600, 550, 500, 450, 400, 350, 300, 250, 200, 150, 100, 50 mJ cm$^{-1}$ or less (or any range between about 1,000 and about 50). Other cross-linkers include, for example, N-Sulfosuccinimidyl-6-(4'-azido-2'-nitrophenylamino) hexanoate (Sulfo-SANPAH), N-5-Azido-2-nitrobenzoyloxysuccinimide, NHS-Diazirine (SDA), dimethyl adipimidate (DMA), dimethyl pimelimidate (DMP), dimethyl suberimidate (DMS), dithiobispropionimidate (DTBP), Bis[sulfosuccinimidyl] suberate (BS3), Bis[2-(succinimidooxycarbonyloxy)ethyl] sulfone (BSOCOES), Disuccinimidyl glutarate (DSG), Dithiobis[succinimidyl propionate] (DSP), Disuccinimidyl suberate (DSS), Disuccinimidyl tartarate (DST), 3,3"-Dithiobis[sulfosuccinimidylpropionate] (DTSSP), Ethylene glycol bis[succinimidylsuccinate] (EGS), Ethylene glycol bis [sulfosuccinimidylsuccinate] (Sulpho-EGS), Tris-succinimidyl am inotriacetate (TSAT), 1-Ethyl-3-[3-dimethylaminopropyl]carbodiimide hydrochloride (EDC), N-hydroxysuccinimide (NHS), (N-hydroxysulfosuccinimide) (Sulfo-NHS), dicyclohexylcarbodiimide (DCC), Sulfo-succinimidyl (4-iodoacetyl)aminobenzoate (Sulfo-SIAB), Succinimidyl (4-iodoacetyl)aminobenzoate (SIAB), Succinimidyl 3-(bromoacetamido)propionate (SBAP), Succinimidyl iodoacetate (SIA), Sulfosuccinimidyl 4-(N-maleimidomethyl)cyclohexane-1-carboxylate (Sulfo-SMCC), Succinimidyl 4-(N-maleimidomethyl)cyclohexane-1-carboxylate (SMCC), Succinimidyl 4-(N-maleimidomethyl)cyclohexane-1-carboxy-(6-amidocaproate) (LC-SMCC), N-epsilon-Maleimidocaproyl-oxysulfosuccinimide ester (Sulfo-EMCS), N-epsilon-Malemidocaproyl-oxysuccinimide ester (EMCS), N-gamma-Maleimidobutyryl-oxysulfosuccinimide ester (Sulfo-GMBS), N-gamma-Maleimidobutyryl-oxysuccinimide ester (GMBS), N-kappa-Maleimidoundecanoyl-oxysulfosuccinimide ester (Sulfo-KMUS), m-Maleimidobenzoyl-N-hydroxysulfosuccinimide ester (Sulfo-MBS), m-Maleimidobenzoyl-N-hydroxysuccinimide ester (MBS), Succinimidyl 4-(p-maleimidophenyl) butyrate (SMPB), Sulfo-SMPB, N-alpha-Maleim idoacetoxysuccinimide ester (AMAS), N-beta-Maleimidopropyl-oxysuccinimide ester (BMPS), Succinimidyl 6-[(beta-maleimidopropionamido)hexanoate] (SMPH), Succinimidyl-3-(2-pyridyldithio)propionate (SPDP), Sulfo-succinimidyl 6-[3'-(2-pyridyldithio)propionamido]hexanoate (Sulfo-LC-SPDP), 4-Succinimidyloxycarbonyl-alpha-methyl-alpha(2-pyridyldithio)toluene (SMPT), N-beta-Maleimidopropionic acid hydrazide (BMPH), N-epsilon-Maleimidocaproic acid hydrazide (EMCH), N-kappaMaleimidoundecanoic acid hydrazide (KM UH), 4-(4-N-Maleimidophenyl)butyric acid hydrazide (MPBH), 3-(2-Pyridyldithio)propionyl hydrazide (PDPH), p-Maleimidophenyl isocyanate (PMPI), 1,4-Bismaleimidobutane (BMB), Bismaleimidohexane (BMH), Bismaleimidoethane (BMOE), Dithiobismaleimidoethane (DTME), Tris(2-maleimidoethyl)amine (TMEA) or combination thereof.

In an embodiment, a pre-polymer solution of a polymer and photoinitiator can be pipetted onto a substrate. A laser beam can be used to selectively cross-link the structures into the hydrogel pillar and beam structures. The elevator on the printer can be used to cross-link the hydrogel in all directions. One or more types or molecular weights of hydrogels can be used in one hydrogel beam, hydrogel base, hydrogel cap, other hydrogel structure, or hydrogel skeleton by removing uncross-linked hydrogel solution and adding different hydrogel solution to the structure as it is constructed. When the hydrogel structure is completed the structure can be rinsed to remove all uncrosslinked pre-polymer solution.

Bio-bot constructs can also be fabricated by micromolding. Molds, such as polydimethylsiloxane (PDMS) for bio-bots can be fabricated on a silicon master with SU-8 negative photoresist, as described by Chen et al., 1998, *Biotechnol. Prag.* 14: 356-363; Kane et al., 1999, *Biomaterials,* 20:2363-76. Master molds can be silanized with (tridecafluoro-1,1,2,2-tetrahydrooctyl)-1-trichlorosilane in vacuum. In some embodiments, molds are generated by pouring 1:10 curing agent to polymer onto the silicon wafer. Upon curing, a negative of the pattern from the silicon master is imprinted on the surface of the PDMS to make a bio-bot mold. Pre-polymer solution (e.g. PEGDA) comprising a photoinitiator is then applied to the PDMS molds. A coverslip can be placed over the pre-polymer solution prior to polymerization. The pre-polymer solution is then cross-linked by exposure to UV irradiation. Thereafter, the bio-bots are removed from the molds and hydrated.

Layered Tissue Rind

A layered tissue ring is a collection of muscle cells and neurons that are formed in the shape of a continuous band. The continuous band encircles a hole, similar to a ring. The layered tissue ring does not, however, have to be circular and can be, for example, oval, square, rectangular, triangular, hexagonal, etc. The ring is continuous and encircles a hole of any shape in the middle. Therefore, the term ring as used herein is not limited to circular shapes, but also encompasses continuous bands that surround a hole or empty space. See, e.g., FIG. 14a, where the ring mold is in the shape of a rectangle with a rectangular hole (or other shaped hole) in the middle resulting in a layered tissue ring in the shape of a rectangle with a rectangular cut out or hole in the middle. The continuous, layered tissue ring encircles the rectangular cut out or hole. A ring does not include a "strip" configuration of, for example, FIG. 2A. A strip configuration encompasses tissue that surrounds, for example, two pillars, but is solid or connected for at least a portion of the strip between the pillars. That is no continuous hole or continuous empty space in a muscle strip between the pillars.

A layered tissue ring can be any size or shape, and is designed to be the appropriate length to fit around two or more hydrogel pillars, or to fit around multiple hydrogel pillars throughout a skeleton. The size of the layered tissue ring will depend on the design, size, and shape of the skeleton. In an embodiment, the thickness of the layered tissue ring can be between about 1 μm and about 500 μm, a thickness that allows nutrients to be able to diffuse into the tissue beyond this section. In some embodiments, the thickness of the layered tissue ring is less than about 10, 50, 100, 200, 300, 400, 500, or 750 μm (or any range between about 10 and 750 μm).

One or more cell types can be used to make layered tissue ring to attach to the hydrogel of the skeleton (e.g., the hydrogel pillars). Cells can be obtained from any mammal (e.g., human, murine, bovine, ovine, feline, canine, etc.). Cell types include, for example, neurons, skeletal muscle cells, cardiac muscle cells, endothelial cells, fibroblasts, or combinations thereof. Examples of other cell types that can be used include a human embryonic stem cell, a mesenchymal stem cell, a bone marrow-derived mesenchymal stem cell, a human bone marrow-derived mesenchymal stem cells a hematopoetic stem cell, a blood stem cell, an adult stem cell, an embryonic stem cell, a post-natal stem cell, a fetal cardiomyocyte, an endothelial cell, an endothelial progenitor cell, circulating angiogenic cells, circulating endothelial precursors, endothelial colony-forming cells, early outgrowth endothelial progenitor cells, late outgrowth endothelial progenitor cells, a cord blood stem cell, an autotransplanted expanded cardiomyocyte, a cardiomyocyte, a cardiac myoblast, a myofibroblast, a fibroblast, an adipocyte, a totipotent cell, a pluripotent cell, a multipotent mesenchymal stem cell, a synovial cell, a spinal disc cell, a tenocyte, a myoblast, a muscle cell, a neuron, a bone marrow cell, a mesenchymal cell, a parenchymal cell, an endothelial cell, a mesothelial cell, a fibroblast, a myofibroblast, an osteoblast, a chondrocyte, an exogenous cell, an endogenous cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell (e.g., a multi-potent progenitor cell of neurons, cardiac muscle cells, skeletal muscle cells, endothelial cells, fibroblasts), a unipotent progenitor cell, a monocyte, a skeletal myoblast, a macrophage, a capillary endothelial cell, a xenogenic cell, an allogenic cell or combinations thereof.

Muscle cells are skeletal muscle cells, cardiac muscle cells, autotransplanted expanded cardiomyocytes, cardiomyocytes, cardiac myoblasts, myofibroblasts, myoblasts, myofibroblasts, myocardial cells, multi-potent progenitor cell of muscle cells, skeletal myoblasts and muscle progenitor cells. In one embodiment, the muscle cells are skeletal muscle cells. In one embodiment, the one or more cell types forming a layered tissue ring comprise motor neurons and muscle cells, wherein the muscle cells form one or more muscle fibers and wherein the neurons and muscle fibers interact to form one or more neuromuscular junctions.

Endothelial cells and/or fibroblast cells can be present along with cardiac muscle cells, skeletal muscle cells, other muscle cells, or neurons. The endothelial and/or fibroblast cells can form vascular networks for muscle tissue. The endothelial and/or fibroblast cells can be present within the gel along with the muscle cells. Microchannels can be present in the skeleton. See, Jeong et al., Advanced Materials 24:1 (2012). The microchannels can be about 100 µm to about 2.5 mm in diameter and have on-center spacing between the microchannels that is about 100 µm to about 2.5 mm. The endothelial and/or fibroblast cells can secrete one or more proangiogenic factors, growth factors, or antiangiogenic factors. The microchannels and endothelial cells and/or fibroblast cells can provide a microvasculature for the muscle cells.

Cells can be primary cells, cell lines (which proliferate virtually indefinitely), or a combinations thereof. In an embodiment cells used in the layered tissue ring are not primary cells.

In an embodiment an undifferentiated layered tissue ring comprises a first ring shaped layer comprising and undifferentiated muscle progenitor cells (e.g., myoblasts) in a gel and a second ring shaped layer comprising embryonic stem cells, embryoid bodies (i.e., three-dimensional aggregates of pluripotent stem cells), neural progenitor cells in a gel, or combinations thereof.

In an embodiment a layered tissue ring comprises a first ring shaped layer comprising and differentiated myoblasts (e.g., myotubes) in a gel and a second ring shaped layer comprising motor neurons and differentiated myoblasts in a gel, wherein the first and second layers are fused into a layered tissue ring. The gel portion of the layered tissue ring starts out as a liquid, which polymerizes to a form a viscoelastic solid. The gel remains in the ring structure and mimics the extracellular matrix that surround cells within, for example, a mammalian body.

Cells and Gel of Three Dimensional Muscle Cell Powered Bio-Bot

One or more types of cells and a solution capable of forming a gel can be used in making a layered tissue ring. The gel solution can comprise one or more extracellular matrix proteins. Extracellular matrix proteins can be, for example types I, II, III, IV, V, VI, VII, VIII, IX, X, XII, or XII collagen, fibronectin, fibrin, fibrillin, thrombin, fibronogin, elastin, laminin, undulin, nidogen, tenasin, vitronectin, osteonectin (SPARC), thrombospondin, biglycan, decorin, lumican, aggrecan, syndecan, perlecan, Matrigel® matrix protein mixture (Corning), Geltrex® basement membrane matrix (Life Technologies), Cultrex® (Trevingen®) basement membrane extract, Applied Cell Extracellular Matrix (ABM), polylysine or combinations thereof. In one embodiment the gel comprises Collagen I, collagen IV, laminin, and entacin. The concentration of collagen can be about 0.2, 0.5, 0.8, 1.0, 1.2, 1.4, 1.8, 2.0, 2.5, 3.0, 3.5, 4.0 or mg/ml$^{-1}$. In an embodiment the gel comprises fibrinogen, thrombin, and Matrigel® matrix protein mixture (Corning). Fibrinogen can be present in a concentration of about 1, 2, 3, 4, 5, 6, 7, 8, 9, 10 or more mg/mL$^{-1}$. Matrigel® matrix protein mixture can be present at a concentration of about 10, 20, 30, 40, 50 60% or more v/v. Thrombin can be present at a concentration of about 0.1, 0.2, 0.3, 0.4, 0.5, 0.6, 0.7, 0.8, 0.9, 1.0 U mg-fibrinogen$^{-1}$ thrombin.

The gel can further comprise proteins or other chemicals or moieties such as cell adhesion domains, growth factors, hydrolytic polypeptides, proteolytic polypeptides including for example, Insulin growth factor type 1 (IGF-1), Nerve growth factor (NGF), basic fibroblast growth factor (b-FGF), acidic fibroblast growth factor (a-FGF), RGD peptides, RGDS peptides, RGDC peptides, KQAGDV peptides, YIGSR peptides, WSPW peptides, aminocaproic acid, aprotinin, leupeptin, pepstatin or combinations thereof.

In one embodiment, a protease inhibitor can be added to the gel and cell solution mixture. Protease inhibitors include, for example, 8-aminocarproic acid or aprotinin. The protease inhibitor can be added at about 0.1, 0.5, 1.0, 2.5, 5, 7, 10 or more mg/ml.

The cells can be present in the gel at a cell concentration of about $1\times10^2$, $1\times10^3$, $1\times10^4$, $2.5\times10^4$, $5\times10^4$, $1\times10^5$, $2.5\times10^5$, $5\times10^5$, $1\times10^6$, $2.5\times10^6$, $5\times10^6$, $1\times10^7$, $2.5\times10^7$, $5\times10^7$, $1\times10^8$, $2.5\times10^8$, $5\times10^8$ or more cells ml$^{-1}$.

Methods of Making Layered Tissue Ring

Methods of making a layered tissue ring are provided herein. Myoblasts or other muscle progenitor cells and a gel solution can be added to a ring mold. The myoblasts can be allowed to differentiate into mature muscle fibers to form a first layer. Embryonic stem cells can be induced to differentiate into embryoid bodies. Embryoid bodies or other neuron progenitor cells, and a gel solution are added to the ring mold to form a second layer. The myoblasts are allowed to differentiate into mature muscle fibers and the embryoid bodies are allowed to differentiate into motor neurons. The first and second layers can be allowed to condense in the mold and fuse such that a layered tissue ring is formed. All cells, cultures, and layered tissue rings can be incubated at about 37° C. and at about 5% $CO_2$.

One or more types of cells can be mixed with a gel solution comprising one or more extracellular matrix proteins and growth medium and added to the ring mold to make the layered tissue rings. The cells can be cardiac muscle cells, skeletal muscle cells, myoblasts, or other muscle progenitor cells. The gel and cell solution is allowed to gel. Cell growth medium can be added after gelation. In one embodiment, the cells are myoblasts and after allowing for cell growth in the gel, the myoblasts can be induced to differentiate. Insulin-like growth factor-1 (e.g., about 20, 30, 40, 50, 60, 70, 80, 90, 100 or more ng/mi-1 and/or protease inhibitors (e.g., about 0.1, 0.5, 1.0, 2.5, 5, 7, 10 or more mg/ml can also be added to the gel within the hydrogel structures. Other types of cells can also be induced to differentiate within the gel.

Myoblasts (e.g., C2C12s, which are murine myoblasts) can be maintained in muscle growth medium. Cells in culture can be passaged before confluence. In an embodiment embryonic stem cells (e.g., mouse embryonic stem cells (mESCs)) can be prepared by pre-plating a feeder layer of embryonic fibroblasts (e.g., mouse CF-1 mitomycin-C inactivated MEFs) about 2 days prior to stem cell culture. Embryonic stem cells (e.g., HBG3 mESCs (Hb9-GFP)) can be expanded on top of the MEF layer in proliferation medium. Cells can be passaged before colonies reach confluence.

To initiate differentiation, embryonic stem cells can be switched to, e.g., neural differentiation medium. After incubation the cells can be trypsinized, centrifuged, and replated (day 0). On about day 1, floating cells in suspension can be collected and replated in a new dish, and adhered cells can be discarded. On about day 2, floating embryoid bodies (EBs) can be collected and replated in differentiation medium. On about day 5, floating EBs can be collected and the medium supplemented with complete neural differentiation medium. Differentiated EBs, which can be GFP+, can be used between about days 5-7.

To form a first layer of a tissue ring, about $5 \times 10^6$ myoblasts $ml^{-1}$ (final density of C2C12s in the cell-gel solution) can be combined with fibrinogen, thrombin, and Matrigel™ basement membrane on ice (this is an example of a cell-gel solution). Muscle growth medium can be added to the cell-gel solution and the solution can be added to a well of a hydrogel ring mold (day 0). The cells can be incubated for about 2 h before adding warm growth medium, which can be exchanged daily. On about day 1, the first layer can be switched to muscle differentiation media. After about 3 days, the cells of layer 1 differentiate and compact in the ring mold. On about day 3, layer 2 can be added to the hydrogel ring molds and allowed to compact around layer 1. Layer 2 contains differentiated EBs (which can be GFP+) mixed with the cell-gel solution as described for Layer 1. Layered issue rings can be incubated for about 2 h. Warm complete neural differentiation medium can be added. Layer 2 can compact around layer 1. Layer 1 and Layer 2 can fuse into a single tissue (i.e., a layered tissue ring). The EBs of layer 2 form motor neurons, which can extend neurites towards other motor neurons and towards differentiated muscle cells. The neurites can be about 200, 300, 400, 500, 600, 700, 900, 1,000 µm in length.

Ring Molds

A mold (e.g. 3D printed mold) can be made in any shape or size and can be used as a template or mold for the layered tissue rings. Cells embedded in a gel solution along with other factors, can be injected into a mold and allowed to incubate until the cells self-assemble to form a continuous ring. Layered tissue rings can be removed from the mold and manually transferred to a skeleton. The layered tissue rings can be wrapped around two or more hydrogel pillars like, for example a rubber band. Optionally the layered tissue rings can be tethered to hydrogel pillars or other portions of a skeleton.

A layered tissue ring or band can be formed in a ring-shaped mold (again, the ring shape does not need to be circular, but can be other shapes also). The mold comprises an outer side wall that corresponds to the circumference of the outer edges of the layered tissue ring and inner side walls that correspond to the inner edges of the layered tissue ring. The mold has a bottom, in which the layers will sit. The bottom of the mold is in the 2-D shape of the layered tissue ring (e.g., a rectangle with a rectangular hole or cut out in the middle (see, e.g., FIG. 14a)). As the cells and gel are added to the mold, the layers come up the outer and inner side walls such that a 3-D layered tissue ring is formed. The mold can be made of any suitable material (e.g., hydrogel, PDMS, etc.) and provided with coatings to promote release of the layered tissue ring from the mold.

A mold can contain a layered tissue ring comprising. The mold can be comprised of, for example, hydrogel in the shape of a ring. The mold can contain a layered tissue ring comprising a first ring shaped layer comprising and myoblasts or myotubes in a gel; and a second ring shaped layer comprising EBs or motor neurons in a gel. The first and second layers can be fused into a layered tissue ring and can be compacted into the mold.

In an embodiment layered tissue rings made up of one or a combination of cell types can be present at one or more locations of a skeleton and layered tissue rings of one or more other cell types can be present at one or more other distinct locations of the skeleton. In one embodiment, endothelial cells and/or fibroblast cells can also be present on or within a bio-bot along with muscle cells and neurons. The endothelial and/or fibroblast cells can form vascular networks for muscle tissue. The endothelial and/or fibroblast cells can be present within the hydrogel structure (i.e., encapsulated with in the hydrogel), or within the first, second, or both layers of the layered tissue ring.

In another embodiment, the layered tissue rings have innervated motor neurons that cause contraction in response to excitatory neurotransmitters, such as glutamate.

Additional Proteins Immobilized to Hydrogel Surface

Any hydrogel surface of the skeleton (e.g., the lower surface of the hydrogel beam) or surface of the layered tissue ring can further comprise proteins or other chemicals or moieties such as cell adhesion domains, growth factors, hydrolytic polypeptides, proteolytic polypeptides including for example, Insulin growth factor type 1 (IGF-1), Nerve growth factor (NGF), basic fibroblast growth factor (b-FGF), acidic fibroblast growth factor (a-FGF), RGD peptides, RGDS peptides, RGDC peptides, KQAGDV peptides, YIGSR peptides, WSPW peptides, aminocaproic acid, aprotinin, leupeptin, pepstatin or combinations thereof. These can be immobilized or coupled to the hydrogel or ring by any means known in the art and can be immobilized or coupled in one or more distinct locations on the hydrogel or ring surface. These proteins can also be added to the pre-polymerization solution of any of the hydrogel or ring structures such that they are present within the hydrogel or ring structures themselves. Cell adhesion domains, growth factors, hydrolytic polypeptides, proteolytic polypeptides can also be directly cross-linked into the hydrogel (e.g., PEG) backbone.

Three Dimensional Muscle-Powered Bio-Bots

A biological machine or bio-bot can comprise a skeleton comprised of two or more hydrogel pillars having top and bottom base end surfaces, wherein the two or more hydrogel pillars are coupled to a hydrogel beam at their top base end surfaces, wherein the hydrogel beam extends between the two or more hydrogel pillars; and one or more layered tissue rings comprising a first ring shaped layer comprising and myotubes in a gel; and a second ring shaped layer comprising motor neurons in a gel; wherein the first and second layers are fused into a layered tissue ring. The one or more layered tissue rings can surround two or more pillars of the skeleton like a rubber band. The two or more hydrogel pillars can have caps on their bottom base end surfaces that are not covered or in contact with the layered tissue ring.

In an embodiment a muscle ring bio-bot comprises two or more hydrogel pillars having top and bottom base end surfaces that are coupled to a hydrogel beam at their top base end surfaces, wherein the hydrogel beam extends between the two or more hydrogel pillars. See FIG. 1B. The pillar/beam structure is a hydrogel structure. A layered tissue ring comprising one or more types of cells can surround the two or more pillars like a rubber band. The two or more hydrogel pillars can have caps on their bottom base end. In an embodiment 4, 6, 8, 10 or more hydrogel pillars can be arranged in a row and all pillars can be coupled to a hydrogel beam at the top base end surfaces of the hydrogel pillars. Layered tissue rings can be wrapped around each set of two pillars. See, e.g., FIG. 1B.

In another embodiment 4, 6, 8, 10 or more hydrogel pillars can be arranged in a row and all pillars can be coupled to a hydrogel beam at the top base end surfaces of the hydrogel pillars, wherein the one or more of the hydrogel pillars are further connected via an additional hydrogel beam in one or both perpendicular directions from the row to an additional one or more pillars. The additional hydrogel beam connects the top base end surfaces of the hydrogel pillars. Layered tissue rings can be wrapped around each pair of pillars. See, for example, FIG. 4A.

In an additional embodiment, hydrogel pillars are arranged in rows and columns within a grid-like array with one or more rows of hydrogel pillars and one or more columns of hydrogel pillars. Each row of hydrogel pillars can be connected at the top base end surfaces of the hydrogel pillars by a hydrogel beam and wherein each column of hydrogel pillars is connected at the top base end surfaces of the hydrogel pillars by a hydrogel beam. The hydrogel beams can intersect at the top base end surfaces of the hydrogel pillars, but are not a "double" thickness at this intersection. That is, the grid of beams connecting the pillars can be of a uniform thickness.

A skeleton can comprise, 2, 3, 4, 5, 6, 7, 8, or more pillars. Layered tissue rings can be wrapped around 2, 3, 4, 5, 6, 7, 8, or more pillars. 2, 3, 4, 5, 6, 7, 8 or more layered tissue rings can be added to one skeleton. Each layered tissue ring can be wrapped around 2, 3, 4, 5, 6, 7, 8, or more pillars. 1 or more pillars of a skeleton may have a layered tissue ring wrapped around it.

In another embodiment a multitude of hydrogel pillars having top and bottom base end surfaces are arranged in rows and columns within a grid-like array with one or more rows of hydrogel pillars and one or more columns of hydrogel pillars. Each row of hydrogel pillars can be connected at the top base end surfaces of the hydrogel pillars by a hydrogel base, wherein the hydrogel base connects all the hydrogel pillars. The rows can have consistent spacing or each row can be a different distance from the next row. Additionally, the columns can have consistent spacing or each column can be a different distance from the next column. Besides connecting each column of pillars the hydrogel base can additionally fully cover the areas between one or more columns. Additionally, besides connecting each row of pillars the hydrogel base can additionally fully cover the areas between one or more rows. A layered tissue ring comprising one or more types of cells can surround the two or more pillars. The bottom base end surfaces of the pillars can comprise caps that are not covered or surrounded by the ring. These examples are not limiting, as many different arrangements of beams, pillars, caps, and rings are possible.

A bio-bot can be about 0.1, 1, 5, 10, 50, 100, 200, 300, 400, 500 mm or more in length (or any range between about 0.1 and 500 mm). A bio-bot can be about 0.1, 1, 5, 10, 50, 100, 200, 300, 400 mm or more in width (or any range between about 0.1 and 400 mm). A bio-bot can be about 0.1, 1, 5, 10, 50, 100, 200, 300, 400 mm or more in height (or any range between about 0.1 and 400 mm).

Figure 5:
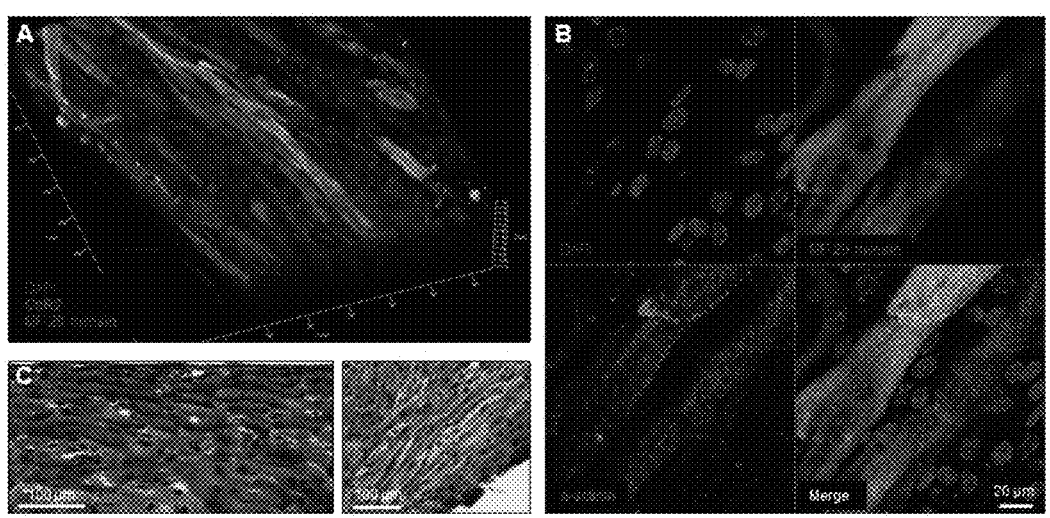
FIG. 5 panels A-C. Immunohistochemistry of engineered muscle tissues. (A) A confocal z-stack reveals the 3D nature of the muscle tissue, which contains elongated and multinucleated myotubes. Tissues were stained for mature myosin, Channelrhodopsin-2 (optogenetic ion channel), and DAPI (nuclei) (B) Confocal imaging of muscle tissue slices highlights sarcomeric striations characteristic of mature myofibers, visualized with an antibody against a-actinin protein. (C) Histological (H&E) staining distinguishes myotubes (pink) and nuclei (blue).

Layered tissue rings contain elongated, aligned, and multinucleated myotubes with sarcomeric striations, visible by a range of immunohistochemical staining and imaging methods (FIG. 5). Layered tissue rings produce passive tension forces on the order of about 1400, 1450, 1480, 1500, 1550, 1600, 1650, 1700, 1710, 1750, 1800, 1850, 1900, 1950, 2000 pN or more (or any range between about 1400 and 2000 pN). This corresponds to passive tension forces of about 2.5, 2.8, 3.0, 3.1, 3.2, 3.3, 3.4, 3.5, 3.6, 3.7 kPa or more (or any range between about 2.5 and 3.7 kPa) when divided by an average cross-sectional area of about 0.54±0.06 mm². Layered tissue rings can produce active tension forces of about 180, 185, 190, 195, 200, 205 or more (or any range between about 180 and 205 pN) (and active tension stresses of about 0.34, 0.35, 0.36, 0.37, 0.38 kPa or more), in response to optical stimulation at 1 Hz. Layered tissue rings can produce active tension forces of about 100, 105, 110, 114, 115, 120, 125, 130, or more pN (or any range between about 100 and 130 pN) (and active tension stresses of about 0.17, 0.18, 0.19, 0.20, 0.21, 0.22 or more kPa) in response to optical stimulation at 2 Hz. Layered tissue rings can produce about 90, 95, 100, 105, 110, 115, 120, 125, 130 pN or more (or any range between about 90 and 130 pN) (and active tension stresses of about 0.15, 0.16, 0.17, 0.18, 0.19, 0.20, 0.21, 0.22, 0.23, 0.24, 0.25, 0.26 kPa or more) in response to optical stimulation at 4 Hz. Stimulation with electrical pulses can produce active tension forces similar to those produced by optical stimulation. The active tension strain produced by the layered tissue rings in response to stimulation at 1 Hz is on the order of about 0.8, 0.9, 1, 1.1, or 1.2%. Unconstrained layered tissue rings (uncoupled to bio-bot skeletons) can produce strains on the order of 1.5, 2.0, 2.5, 3, 3.5, or 4.0% for short periods of time, but myotubes within the muscle rings do not retain their alignment without the mechanical strain provided by the bio-bot skeleton.

An exercise training regimen combining a static mechanical stretch stimulus and a dynamic optical pulse stimulus during differentiation can produce significantly increased active tension forces of a layered tissue ring on the order of about 240, 250, 260, 270, 280, 290, 300, 310, 320, 330, 340 pN or more (or any range between about 240 and about 340 pN) (that is about 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62 kPa or more (or any range between about 0.43 and about 0.62 kPa)) in response to optical stimulation at 1 Hz. Exercised bio-bots can produce directional locomotive speeds on the order of 225, 250, 275, 300, 312, 325, 350, 375, 400 or more µm s$^{-1}$ (or any range between about 225 and 400 µm s$^{-1}$) and 2D rotation steering speeds on the order of about 1.25, 1.5, 2.0, 2.1, 2.5, 3.0° s$^{-1}$ or more (or any range between about 1.25 and 3.0° s$^{-1}$). Locomotive speed can increase in response to exercise training, with an average increase in speed of approximately 100, 200, 300, 400, or 500% (or any range between about 100 and 500%) in response to a regimen combining static mechanical stretch and dynamic optical pulse stimuli. Locomotive speed can change in response to changing frequencies of stimulation, with an average increase in speed of approximately about 60, 70, 80, 90, or 100% when the stimulation frequency is increased from 1 to 4 Hz.

Stimulation

After a layered tissue ring is added to a skeleton, the resulting bio-bot can be stimulated or "exercised." In an embodiment, a bio-bot is exercised via mechanical stretch stimulus. Mechanical stretch stimulus can be achieved by tethering the bio-bot to a solid surface such as a glass coverslip. Mechanical stretch stimulus can be done for 0.5, 1, 2, 3, 4, 5, 6, or more days. Dynamic optical stimulation can be achieved using 450, 460, 470, 480, 490, 500 nm or other useful wavelength of light. The light can be provided in pulses of controlled frequency (e.g., about 1, 2, 3, 4, 5, 6, 7, 8, 9, or 10 hz) and pulse width of about 30, 40, 50, 60, or 70 ms. Dynamic optical stimulation can be done for 0.5, 1, 2, 3, 4, 5, 6, or more days. Dynamic electrical stimulation can be used to exercise a bio-bot. In an example, dynamic electrical stimulation includes a daily stimulation regimen of:

Stimulation with about 0.5, 1, 2, 3, or 4 Hz for about 1, 2, 3, 4, 5, 6, 7, 8, 9, or 10 minutes;

Rest for about 1, 2, 3, 4, 5, 6, 7, 8, 9, or 10 minutes;

Stimulation with about 1, 2, 3, 4, or 5 Hz for about 1, 2, 3, 4, 5, 6, 7, 8, 9, or 10 minutes;

Rest for about 1, 2, 3, 4, 5, 6, 7, 8, 9, or 10 minutes; and

Stimulation with about 2, 3, 4, 6, or 7 Hz for 1, 2, 3, 4, 5, 6, 7, 8, 9, or 10 minutes Dynamic electrical stimulation can be provided in pulses of controlled frequency (e.g., about 1, 2, 3, 4, 5, 6, 7, 8, 9, or 10 hz) and pulse width of about 30, 40, 50, 60, or 70 ms. Dynamic electrical stimulation can be done for 0.5, 1, 2, 3, 4, 5, 6, or more days. Mechanical stretch stimulus, dynamic optical stimulation, and dynamic stretch stimulus can be used alone or in combination. The stimulation techniques can be done simultaneously or sequentially.

Locomotion

In one embodiment, a bio-bot is capable of actuation, directional locomotion, controlled directional locomotion, or combinations thereof. Actuation is defined as the conversion of some form of energy into a mechanical output. Locomotion is a subset of actuation.

In one embodiment the bio-bots exhibit directional locomotion due to layered tissue ring contraction optionally coupled with asymmetry present within the structure of the hydrogel pillars and beam. The bio-bot can be placed on a substrate providing friction between the substrate and the bio-bot. Asymmetry resulting from different heights of one or more pillars or different thicknesses of one or more caps can result in locomotion. Friction between the base and the substrate upon which the bio-bot sits can be important for locomotion. Friction can be adjusted by, for example, changing the thickness of the caps, the heights of the pillars, the weight of the bio-bot, the viscosity of the medium present under or around the bio-bot, or the surface of the substrate. A bio-bot can locomote when the force produced by the layered tissue rings of the bio-bot can overcome the friction force between the base, pillars or caps and the substrate. Friction force is not affected by contact area on the macroscale, but instead on the micro-scale. Friction on the macroscale is a function of the normal force (or weight of the bio-bot device—which can be modified) and by the coefficient of friction (which is a function of the two interacting materials—which in this case is the hydrogel bio-bot and the substrate, e.g., a plastic dish lubricated with medium).

Additionally, locomotive behavior of bio-bots can be regulated by, for example, stimulation of one or more distinct portions or parts of a layered tissue ring, by for example, illumination with light of specific wavelengths, by application of an electric current, by a chemical compound, or combinations thereof resulting in locomotion. Controlled bidirectional locomotion can be achieved in any X-Y direction on a substrate, including rotation around the Z-axis. Additionally, starting, stopping and altering the speed of the locomotion is possible. Modulation of the frequency or intensity of optical pulses, frequency or amplitude of electrical stimulation, or chemical gradient can alter speed of bio-bot locomotion.

Optical methods have been developed to depolarize or hyperpolarize neurons using specific wavelengths of light. Boyden et al., *Nat. Neurosci.* 8, 1263-1268 (2005); 5 Arenkiel et al., *Neuron* 54, 205-218 (2007); Wang et al. *Proc. Natl. Acad. Sci. USA* 104, 8143-8148 (2007). This method, known as 'optogenetics,' combines the temporal and spatial precision of light pulses with cellular specificity of genetic targeting. The general strategy of optogenetics involves introducing a light-sensitive protein, such as channelrhodopsin-2 (ChR2, from e.g., green algae) to a specific cell type, illuminating the cells with defined spatiotemporal parameters, and obtaining reliable readout of the cellular behavior. Deisseroth, *Nat. Methods* 8, 26-29 (2011). This method can be used in cardiac (Bruegmann et al. *Nat. Methods* 7, 897-900 (2010); Arrenberg et al., *Science* 330, 971-974 (2010)) and skeletal (Asano et al., *Biotechnol. Bioeng.* 109, 199-204 (2012); 8akar et al. *Lab Chip* 12, 4976-4985 (2012)) muscle cells to rhythmically control their contractions. It can also be used to locally innervate specific regions of muscle tissue to generate movement in multiple degrees of freedom (multi-DOF). Optogenetics is fast, precise, and provides local stimulation of cells and tissues, relative to electrical stimulation.

Therefore, in some embodiments, polynucleotides that express one or more light-sensitive heterologous proteins are introduced into one or more specific cell types (e.g., cardiac or skeletal muscle cells, neurons, endothelial cells, fibroblasts) by methods not limited to transfection, electroporation, or microinjection. Cells comprising light-sensitive proteins are subsequently integrated into a bio-bot as described herein (e.g. into one or more cells of a layered tissue ring). Non-limiting examples of light-sensitive proteins include channelrhodopsin, e.g., channelrhodopsin-1 (ChR1), channelrhodopsin-2 (ChR2), melanopsin, photopsin, rhodopsin, UV-B resistance 8 (UVR8), cryptochrome, phototropin, phytochrome, chlamyopsin, volvoxopsin, and bacteriophytochrome. The entire bio-bot construct can be stimulated to move by illumination with defined spatiotemporal parameters, or illumination can be targeted to a specific portion of the bio-bot construct. Stimulation of bio-bots can occur upon illumination with visible light or ultraviolet light. In some embodiments, bio-bots fabricated with cells comprising ChR2 are illuminated with blue light (approximate wavelength of 450-495 nm).

Bio-bots can be also stimulated with a bipolar electrical pulse train. Electrical field pulses can be up to 50 volts per cm (e.g., about 50, 40, 30, 20, 10, 5, 3, 2, or less volts per cm) and of pulse widths of a few seconds or less (e.g. about 5, 4, 3, 2, 1, 0.5, 0.1, 0.01 seconds or less). Stimulation frequencies can be up to 10 Hz or frequencies up to when tetanus can result (e.g. about 20, 15, 10, 9, 8, 7, 6, 5, 4, 3, 2, 1 or less 10 Hz). Stimulation frequencies should be kept below the frequency that causes tetanus.

In some embodiments, an electric current is applied perpendicularly to the longitudinal axis of the bio-bot. The entire bio-bot can be stimulated to move by electric current, or the electric current can be targeted to a specific portion of the bio-bot. A localized electrical field can be applied to control the path of a symmetrical or asymmetrical bio-bot.

Bio-bots can be driven by a chemical energy source. In some embodiments, bio-bots convert glucose into mechanical energy. For bio-bots comprising neuronal and muscle cells, the genetic machinery of the neurons can be reprogrammed to regulate chemical secretions, which can be used to stimulate muscle cells to propel the bio-bot.

Bio-bots can be fabricated to move toward or away from a chemical gradient, chemoattractant, or chemorepellent. Bio-bots can be fabricated with one or more chemoreceptors for a specific chemoattractant or chemorepellent. Bio-bots can be fabricated with cells comprising specific chemoreceptors, or bio-bots can be fabricated with chemoreceptor protein preparations. Non-limiting examples of receptors for include G protein-coupled receptors (GPCRs) and histidine kinase-coupled receptors (HKCRs). For example, a bio-bot comprising a receptor for a specific toxin can be stimulated to move toward the toxin. The bio-bot can subsequently release one or more chemicals to neutralize the toxin. One of more type of cells present on or within the bio-bots can be used as "factories" to generate and secrete certain chemicals or proteins. It is possible to stimulate cells to release certain factors, both biological and non-natural or recombinant.

In one embodiment, the addition of isoproterenol (β-agonist) or carbamylcholine chloride (cholinergic agonist) can increase or decrease contraction frequency of layered tissue rings, respectively. Heptanol is a gap junction blocker that can reversibly stop synchronous contraction. Pulsatile electrical stimulation can also be used to induce and pace the muscle cells.

The disclosure provides methods of controlling the directional locomotion of the bio-bots comprising exposing the entire bio-bot or a selected portion of the bio-bot to light, an electrical pulse, or a chemical such as an excitatory neurotransmitter (e.g., glutamate). Glutamate can be used to control the frequency of contraction of the layered tissue ring.

The reaction of the cells in the bio-bot will control the directional locomotion of the bio-bot. Controlling directional locomotion of the bio-bot includes starting locomotion, stopping locomotion, slowing locomotion, accelerating locomotion, changing the direction of locomotion, or combinations thereof.

Drug Assays

The effect of a test agent on overall cell or tissue function may be missed by screening for effects on stationary cell culture. In one embodiment the bio-bots can be used to monitor the effect of drugs or test regents on the one or more cell types or the bio-bots themselves. A method is provided for detecting the response of the one or more types of cells or the bio-bot as a whole to one or more test agents comprising contacting a bio-bot with the one or more test agents and detecting or monitoring one or more of the following parameters: cell death, cell viability, number of cells, apoptosis, cell proliferation, contractile responses of the cells, angiogenesis, movement of the bio-bot, directional locomotion of the bio-bot. These parameters can be compared to known values for other test reagents (e.g. test regents that are known to affect the cells or bio-bots parameters) or to control assays (e.g., similar cells or bio-bots that are not treated with the test reagent).

Applications

Actuators and motors have fundamental roles to play in converting external sources of energy into controlled movement and power generation. To present compelling demonstrations of muscle-powered functionality in bio-integrated machines directional locomotion and 2D steering of millimeter-scale bio-bots were used as primary applications of this protocol. However, integrating muscle actuators into bio-hybrid machines can provide control over force generation and motility at multiple length scales[8], with broad applicability in a variety of fields. More immediate applications of this technology include fundamental studies of muscle development and disease, high-throughput drug testing, and dynamic functional implants. Bio-bots can integrate multiple cell and tissue types, including neuronal networks for sensing and processing and vascular networks for delivery of nutrients and other biochemical factors. Bio-bots can, for example, be designed to sense chemical toxins, locomote towards them, and neutralize them through cell-secreted factors. Such a functionality has broad relevance in medical diagnostics and targeted therapeutics in vivo, or even extended to environmental use as a method of cleaning up public water supplies from pathogens.

Comparisons to Other Methods

In vivo, skeletal muscle produces large contractile forces and its hierarchical and modular structure allows for ready scalability and adaptation to changing environmental loads[10]. Exercise training during differentiation can yield significant increases in force production. However, the forces produced by engineered skeletal muscle tissue have yet to demonstrate force production values on the order of magnitude observed in primary skeletal muscle[24]. As a result, some have investigated alternative approaches to building bio-hybrid machines by coupling excised skeletal muscle tissue to synthetic skeletons[25]. While these machines have demonstrated impressive functionality, due to the fact that primary cells typically produce larger forces than those produced by cell lines, primary cells are arguably a less sustainable source of material and their functional performance can vary widely depending on the age and health of the animal source[26]. As a result, the engineered skeletal muscle bio-bots described herein provide an opportunity for future growth in the field of tissue engineering.

Recent demonstrations of bio-hybrid machines powered by cardiac muscle have likewise met with significant success, with biomimetic designs and primary cells combining to produce complex locomotive behaviors[16:18:19]. However, in addition to the disadvantages of a platform that relies on primary cells, these demonstrations are also at a disadvantage due to the use of 2D sheets of cardiac muscle as actuators for bio-hybrid machines. The 3D hierarchical structure of skeletal muscle, which is mimicked in the layered tissue rings described herein, is critical to the modularity of design and scalability of force production that are required for a range of functional applications. Additionally, skeletal muscle is capable of "on-off" control, unlike cardiac muscle which spontaneously contracts, which will allow us to forward engineer higher-level control when such muscle bioactuators are couple to neural networks via neuromuscular junctions. Therefore, while the use of primary skeletal or cardiac cells is appealing at present, skeletal muscle bioactuators engineered from cell lines provide significant advantages over other methods.

The compositions and methodology presented in this disclosure has been optimized for generating millimeter- to centimeter-scale modular muscle bioactuators with active force generation capabilities up to 300 pN (approximately 0.5 kPa) when matured and stimulated in conditions suited to mammalian cells. Modifications of this protocol to produce bioactuators at different length scales, or 3D tissues made with different cell types are possible.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1. Experimental Design

Development of this protocol is dependent on the force generation and actuation requirements of a given application. This can be determined using an iterative process of designing and printing new bio-bot skeletons, predicting force production behavior via finite element analysis (FEA), and comparing predicted responses to actual responses observed when skeletons are coupled to engineered muscle in vitro. Bio-bots can be further customized to incorporate different cell types and different stimulation mechanisms, as befits the requirements of the application of concern. For example, we have applied this technique to C166 endothelial and NSC-34 neuron-like cell lines, both in the presence and absence of C2C12s, with no modifications to the protocol except exchanging the cell type and culture media used.

Forward engineering bio-hybrid machines involves designing and optimizing modular skeletal muscle bioactuators and 3D printed skeletons in parallel, before combining them to produce functional behaviors in response to external electrical or optical stimuli. This protocol outlines an approach that utilizes the externally stimulated contraction of skeletal muscle to drive directional locomotion of synthetic skeletons.

Example 2. Design and Optimization of Modular Skeletal Muscle Actuators

The injection molds that serve as templates for the muscle actuators are 3D printed with the biocompatible and bioinert poly (ethylene glycol) diacrylate (PEGDA) hydrogel polymer using a commercial stereolithographic apparatus (SLA) adapted to print mm-scale structures[27]. The ultraviolet laser of the SLA traces 2D cross-sections of 3D designs onto the polymer resin, rendered light-sensitive through the addition of a biocompatible photoinitiator (Irgacure 2959), building the part layer-by-layer from the bottom up. The shape and dimensions of the injection mold are prescribed by a computer-aided design (CAD) file, and can be readily modified to generate a variety of different muscle architectures. Fabricated mold dimensions will be larger than those prescribed by the CAD file, due to the swelling behavior of the highly absorbent and hydrophilic PEGDA polymer. The swelling ratio of the hydrogel is dictated by the molecular weight and concentration of monomer in the printable resin, with an average value of ~150% for the polymer composition used in this protocol[28,29]. While we chose to utilize a stereolithographic 3D printing approach, due to the versatility of this technique and ready availability of biocompatible photosensitive resins[1,2], this mold could also be manufactured using other biocompatible polymers and fabrication methodologies. For example, manufacturing hydrogel skeletons with feature sizes much smaller than 250 μm (the x-y resolution limit of our commercial SLA) will require using a printer capable of much higher resolution capabilities. We have custom-built a projection micro-stereolithographic 3D printer (μSLA) capable of printing hydrogel polymers at <5 μm resolution[3], which could be utilized to print smaller bio-bot skeletons, or skeletons with micro-scale features. Many fabrication methodologies and materials are suitable for manufacturing injection molds, as long as ease of sterilization and precise reproducibility of dimensions is maintained.

The cell/gel solution injected into the mold, composed of the C2C12 murine skeletal muscle cell line in a suspension of fibrinogen, thrombin, and Matrigel®, cross-links into a stable 3D gel network following the molding process. The final size of the muscle actuators is a function of cell density, cell distribution, hydrogel matrix composition, injection mold dimensions, and cell culture parameters. Higher concentrations of cells or fibrin in the solution, for example, lead to thinner muscle rings until a saturation point (1E7 cells $mL^{-1}$ and 4 mg $mL^{-1}$ fibrin respectively). Past this point, the finite volume occupied by the added material renders further thinning of muscle rings impossible. In general, cell/gel compositions and volumes that generate muscle ring actuators thicker than ~500 μm in diameter should be avoided, as this exceeds the diffusive distance of nutrients and biochemical factors from the surrounding media into the tissue[30] as well as the penetration depth of blue light (~500-740 μm) into tissue[31,32]. Each component of the cell/gel solution can thus be readily tuned and modified to suit the needs of a given application, as elaborated upon in the Experimental Design section of the protocol. However, all modifications to the cell/gel solution must be subjected to an optimization process that studies the effects of the solution parameter change on muscle ring architecture and functional performance.

The passive and active tension forces exerted by muscle actuators in response to external stimulation must be suited to the design and application of the mechanical skeletons to which they are tethered. The maximum force produced can be regulated by an exercise training regimen of controlled external stimulation of a specified frequency and duration, as well as by biochemical growth factors present in the media during muscle differentiation[23]. Others have demonstrated the performance enhancing effects of electrical stimulation[33] and dynamic mechanical stretch stimulation[34] on skeletal muscle during differentiation. We have shown that increases in muscle force production can likewise be driven by static mechanical cues[13] and dynamic optical stimulation[14] imposed during muscle maturation, with synergistic increases in force production demonstrated when mechanical and optical stimulation are combined. These increases in functional performance are attributed to greater degrees of cellular hypertrophy, as assessed by the ratio of total protein to DNA content in the engineered muscle tissue. Exercise protocols for muscle actuators that utilize regimens of biochemical, mechanical, optical, or electrical stimulation separately or in parallel can be precisely tuned and optimized to suit the force production needs of a bio-bot designed for a specific application.

Example 3. Design, Simulation, and Fabrication of Bio-Bot Skeletons

The design of the mechanical skeleton to which a modular muscle ring actuator is tethered is critical to the ability of the biological machine to perform the required output function. We have created several designs for producing directional locomotion and 2D steering in millimeter- to centimeter-scale structures via CAD (Supplementary Data) and optimized them using FEA software. Skeleton designs for applications beyond locomotion, such as pumping, can likewise be designed in CAD and tested prior to manufacture via FEA. We fabricated these CAD designs via the same SLA printing approach used to fabricate injection molds, but modified the polymer composition to enhance the stiffness of the skeletons. This change helped preserve mechanical integrity of skeletons during fabrication, muscle transfer and maturation, and bio-bot stimulation.

The process of mechanically coupling the elastic muscle ring actuators to the 3D printed bio-bot skeletons is critical to the modularity of this method of fabricating biological machines. Once optimal skeleton dimensions have been prescribed via CAD and FEA analysis, the injection mold must be redesigned to suit the shape and dimensions of the skeleton. Molds must be engineered to generate muscle ring actuators of the same shape as the site of tethering in the mechanical skeleton, and with inner diameters larger than the outer diameter of the mechanical skeleton, to maintain muscle structural integrity and ensure ease of transfer. Cultured muscle rings can then be manually transferred to printed skeletons prior to differentiation using sterile tweezers. Proliferation of cells within the rings will drive further compaction until limited by the mechanical constraint of the bio-bot skeleton, leading to secure coupling of the actuator to the skeleton. Rings can then be differentiated until maturation, defined by the point at which the muscle is capable of observable force production.

Example 4. Materials and Methods

3D Printing Injection Molds and Bio-Bot Skeletons 3-(Trimethoxysilyl)propyl methacrylate (3-TPM, Sigma Aldrich, 440159) 3-TPM is flammable. Consult the 3-TPM safety data sheet and use appropriate engineering controls, such as a chemical fume hood and proper personal protective equipment (PPE).

Ethanol, 200 proof (Decon Laboratories, Inc., 2716 or DSP-MD.43)

Poly (ethylene glycol) diacrylate (PEGDA) 700 g mol$^{-1}$ (Sigma Aldrich, 455008)

Poly (ethylene glycol) diacrylate (PEGDA) 1000 g mol$^{-1}$ (Polysciences Inc., 15178)

Sterile phosphate buffered saline (PBS, Lonza, 17-516F)

Irgacure 2959 (BASF, 55047962) We have shown that the concentration of Irgacure 2959 used as a photoinitiator in our PEGDA resins is biocompatible and renders the resin sensitive to the 325 nm ultraviolet light produced by our SLA[3,27]. Use of a different photoinitiator will need to be preceded by tests of biocompatibility and photosensitivity to the wavelength of light produced by the 3D printer in use.

Dimethyl sulfoxide (DMSO, Fisher Scientific, D128-500). Consult the DMSO safety data sheet and use appropriate engineering controls, such as a chemical fume hood and proper personal protective equipment (PPE).

Distilled Water

Cell Culture and Manufacture of Muscle Ring Bioactuators

C2C12 murine myoblasts (ATCC) infected with pLenti2-EF1α-ChR2[H134R]-tdTomato-WPRE plasmid to express mutant variant of the 470 nm blue light-sensitive ion channel, Channelrhodopsin (ChR2[H134R]).[14,36]

Cell lines should be regularly checked to ensure that they are authentic and not infected with *Mycoplasma*.

Dulbecco's Modified Eagle Medium with 4.5 g/L glucose, L-glutamine and sodium pyruvate (Corning, 10-013-cv)

Fetal Bovine Serum (FBS, Lonza, 14-502F)

Penicillin/Streptomycin (Cellgro Mediatech, 30-002-CI)

L-glutamine (Cellgro Mediatech, 25-005-CI)

Trypsin (TrypLE, ThermoFisher Scientific, 12605010)

Trypan Blue (ThermoFisher Scientific, 15250061)

Thrombin (Sigma Aldrich, T4648)

Fibrinogen (Sigma Aldrich, F8630)

Matrigel® (Corning, 354248)

Horse Serum, Heat Inactivated (Fisher Scientific, 26-050-070)

Aminocaproic acid (Sigma Aldrich, A2504)

LONG® R$^3$ Human Insulin-like Growth Factor-1 (IGF-1, Sigma Aldrich, I1271)

Bovine Serum Albumin (BSA, Sigma-Aldrich, A3059)

Quantification of Muscle Ring Viability

Cell Titer 96® AQueous One Solution MTS Cell Proliferation Assay (Promega, G3580)

Dulbecco's Modified Eagle Medium with 4.5 g/L glucose, no glutamine, no phenol red (ThermoFisher Scientific, 31053028)

Immunohistochemical Staining of Muscle Rings

Paraformaldehyde, EM grade, 16% (Electron Microscopy Sciences, 15710), Triton™ X-100 for molecular biology (Sigma-Aldrich, T8787), Image-iT® FX Signal Enhancer (ThermoFisher Scientific, 136933), MF 20 Antibody (Developmental Studies Hybridoma Bank at the University of Iowa), Anti-Sarcomeric Alpha-actinin antibody (Abcam, ab109776), Goat anti-Mouse IgG (H+L) Secondary Antibody, Alexa Fluor® 488 conjugate (ThermoFisher Scientific, A-11029), F(ab')2-Goat anti-Rabbit IgG (H+L) Secondary Antibody, Alexa Fluor® 568 conjugate (ThermoFisher Scientific, A-21069), 4', 6-Diamidino-2-Phenylindole, Dihydrochloride (DAPI, ThermoFisher Scientific, D1306), Agarose (Bio-Rad, 162-0100)

Histological Staining of Muscle Rings

Tissue-Tek® O.C.T. Compound (VWR, 25608-930), Hematoxylin Stain (ThermoFisher Scientific/Richard-Allan Scientific™, 7221), Eosin-Y Stain (Fisher Healthcare™, 22-220-104), Quantification of Total Protein and DNA Content of Muscle Rings DNeasy Blood and Tissue Kit (Qiagen, 69504) RIPA Lysis and Extraction Buffer (ThermoFisher Scientific, 89900), Pierce™ BCA Protein Assay Kit (ThermoFisher Scientific, 23227).

Equipment

3D Printing Injection Molds and Bio-Bot Skeletons 22 mm×22 mm glass coverslips (VWR, 48366067), Glass petri dishes (PYREX, Corning, 70165-152), Tweezers (VWR, 72927), Conical tubes, 15 mL and 50 mL (Denville Scientific Inc.), Centrifuge tubes, 1.5 mL (Fisher Scientific, 05-408-129), Syringe, 1 mL (BD, DGW87703-8036000), Needle, 26G×3/8 (BD, 305110), Serological pipette tips, 10, 200, 1000 µL (Denville Scientific Inc.), Vortexer (Fisher Scientific, 080131008), Chemical fume hood (Fisher Hamilton, SafeAire, 70864), Solvent waste container (Ecofunnel, 1-415-883-2600), Hot plate (Corning, PC-420D), Double sided tape (3M Scotch 34-8716-0599-3), 35 mm plastic petri dishes (Corning Inc., 351008), Stereolithographic 3D Printer (3D Systems, SLA 250/50), UV Laser safety goggles (Laservision)

Cell Culture and Manufacture of Muscle Ring Bioactuators

Serological pipette tips, 10, 200, 1000 µL (Denville Scientific Inc.), Serological pipettes, 5, 10, 25 mL (Fisher Scientific), Pipette aid (Eppendorf, Easypet 3), Micropipettes (Eppendorf, Research Plus), Culture flasks (Denville Scientific Inc.), Conical tubes, 15 mL and 50 mL (Denville Scientific Inc.), Centrifuge tubes, 1.5 mL (Fisher Scientific, 05-408-129), 35 mm plastic petri dishes (Corning Inc., 351008), Vortexer (Fisher Scientific, 080131008), Water bath (Fisher Scientific, Isotemp 210), Biosafety cabinet (Nuaire, NU-437-600), Mammalian culture incubator (Thermo Electron Corporation, Napco Series 8000 WJ CO2 incubator), Fridge (Thermo Electron Corporation, Revco), Freezer (VWR), Centrifuge (Eppendorf, 5810R), Hemacytometer (Fisher Scientific, 0267110), Upright microscope (Zeiss, Primovert), Tweezers (VWR, 72927)

Optical Stimulation of Muscle Contraction

Spatula (Fisher Scientific, 14375253), 470 nm LED (Luxeon), Alligator clip wires (DigiKey), Function generator (Agilent, 33250A)

Electrical stimulation of muscle contraction Spatula (Fisher Scientific, 14375253), Resistors, 1kΩ and 10 kΩ (DigiKey), Capacitor, 220 µF (DigiKey), Operational amplifier (DigiKey, OPA445AP), Alligator clip wires (DigiKey), Platinum electrodes, 0.762 mm diameter (Alfa Aesar, 14195) Breadboard (All Electronics Corporation, PB-3260) Function generator (Agilent, 33250A) Power supply (Agilent, E 3630A) Oscilloscope (Tektronix, TDS 3012)

Quantification of Muscle Ring Viability 24 well plate (Corning Costar® CLS3527) 96 well plate (Corning Costar® CLS3997) Microplate reader (BioTek, Synergy HT)

Histological Staining of Muscle Rings

Benchtop liquid nitrogen container (ThermoFisher Scientific, 2129) Cryostat (Leica, CM3050 S) Microscope slides, 3×1 (Fisher Scientific, 12550343)

Imaging of Muscle Rings

Glass bottom culture dish, 35 mm (MatTek, P35G-0-20-C) Stereomicroscope (LEICA MZFLIII) Confocal microscope (Zeiss, LSM 710) NanoZoomer 2.0-HT Digital slide scanner (Hamamatsu, C9600)

Quantification of Total Protein and DNA Content of Muscle Rings

Scissors (VWR, 82027588) Benchtop liquid nitrogen container (ThermoFisher Scientific, 2129) Digital Sonicator (Branson, 150) Micro Centrifuge (Eppendorf, 5415) Spectrophotometer (NanoDrop, 1000)

Software

SOLIDWORKS (Dassault Systemes): used to design parts for 3D printing. 3D Lightyear (3D Systems): used to slice 3D designs into sequential 2D layers in preparation for 3D printing. SPOT (SPOT Imaging): used for digital microscopy and imaging. ANSYS Workbench (ANSYS, Inc.): used to test and verify performance of bio-bot designs via finite element analysis. ImageJ (NIH): used to visualize and extract data from still images and videos of bio-bots.

Reagent Setup

3-TPM working solution: Using a syringe, add 400 µL of 3-TPM stock solution to 20 mL of 200 proof ethanol inside a chemical fume hood. This yields a final concentration of 2% (v/v) 3-TPM. Mix vigorously using a vortexer. This solution should be prepared fresh for each experiment.

Irgacure 2959 working solution: Add 1 mL of DMSO to 1 g of Irgacure 2959 powder. This yields a final concentration of 50% (w/v) Irgacure 2959. Mix vigorously using a vortexer. This solution should be prepared fresh for each experiment.

PEGDA 700 g mol$^{-1}$ working solution: Add 10 mL of PEGDA 700 g mol$^{-1}$ stock solution to 39.5 mL of PBS. Add 500 µL of Irgacure 2959 working solution and mix thoroughly. This yields a final concentration of 20% (v/v) PEGDA 700 g mol$^{-1}$ and 0.5% (w/v) Irgacure 2959. Allow bubbles to settle before use. This solution can be stored at room temperature (24° C.) for six months. Efforts should be made to ensure sterility of the solution (accomplished via filtration) during storage.

PEGDA 1000 g mol$^{-1}$ working solution: Add 10 g PEGDA 1000 g mol$^{-1}$ to 40.4 mL of PBS. Add 500 µL of Irgacure 2959 working solution and mix thoroughly. This yields a final concentration of 20% (v/v) PEGDA 1000 g mol$^{-1}$ and 0.5% (w/v) Irgacure 2959. Allow bubbles to settle before use. This solution can be stored at room temperature for six months. Efforts should be made to ensure sterility of the solution (accomplished via filtration) during storage.

70% ethanol sterilization solution: Mix 70 mL 200 proof ethanol with 30 mL distilled water, yielding a final concentration of 70% (v/v) ethanol. This solution can be stored at room temperature for one month.

Growth medium (GM): Supplement Dulbecco's Modified Eagle Medium containing 4.5 g/L glucose, L-glutamine and sodium pyruvate with 10% (v/v) Fetal Bovine Serum, 1% (v/v) Penicillin/Streptomycin, and 1% (v/v) L-glutamine to make GM. Medium should be stored in the fridge and warmed in a water bath at 37° C. before use.

Differentiation medium (DM): Mix Dulbecco's Modified Eagle Medium with 4.5 g/L glucose, L-glutamine and sodium pyruvate with 10% Horse Serum, 1% Penicillin/Streptomycin, and 1% L-glutamine to make DM. Medium should be stored in the fridge and warmed in a water bath at 37° C. before use.

Aminocaproic acid (ACA): Prepare a stock solution of 50 mg mL$^{-1}$ by dissolving ACA in distilled sterile water. This solution may be stored at 4° C. until use.

Insulin-like growth factor stock solution (IGF-1): Prepare a stock solution of 1 mg mL$^{-1}$ by dissolving IGF-1 in 10 mM HCl with 1 mg mL$^{-1}$ BSA as a carrier protein. This solution should be stored in aliquots at −20° C. until use.

Supplemented growth medium (GM+): Add 1 mL ACA to 49 mL GM solution to make GM+ containing 1 mg mL$^{-1}$ ACA. This solution may be stored at 4° C. before use.

Supplemented differentiation medium (DM++): Add 1 mL ACA and 2.5 µL IGF-1 to 49 mL DM solution to make DM++ containing 1 mg mL$^{-1}$ ACA and 50 ng mL$^{-1}$ IGF-1. This solution may be stored at 4° C. before use.

Thrombin stock solution: Dissolve thrombin lyophilized powder in a 0.1% (w/v) BSA solution to yield a final concentration of 100 units mL$^{-1}$ thrombin. This solution should be stored in aliquots at −20° C. until use.

Fibrinogen stock solution: Dissolve 8 mg fibrinogen in 1 mL of GM+ to make a solution of final concentration 8 mg mL$^{-1}$ fibrinogen. This solution should be made fresh for each experiment for best results.

MTS working solution: Make a 20% (v/v) solution of MTS by mixing 200 µL of CellTiter 96® AQueous One Solution Reagent with 1 mL of DMEM containing 4.5 g/L glucose, no glutamine, and no phenol red. This solution should be made fresh and stored in the dark until use.

Paraformaldehyde working solution: Mix 5 mL of 16% paraformaldehyde stock with 15 mL of PBS, yielding a final concentration of 4% (v/v). This solution can be made fresh or stored at −20° C. until use.

Triton X-100 working solution: Mix 50 µL of Triton X-100 with 25 mL of PBS, yielding a final concentration of 0.2% (v/v). This solution should be made fresh and stored at room temperature until use.

Primary and secondary antibody working solution: Add antibody to PBS or blocking solution in a ratio of 1:400 (0.25%). Store secondary antibodies in the dark before use.

DAPI working solution: Mix 10 µL DAPI with 25 mL distilled water. This solution can be made fresh or stored at −20° C. until use. Prepare in the dark.

Agarose stock solution: Make a 1% (w/v) solution by dissolving agarose powder in distilled water. The solution will solidify and may be stored at room temperature until use. Warm to liquefy agarose before use.

Equipment Setup

Cell Culture and Manufacture of Muscle Ring Bioactuators

Sterile tweezers: Immerse tweezers in solution of 70% ethanol for 5 min and allow to air dry completely before use.

Optical Stimulation of Muscle Contraction

Figure 7:
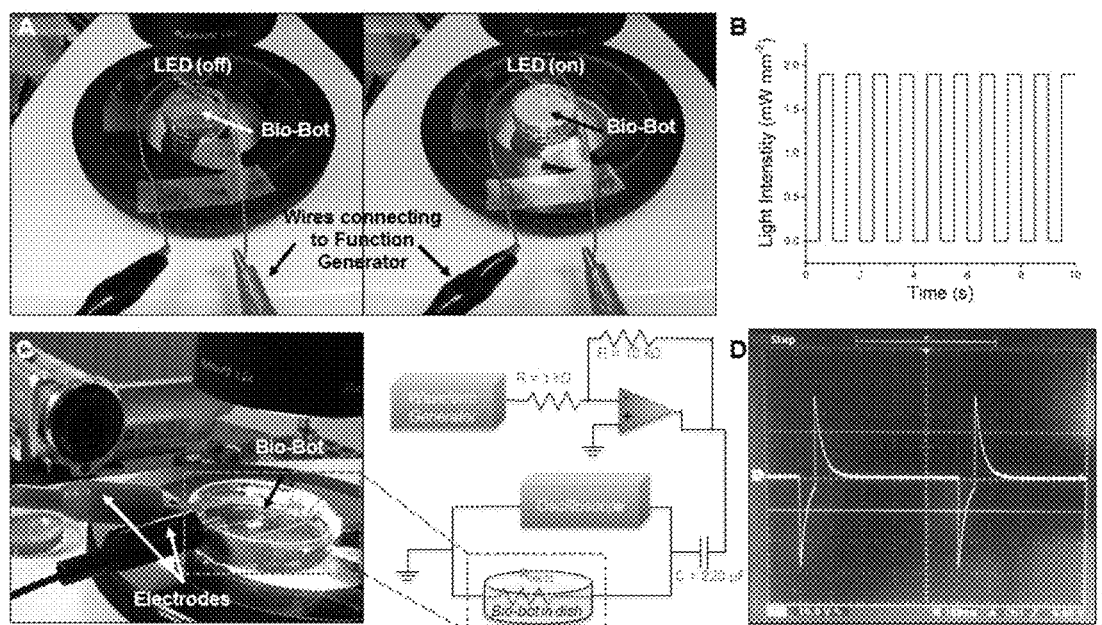
FIG. 7 panels A-D. External stimulation of muscle rings. (A) Stimulation setup for optical pulse stimulation of bio-bots. (B) Representative optical pulse train signal. (C) Stimulation setup for electrical pulse stimulation of bio-bots. (D) Representative electrical biphasic pulse signal.

Sterile spatula: Immerse tweezers in solution of 70% ethanol for 5 min and allow to air dry completely before use. Stimulation setup: Use alligator clip wires to connect the LED to the function generator's output signal as shown in FIG. 7A. Set the function generator output to a square-wave pulse signal of 20 V amplitude, 50 ms pulse width, and the desired frequency (1-4 Hz recommended). The output should resemble the signal shown in FIG. 7B.

Electrical Stimulation of Muscle Contraction

Figure 8:
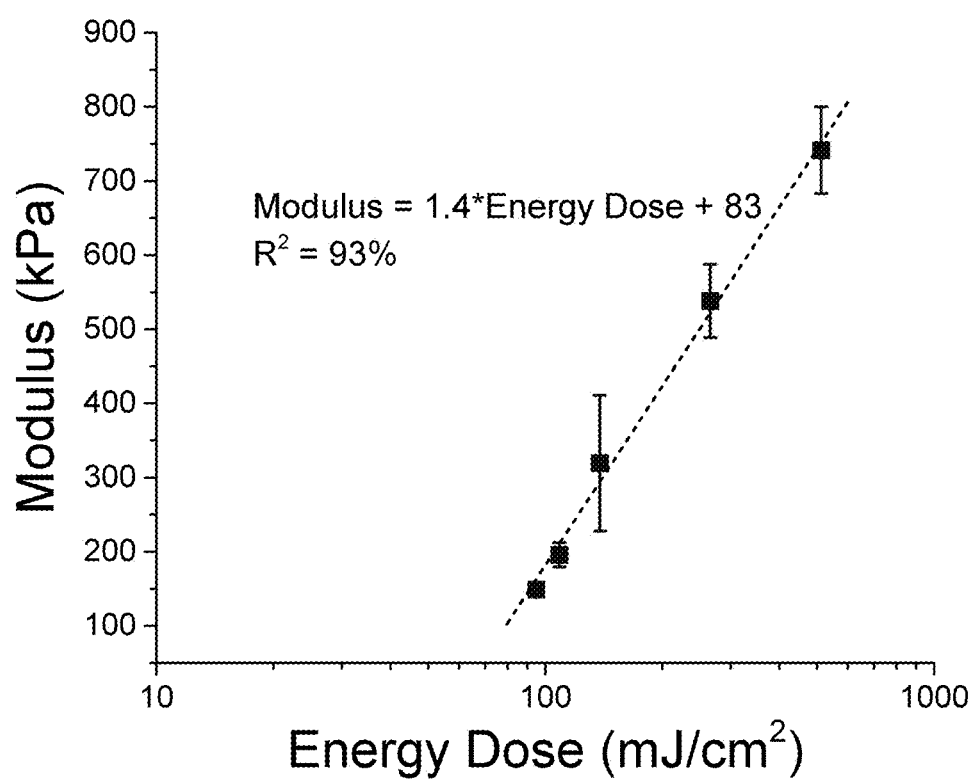
FIG. 8. Modulus as a function of Energy Dose. Plot of Young's Modulus for PEGDA 700 g mol$^{-1}$ as a function of the UV energy dose imposed by the laser of the SLA during fabrication.

Sterile spatula: Immerse tweezers in solution of 70% ethanol for 5 min and allow to air dry completely before use. Stimulation setup: Using the resistors, capacitor, and operational amplifier, build the circuit design shown in FIG. 7C on the breadboard. Clean the platinum electrodes by immersing in 70% ethanol for 2 min, then rinsing in PBS for 2 min. Set the function generator output to a square-wave pulse signal of 20 V amplitude, 50 ms pulse width, and the desired frequency (1-4 Hz recommended). The output should resemble the signal shown in FIG. 8D.

Procedure

CAD File Preparation for 3D Printing TIMING 1 h

1| Generate a 3D digital design of the muscle ring injection mold and bio-bot skeletons using CAD software (e.g. SOLIDWORKS) and save the design as an STL file. Exact dimensions used in our studies are presented below.

2| Slice the digital design into 2D printable layers (200 µm in our studies) using 3D Lightyear software (3D systems) so that it is readable by a stereolithographic 3D printer. Export the generated files to the computer operating the 3D printer.

Parts should be oriented in a manner that avoids the formation of dead volumes or overhangs, as these types of 3D structures are difficult to fabricate using stereolithographic printing.

The total thickness of the part should be divisible by the layer thickness specified in 3D Lightyear. This will allow the software to accurately calculate the number of layers to be printed.

The files can be prepared and loaded onto the computer operating the SLA at any time prior to fabrication.

3D Printing Injection Molds and Bio-Bot Skeletons TIMING 3 h

3| To functionalize glass coverslips with acrylate groups, pour 10 mL of 3-TPM working solution into large glass petri dish containing 8-10 22 mm square glass coverslips and incubate for 5 min.

3-TPM is flammable. Consult the 3-TPM safety data sheet and perform this step using appropriate engineering controls, such as a chemical fume hood and proper personal protective equipment (PPE).

4| Pour used 3-TPM working solution into a solvent waste container and add 10 mL of 100% ethanol to the petri dish containing the cover slips. Incubate for 5 min and then pour ethanol into solvent waste container.

5| Hard bake the slides in the petri dish on a hot plate at 110° C. until the coverslips are completely dry.

The coverslips should take no longer than 5 min to dry at this temperature. Over-baking the coverslips could result in poor stability of functionalized acrylate groups.

The methacrylated slides can be stored for up to 24 h at room temperature.

6| Using small pieces of double sided tape, attach the methacrylated glass coverslips to the center of 35 mm plastic petri dishes (one coverslip per dish) with the functionalized side facing up.

7| Add 1200 µL of pre-prepared polymer resin to each 35 mm petri dish, making sure the coverslip is immersed in resin. Use 20% w/v PEGDMA 1000 g mol$^{-1}$ for injection molds and 20% v/v PEGDA 700 g mol$^{-1}$ for bio-bot skeletons.

Troubleshooting

8| Place the petri dish on the build platform of the SLA and start building the part on the center of the glass coverslip using an energy dose setting of 138 mJ cm$^{-2}$. Add 250 µL of resin every time the program prompts you to recoat.

The laser should be turned on at least 30 minutes prior to the start of fabrication to ensure uniformity of light intensity.

Eyewear protecting against the wavelength of the laser in use should be worn while operating the SLA.

9| Once the part has been fabricated, gently release the glass coverslip from the petri dishes and wash the part in phosphate buffered saline (PBS).

10| Following the wash step, sterilize the parts by first immersing fabricated structures in a solution of 70% ethanol for 1 h, and then immersing in PBS for 1 h.

Fabricated parts can be stored in PBS at room temperature or 4° C. until ready for use. For best results, use parts within a week of fabrication.

Manufacturing Modular Muscle Ring Bioactuators TIMING 2 h

11| Place fabricated ring injection molds in a sterile 35 mm petri dish and carefully aspirate the PBS from the structure to prepare it for injection of the cell/gel solution.

Aspirate as much of the PBS from the molds as possible, without damaging the molds, to ensure that the concentration of reagents within the cell/gel solution are not diluted during the injection molding process.

12| Release cells from culture flasks using trypsin, count them, and aliquot them into vials containing 3E6 cells each (each aliquot corresponds to two muscle rings). Note: C2C12 murine skeletal muscle cells should be expanded in culture prior to experimental use, passaging 1:10 when cells reach 80% confluency.

Cells should not be allowed to reach 100% confluency and start differentiating in 2D culture prior to experimental use.

13| Centrifuge the aliquots at 200×g at room temperature for 5 minutes, aspirate remaining media, and resuspend each aliquot in 59.4 µL of GM+, which corresponds to a final concentration of 1E7 cells mL$^{-1}$ in the final cell/gel solution volume.

14| Add 0.6 µL of thrombin stock solution and 90 µL of Matrigel® to each aliquot of cells. Then add 150 µL of fibrinogen stock solution to each aliquot of cells and mix thoroughly. These correspond to final concentrations of 4 mg mL$^{-1}$ fibrinogen, 30% v/v Matrigel®, and 0.5 U mg-fibrinogen$^{-1}$ thrombin in the final cell/gel solution volume. Inject 120 µL of the completed cell/gel solution into each of the two wells of the injection molds.

Thrombin, Matrigel®, and fibrinogen stock solutions should be kept on ice during cell preparation process. Matrigel® stock solution, which is stored at −20° C., should be thawed overnight at 4° C. prior to experimental use to minimize solution viscosity and ensure ease of pipetting. Fibrinogen stock solution can be pre-prepared and stored at −20° C. prior to experimental use or prepared fresh for each experiment.

The cell/gel solution gels very quickly following the addition of fibrinogen. After centrifugation, prepare each aliquot individually and seed one injection mold (two muscle rings) at a time for best results.

Troubleshooting

15| Cover the petri dish and incubate the muscle rings for 1 h inside a mammalian cell culture incubator at 37° C. to allow the cell/gel solution to crosslink into a stable structure. Gently add 4 mL of warm GM+ following this incubation period and incubate for 24 h.

Coupling of muscle ring bioactuators to bio-bot skeletons TIMING 5 min

16| Following this 24 h incubation, transfer muscle rings to 3D printed bio-bot skeletons using sterile tweezers and refresh GM+. Change media daily.

The transfer procedure must be completed prior to the muscle differentiation process, to avoid damage to formed myotubes that may occur during transfer.

Troubleshooting

Maturation and Functional Optimization of Modular Muscle Rings TIMING 7 Days

17| Three days after seeding, change media to DM++ to begin the differentiation process. Refresh media daily. Muscle rings should demonstrate controlled twitch response to external electrical or optical stimulus within 7-10 days after seeding.

Troubleshooting

18| To maximize force production by providing both a static mechanical stretch stimulus and a dynamic optical pulse stimulus throughout differentiation, stimulate bio-bots using the exercise training regimen detailed in FIG. 10. The mechanical stretch stimulus is provided by keeping bio-bots tethered to the underlying glass slide from Day 1-12 of differentiation. The optical pulse stimulus is provided by daily stimulation (between Days 4-12) at 1, 2, and 4 Hz for 5 min each, with a 2 min rest period between each 5 min round. Optical stimulation (detailed in Step 19A) should be carried out at 37° C.

External Stimulation of Muscle Contraction

19| At this stage, muscle contraction can be triggered via either optical (Option A) or electrical (Option B) stimulation. The active tension force produced by the engineered muscle will be the same in both cases, but optical stimulation allows for a higher degree of spatiotemporal control over stimulation. That is, while the electrical stimulation protocol outlined here will stimulate the muscle actuator in its entirety, the optical stimulation protocol allows for isolated stimulation of specific muscle regions.

(A) Optical Stimulation of Muscle Contraction TIMING 5 Min (i) Using a sterile spatula, gently release the bio-bots from the underlying glass coverslips and place directly beneath a 470 nm LED. Connect the LED to a function generator to produce pulses of controlled frequency (1-10 Hz) and pulse width (50 ms) (FIG. 7A,B). Note that muscle rings should display tetanus behavior above 10 Hz.

Use fresh media at 37° C. to make sure glucose content has not been depleted.

Standard cell culture media is not optimal for long-term experiments at room temperature and atmosphere, as it requires $CO_2$ gas for pH buffering. While we have not observed significant changes in tissue viability or functionality over a relatively short stimulation period (5 min), longer stimulation regimens at room temperature and atmosphere will require modifying the composition of the culture media.

Troubleshooting (ii) Image using a microscope objective with a field of view large enough to capture at least one pillar of the bio-bot skeleton (FIG. 4C). Record videos at a frame rate suitable to the frequency of stimulation (10 frames per second in our studies) and return bio-bots to petri dishes containing fresh DM++ after stimulation.

(B) Electrical Stimulation of Muscle Contraction TIMING 5 Min (i) Using a sterile spatula, gently release the bio-bots from the underlying glass coverslips and transfer bio-bots to a sterile petri dish containing fresh plain DMEM without serum (to reduce the presence of bubbles, i.e. electrolysis, during electrical pulse stimulation).

Use fresh media at 37° C. to make sure glucose content has not been depleted and bio-bots are tested at conditions suited to mammalian cell culture.

Standard cell culture media is not optimal for long-term experiments at room temperature and atmosphere, as it requires $CO_2$ gas for pH buffering. While we have not observed significant changes in tissue viability or functionality over a relatively short stimulation period (5 min), longer stimulation regimens at room temperature and atmosphere will require modifying the composition of the culture media.

(ii) Align bio-bots parallel to the platinum electrodes of the electrical stimulation setup, making sure to avoid physical contact between the muscle actuators and the electrodes (FIG. 7C,D). Stimulate with pulses of controlled frequency (1-10 Hz) and pulse width (50 ms). Note that muscle rings should display tetanus behavior above 10 Hz.

(iii) Image using a microscope objective with a field of view large enough to capture the movement of at least one pillar of the bio-bot skeleton (FIG. 4C). Record videos at a frame rate suitable to the frequency of stimulation (at least 10 fps) and return bio-bots to petri dishes containing fresh DM++ after stimulation.

Calculation and FEA Verification of Passive Tension Force TIMING 30 Min

20| Take a side view image of a bio-bot and use ImageJ software (NIH) to measure the maximum deflection of the skeleton's beam and the distance between the muscle and the beam as depicted in FIG. 4A.

21| Use the equation presented below, derived from Euler-Bernoulli beam theory, to calculate the passive tension force produced by the muscle ring bioactuators:

$$F_p = \frac{8EI\delta_{max}}{lL^2}$$

Where $F_p$ is the passive tension force, E is the Young's Modulus of the PEGDA hydrogel skeleton (319.4 kPa for an SLA energy dose setting of 138 mJ cm$^{-2}$), I is the moment of inertia of the beam $$\left(\frac{1}{12}bh^3 = 2.8E-14\,m^4\right),$$

$\delta_{max}$ is me maximum deflection of the beam, l is the distance between the muscle and the beam, and L is the length of the beam (6 mm). Note that Young's Modulus of the hydrogel is dependent on the polymer composition and SLA energy dose. Values of E for varying energy doses are presented in FIG. 8.

22| To verify that the calculated force produced would generate the measured deflection of the beam, construct a static structural FEA model (using ANSYS software in this study) composed of half a bio-bot skeleton with the given geometric and material properties of 3D printed PEGDA. Impose a fixed support constraint at the middle of the beam and a passive tension force of the calculated magnitude on the skeleton and compare the computed deflection with the deflection measured empirically. Note that the model can also output other parameters, such as the equivalent stress in the skeleton after deformation (which shows regions of large stresses and stress concentrations), and this additional information can be used in optimizing the bio-bot skeleton geometry during an iterative design process. Specifically, skeleton dimensions can be changed in the computational model, and the resulting deformation can be predicted prior to empirical testing. This process is outlined in detail in Supplementary Method 1.

Calculation and FEA Verification of Active Tension Force TIMING 30 Min

23| With a manual tracking plugin in ImageJ[37], track the motion of a bio-bot (as shown in FIG. 4C) in a video acquired during externally stimulated contraction. A custom-written software for automated tracking of bio-bot movement during contraction, using normalized 2D cross-correlation of a user-specified feature in each frame, could prove useful for analysis of long videos.

24| Using this motion tracking data, calculate the average change in length of the bio-bot during each contraction and divide by the original length of the bio-bot to calculate strain. Knowing the acquisition frame rate of the video, calculate the strain rate. Input these values in the equation presented below, derived from a Kelvin-Voigt viscoelasticity model, to calculate active tension force:

$$\frac{F_a}{A} = E\varepsilon(t) + \eta\frac{d\varepsilon(t)}{dt} = E\frac{\Delta y}{y_0} + \eta\frac{\Delta\varepsilon}{\Delta t}$$

Where $F_a$ is the active tension force, A is the contact area between the muscle ring and the bio-bot skeleton, E is the Young's Modulus of the PEGDA hydrogel skeleton (319.4 kPa for an SLA energy dose setting of 138 mJ cm$^{-2}$), $\Delta y$ is the change in length of the skeleton during a contraction, $y_0$ is the original length of the skeleton in the passive state, $\eta$ is the viscosity of the PEGDA hydrogel (5.1 E-3 mPa s for the polymer composition used to build bio-bot skeletons), $\Delta\varepsilon$ is the change in calculated strain between two successive frames, and $\Delta t$ is the elapsed time between two successive frames.

The second term in the active tension equation is negligible at small strain rates but becomes significant at high strain rates, corresponding to stimulation frequencies above 4 Hz. Thus, while it is appropriate to treat the bio-bot as a linear elastic structure at low frequency stimulation, the addition of the viscosity term is required for high frequency stimulation.

25| To verify that the calculated force produced would generate the measured deflection and displacement of the bio-bot skeleton, construct a Static Structural FEA model (using ANSYS software in this study) coupled to a Rigid Dynamics model. Assign the bio-bot skeleton with the given geometric and material properties of 3D printed PEGDA, and impose a dynamic active tension force of the calculated magnitudes on the skeleton. Compare the computed displacement with the displacement measured empirically. Changing geometric or material properties of the bio-bot skeleton can be used to computationally predict the effects of changing these parameters prior to verification via empirical testing. This process is outlined in detail in Supplementary Method 2.

Assessment of Engineered Muscle Rings

26| At this stage, there are a number of options to analyze engineered muscle rings. Methods include quantification of muscle ring viability (Option A), immunohistochemical staining and imaging of muscle rings (Option B), histological staining and imaging of muscle rings (Option C), or quantification of total protein and DNA content of muscle rings (Option D).

(A) Quantification of Muscle Ring Viability TIMING 4 h (i) Immerse muscle rings individually in a 24-well plate in MTS working solution (500 μL per ring) for 4 h in the dark at 37° C. Also incubate 500 μL of the working solution in a separate well, without immersed muscle rings, as a negative control.

The reagent is sensitive to light and should be kept in the dark during preparation and incubation.

(ii) After the 4 h incubation, remove 100 μL of solution from each of the wells, including the negative control, and pipette each sample into a separate well of a 96 well plate.

The use of a multichannel pipette in steps 30A(i-ii) will assure identical volumes for each sample.

(iii) Read the absorbance of the media in each well at 490 nm excitation wavelength using a plate reader. First, compute the difference in absorbance of the solution obtained from sample wells as compared to the negative control. Comparing this normalized absorbance across different experimental groups will provide relative viability data for different muscle treatments, with larger absorbance values corresponding to increased viability.

(B) Immunohistochemical Staining and Imaging of Muscle Rings TIMING 2 d (i) Wash bio-bots in PBS and immerse in a solution of 4% formaldehyde dissolved in PBS for 30 minutes to fix the muscle tissue. Wash with PBS 3 times for 5 min each.

(ii) Immerse bio-bots in solution of 0.2% Triton X-100 in PBS for 15 min on a rotator or shaker at 4° C. to permeabilize the tissue. Wash with PBS 3 times for 5 min each.

(iii) Immerse bio-bots in Image-iT® FX Signal Enhancer blocking solution for at least 30 min.

Tissues immersed in blocking solution can be stored at 4° C. until ready for staining and imaging.

(iv) Immerse bio-bots in primary antibodies (MF-20, 1:400 dilution in blocking solution; Alpha-actinin, 1:400 dilution in blocking solution) overnight at 4° C. Wash with PBS 3 times for 5 min each.

(v) Immerse bio-bots in secondary antibodies (Goat anti-Mouse IgG (H+L) Secondary Antibody Alexa Fluor® 488 conjugate, 1:400 dilution in blocking solution; F(ab')2-Goat anti-Rabbit IgG (H+L) Secondary Antibody Alexa Fluor® 568 conjugate, 1:400 dilution in blocking solution) overnight in the dark at 4° C. Wash with PBS 3 times for 5 min each.

(vi) Immerse bio-bots in stock solution of DAPI (1:5000 dilution in DI water) for 10 min in the dark. Wash with PBS 3 times for 5 min each.

(vi) Add a small amount of liquid agarose to a glass-bottom petri dish, then immediately place a stained bio-bot onto the agarose and cover with more liquid agarose. Store in the dark at 4° C. until ready for imaging.

(vii) Image stained bio-bot muscle rings using a fluorescent microscope with excitation wavelengths specified by the fluorophores conjugated to the secondary antibodies.

Muscle Rings should be Imaged as Soon as Possible after Staining.

(C) Histological Staining and Imaging of Muscle Rings TIMING 2 d

Wash bio-bots in PBS and immerse in a solution of liquid nitrogen for 2 min to snap freeze the muscle tissue. Store the muscle tissues immediately at −80° C. to preserve protein content.

Handle liquid nitrogen with care and use proper PPE to avoid injury or asphyxiation. The use of an approved bench top dewar can facilitate the snap freezing process.

Frozen tissues can be stored at 80° C. until use.

Embed the muscle tissue in optimal cutting temperature (OCT) compound in the orientation desired and cut 10-15 μm sections with a temperature controlled cryostat.

Mount the tissue sections on glass slides and stain with hematoxylin and eosin (H&E) or other desired histological stains to detect cells and ECM proteins of interest.

Allow the slides to dry for 24 h and image with a digital pathology system (such as a Nanozoomer).

(D) Quantification of Total Protein and DNA Content of Muscle TIMING 4 h

If samples are to be analyzed at a later date, wash bio-bots in PBS and immerse in a solution of liquid nitrogen for 2 min to snap freeze the muscle tissue. Store the muscle tissues immediately at −80° C. to preserve protein content.

Handle liquid nitrogen with care and use proper PPE to avoid injury or asphyxiation. The use of an approved bench top dewar can facilitate the snap freezing process.

Frozen tissues can be stored at 80° C. until use.

If live tissues are to be analyzed immediately, wash bio-bots in PBS to remove excess media.

Use sterile scissors or forceps to gently cut the muscle tissue in half. Weigh each half using a balance scale and record the mass.

Place each half into a separate microcentrifuge tube in the appropriate lysis buffer and gently cut the tissues into small pieces. Vortex the sample for 10 s.

Use a DNeasy Blood and Tissue Kit (or equivalent) to isolate the genomic DNA from each muscle tissue half, according to the manufacturer's instructions. Measure the DNA concentration at 260 nm using a spectrophotometer and calculate the total content of DNA using the elution volume and the total mass of the muscle ring.

Use a BCA Protein Assay Kit (or equivalent) to determine the total protein content in each muscle tissue half, according to the manufacturer's instructions. First, add RIPA buffer to the tube to lyse the other half of each muscle tissue on ice for 30 min. Centrifuge the sample at 14,000×g at room temperature for 15 min and collect the supernatant.

Ensure that the tissue is completely lysed before continuing. Periodic vortexing during the lysing step may assist. If tissue pieces are still visible, sonicate the muscle tissues for 10 s.

(vii) Measure the absorbance of each sample at 562 nm using a spectrophotometer and compare to a standard curve of BSA protein absorbance vs. concentration to determine the protein concentration. Calculate the total protein content using the known supernatant volume and the total mass of the muscle tissue. This concentration may be normalized to the number of cells in the sample by dividing by the calculated total DNA content.

Timing

Steps 1-2, CAD file preparation for 3D printing: 1 h

Steps 3-10, 3D printing injection molds and bio-bot skeletons: 3 h

Steps 11-15, Manufacturing modular muscle ring bioactuators: 2 h

Step 16, Coupling of muscle ring bioactuators to bio-bot skeletons: 5 min

Steps 17-18, Maturation and functional optimization of modular muscle rings: 7 days Step 19A, Optical stimulation of muscle contraction: 5 min Steps 19B, Electrical stimulation of muscle contraction: 5 min Steps 20-22, Calculation of passive tension force: 30 min Steps 23-25, Calculation of active tension force: 30 min Step 26A, Quantification of muscle ring viability: 4 h Step 26B, Immunohistochemical staining and imaging of muscle rings: 2 d Step 26C, Histological staining and imaging of muscle rings: 2 d Step 26D, Quantification of total protein and DNA content of muscle rings: 4 h Troubleshooting Troubleshooting advice is listed in Table 1.

TABLE 1

Troubleshooting table

| Step | Problem | Possible Reason | Possible Solution |
|---|---|---|---|
| 7 | Layers of 3D printed parts are of inconsistent thicknesses | Resin solution surface is uneven during fabrication | Subject petri dish to oxygen plasma treatment to render inner surface of dish hydrophilic |
| 14 | Cell/gel solution volume contains several bubbles, resulting in inconsistent volumes pipetted into injection mold wells | This solution is viscous and bubbles can be introduced during quick pipetting and mixing | Make a larger volume of cell/gel solution than that required for two wells of an injection mold (The volumes provided in this protocol generate 25% extra cell/gel solution than required) |
| 16 | Muscle rings break during transfer from injection molds to skeleton | Muscle rings have limited elasticity and will rupture if over-stretched | Modify mold dimensions to manufacture muscle rings with larger inner diameters, rendering transferring to smaller skeletons easier |
| 17 | Muscle rings thin and rupture during culture | Myoblasts produce fibrinolytic compounds that break down the nature fibrin hydrogel matrix that compose the muscle ring | Increase the concentration of ACA, the anti-fibrinolytic compound already present in the culture medium to 2-3 mg mL$^{-1}$ |
| 19 | Muscle rings do not generate significant active tension forces in response to optical stimulation | The optical light stimulus is not penetrating the depth of the muscle tissue and exciting all the myotubes within | Increase light intensity and reduce muscle ring thickness until optical stimulation produces similar active tension forces as electrical stimulation |
| 19 | Muscle ring force production varies significantly from batch to batch | The concentration of Matrigel ® can vary from lot to lot, yielding different protein concentrations in each batch of muscle rings | Consult the certificates of analysis provided by the manufacturer for information regarding protein concentration in the lot used, and use the same lot across experiments to attain consistent results. In our experiments, the total protein concentration was 9.1 ± 0.4 mg/ml |

Results

Figure 6:
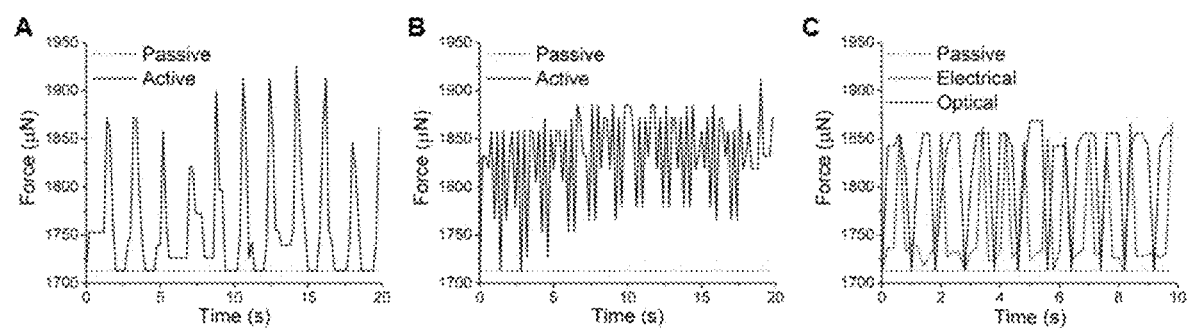
FIG. 6 panels A-C. Muscle ring force production. (A) Passive and active tension force produced by representative muscle ring in response to optical stimulation at 1 Hz. (B) Passive and active tension force produced by representative muscle ring in response to optical stimulation at 4 Hz. The passive tension baseline increases at higher frequency stimulation, as the muscle ring is not allowed to reach a fully relaxed state before the next pulse stimulus. (C) Comparison of active tension force produced by representative muscle ring in response to optical and electrical stimulation at 1 Hz, showing no significant difference between force produced using either method of external stimulation.

Using the formulations presented in this protocol, muscle rings are expected to contain elongated, aligned, and multinucleated myotubes with sarcomeric striations, visible by a range of immunohistochemical staining and imaging methods (FIG. 5). Functionally, muscle rings should produce passive tension forces on the order of 1710±230 µN (n=3). This corresponds to 3.2±0.4 kPa when divided by the average cross-sectional area of 0.54±0.06 mm$^2$ (n=3), as measured by confocal microscopy. Muscle rings are anticipated to produce active tension forces of 195±7.3, 114±8.1, and 110±16 µN (n=3) in response to optical stimulation at 1, 2, and 4 Hz respectively (FIG. 6A). These correspond to active tension stresses of 0.36±0.01, 0.21±0.02, and 0.20±0.03 kPa. Stimulation with electrical pulses should produce active tension forces similar to those produced by optical stimulation (FIG. 6B). The active tension strain produced by the muscle rings in response to stimulation at 1 Hz is on the order of 1%. Unconstrained muscle rings (uncoupled to bio-bot skeletons) can produce strains on the order of 3% for short periods of time, but myotubes within the muscle rings do not retain their alignment without the mechanical strain provided by the bio-bot skeleton.

An exercise training regimen combining a static mechanical stretch stimulus and a dynamic optical pulse stimulus during differentiation should produce significantly increased active tension forces on the order of 283±32 pN (0.52±0.06 kPa) ($P<0.05$, n=3, one-way ANOVA, post hoc Tukey test) in response to optical stimulation at 1 Hz. Exercised bio-bots are expected to produce directional locomotive speeds on the order of 312±63 µm s$^{-1}$ (n=6) and 2D rotation steering speeds on the order of 2.1±0.5° s$^{-1}$ (n=6). Locomotive speed is expected to increase in response to exercise training, with an average increase in speed of approximately 300% in response to a regimen combining static mechanical stretch and dynamic optical pulse stimuli. Locomotive speed is also expected to change in response to changing frequencies of stimulation, with an average increase in speed of approximately 80% when the stimulation frequency is increased from 1 to 4 Hz. On average, the useful life span of muscle ring actuators is on the order of 2-3 weeks.

Example 5 Supplementary Methods

Supplementary Method 1: Passive Tension FEA Analysis of Bio-Bot Skeletons

1| Open the Supplementary Data file titled "Passive Tension Template.wbpj" in ANSYS finite element analysis software. The default screen should display a Static Structural model on a page titled Project Schematic. The SOLIDWORKS file "Half Symmetric BioBot.SLDPRT" (corresponding to one half of a symmetric one-leg bio-bot skeleton) should already be loaded in the "Geometry" tab of the Static Structural model. If not, right click on "Geometry" and upload the CAD file "Half Symmetric BioBot.SLDPRT" included in the Supplementary Data.

2| Right click on the "Engineering Data" tab of the Static Structural model and click Edit to verify that the appropriate values for material properties of PEGDA 700 (Young's Modulus=3.194E+05 Pa, Poisson's Ratio=0.45) are listed. If these values do not appear, type in the correct values before closing the tab and returning to the main Project Schematic menu.

3| Right click on the "Model" tab of the Static Structural model and click Edit to open the Model page. Click on "Half Symmetric BioBot" under "Geometry" to verify that the Material Assignment is PEGDA 700. Click on "Fixed Support" under "Static Structural" to verify that the support is applied to the middle of the beam.

4| Right click on the "Static Structural" menu and click Insert→Force. Apply a static force of the calculated passive tension magnitude on the pillar of the bio-bot skeleton. Click the "Solve" button at the top of the menu on the Model page.

5| Verify that "Total Deformation" appears under "Solution" menu. If not, right click on "Solution" and click Insert→Deformation→Total. You can also choose to add other forms of solution, such as equivalent stress, to show regions or large stresses and stress concentrations. To do so, right click on "Solution" and click Insert→Stress→Equivalent (von Mises).

6| Click on "Total Deformation" under "Solution" to see the computed deflection of the model and compare it to the deflection measured empirically. If the computed deflection varies greatly from experimental values, re-visit your passive tension measurements and calculations.

7| Once computed deflections match those observed empirically, change geometric and material properties of the bio-bot skeleton in the FEA model to predict the effects of changing these parameters in an experiment.

Supplementary Method 2: Active Tension FEA Analysis of Bio-Bot Skeletons

1| Open the Supplementary Data file titled "Active Tension Template.wbpj" in ANSYS finite element analysis software. The default screen should display a Static Structural model coupled to a Rigid Dynamics model on a page titled Project Schematic. The SOLIDWORKS file "2LS.SLDPRT" (corresponding to a two-leg symmetric bio-bot skeleton) should already be loaded in the Geometry tab of the Static Structural model. If not, right click on Geometry and upload the CAD file "2LS.SLDPRT" included in the Supplementary Data.

2| Verify that the "Engineering Data", "Geometry", and "Model" tabs of the Static Structural and Rigid Dynamics model are linked. If not, select the three tabs and move the mouse to link them.

3| Right click on the "Engineering Data" tab of the Rigid Dynamics model and click Edit to verify that the appropriate values for material properties of PEGDA 700 (Young's Modulus=3.194E+05 Pa, Poisson's Ratio=0.45) are listed. If these values do not appear, type in the correct values before closing the tab and returning to the main Project Schematic menu.

4| Right click on the "Model" tab of the Rigid Dynamics model and click Edit to open the Model page. Click on "2LS" under "Geometry" to verify that the Material Assignment is PEGDA 700. Click on "Frictionless Support" and "Frictionless Support 2" under "Static Structural" to verify that the supports are applied to the bottom of the two ends of the bio-bot skeleton.

5| Right click on the "Static Structural" menu and click Insert→Force. Apply a time-varying force of the calculated active tension magnitude on the pillar of the bio-bot skeleton. Click the "Solve" button at the top of the menu on the Model page.

6| Verify that "Total Deformation" appears under "Solution" menu. If not, right click on "Solution" and click Insert→Deformation→Total. You can also choose to add other forms of solution, such as equivalent stress, to show regions or large stresses and stress concentrations. To do so, right click on "Solution" and click Insert→Stress→Equivalent (von Mises).

7| Click on "Total Deformation" under "Solution" to see the computed deflection of the model and compare it to the deflection measured empirically. If the computed deflection varies greatly from experimental values, re-visit your active tension measurements and calculations.

8| Once computed deflections match those observed empirically, change geometric and material properties of the bio-bot skeleton in the FEA model to predict the effects of changing these parameters in an experiment.

Supplementary Method 3: Image Processing for Analysis of Cellular Orientation and Morphology 1| Using the protocol outlined in step 26B from the main protocol, stain and image the muscle tissue, including a nuclear stain such as DAPI.

PAUSE POINT Images should be saved after staining and imaging.

2| Open the file containing the fluorescently-labeled nuclei in ImageJ and convert to 8-bit. By comparison to the original image, adjust the brightness and contrast to ensure that only (and all of) the nuclei are visible.

3| (A) Quantification of cellular alignment in muscle rings

Rotate the image 90° (Image→Transform→Rotate 90 Degrees Right).

Perform a Fast Fourier Transform on the binary image (Process 4 FFT 4 FFT).

Use the oval tool to draw a circle around the image.

CRITICAL STEP Ensure that the circle is centered on the image.

Compute the radial sum using the Oval Profile plug-in for ImageJ. Select "360" for number of points and "Radial Sums" for analysis mode. This will output a plot of summed intensity around the circle.

Click "List" to view the x-y values.

Repeat steps 3 (A)(i-v) above for each image. Alternatively, a fluorescently labeled image of myotubes may be used for FFT alignment analysis.

4| (A) Quantification of circularity of nuclei

Using the binary image from step 2 above, apply a threshold (Image→Adjust→Threshold) to highlight the nuclei.

Apply the Watershed algorithm to segment nuclei that are touching (Process→Binary→Watershed). If necessary, further separate touching particles by applying Erode or Open operations.

Analyze the selected nuclei (Analyze→Analyze Particles). If a range of sizes or circularity values is desired, input those parameters here. Select "Overlay Masks" to label the analyzed nuclei. Select "Exclude Egdes", "Include Holes," and "Display Results".

Inspect the resultant image to ensure that the particles were appropriately separated for analysis from step 4 (B)(ii).

Make sure that the "Shape descriptors" option is selected (Results→Set Measurements) to view circularity values.

Copy the results for further analysis.

Materials 3-(trimethoxysilyl)propyl methacrylate (3TPM), poly(ethylene glycol) diacrylate, retinoic acid, ciliary neurotrophic factor (CNTF), fibrinogen, thrombin from bovine plasma, aminocaproic acid (ACA), LONG® $R^3$ human insulin-like growth factor (IGF-1), Triton X-100, 4',6-diamindino-2-phenylindole (DAPI), and L-glutamic acid (glutamate) were obtained from Sigma-Aldrich (St. Louis, Mo., USA). Poly(ethylene glycol) dimethacrylate and hexamethyldisilazane (HMDS) were obtained from Polysciences, Inc. (Warrinton, Pa., USA). 1-[4-(2-hydroxyethoxy)phenyl]-2-hydroxy-2-methyl-1-propanone-1-one photoinitiator (Irgacure 2959) was obtained from BASF (Florham Park, N.J., USA). Dulbecco's Modified Eagle Medium (DMEM), penicillin-streptomycin (10,000 U $ml^{-1}$), and L-glutamine were obtained from Cellgro (Corning, Manassas, Va., USA). Fetal bovine serum (FBS) was obtained from VWR (Rednor, Pa., USA). Mouse embryonic fibroblasts (CF-1 mitomycin-C inactivated MEFs) were obtained from Applied Stem Cell, Inc. (Milpitas, Calif., USA). HBG3 mESCs (Hb9-GFP) were obtained from ArunA Biomedical (Athena, Ga., USA). EmbryoMax ES DMEM, EmbryoMax nucleosides, ESGRO mouse leukemia inhibitory factor (mLIF), and purmorphamine were obtained from EMD Millipore (Billerica, Mass., USA). Penicillin-streptomycin (5000 U $ml^{-1}$), MEM non-essential amino acids, β-mercaptoethanol, Advanced DMEM/F12, Neurobasal, KnockOut serum replacement, heat-inactivated horse serum, and collagen I-coated dishes were obtained from Gibco (LifeTechnologies, Carlsbad, Calif., USA). Glial-derived neurotrophic factor (GDNF) was obtained from Neuromics (Edina, Minn., USA). Matrigel™ basement membrane was obtained from Corning (Tewksbury, Mass., USA). Paraformaldehyde was obtained from Electron Microscopy Services (Hatfield, Pa., USA). Image-iT® FX Signal Enhancer and tetramethylrhodamine α-bungarotoxin (TRITC-conjugated α-BTX) were obtained from Molecular Probes (ThermoFisher, Waltham, Mass., USA). MF-20 anti-myosin heavy chain antibody was obtained from the Developmental Studies Hybridoma Bank (The University of Iowa, Iowa City, Iowa, USA). Anti-glial fibrillary acidic protein (GFAP) was obtained from Chemicon (EMD Millipore, Billerica, Mass., USA). Alexa Fluor® 488 goat anti-mouse IgG and Alexa Fluor® 568 F(ab')2 fragment of goat anti-mouse IgG were obtained from ThermoFisher (Waltham, Mass., USA). 35-mm glass-bottom dishes used for imaging were obtained from MatTek (Ashland, Mass., USA). (+)-tubocurarine chloride hydrochloride pentahydrate (curare) was obtained from Abcam (Cambridge, Mass., USA).

Fabrication of Hydrogel Ring Molds and Bio-Bot Skeletons

CAD software (AutoCAD) was used to design hydrogel ring molds and bio-bot skeletons[2]. Briefly, parts were exported in .stl format, sliced into layers using 3D Lightyear software (v1.4, 3D Systems), and fabricated using a modified Stereolithography apparatus (SLA 250/50, 3D Systems). 22×22 mm-square cover glass slides were treated in an oxygen plasma system to render the surface hydrophilic, chemically treated with 2% (v/v) 3-TPM, and adhered to a 35 mm culture dish, as detailed previously[2]. This treatment ensured chemical tethering of the fabricated hydrogel to the underlying glass slide. For hydrogel ring molds and bio-bot skeletons, liquid pre-polymer solutions were prepared as previously described[3]: 20% (w/v) poly(ethylene glycol) dimethacrylate of $M_W$ 1000 g $mol^{-1}$ (PEGDMA 1000) and 20% (v/v) poly(ethylene glycol) diacrylate of $M_W$ 700 g $mol^{-1}$ (PEGDA 700), respectively, dissolved in phosphate buffered saline (PBS) with 0.5% (w/v) Irgacure 2959. After fabrication, hydrogel parts were rinsed in PBS and then disinfected in 70% EtOH for at least 1 h. Sterilized parts were stored in sterile PBS at 4° C. until use.

Cell Culture

1. Skeletal Muscle. Proliferating C2C12s (murine myoblasts) were maintained in muscle growth medium consisting of DMEM with 10% (v/v) FBS, 1% (v/v) penicillin-streptomycin (10,000 U $ml^{-1}$), and 1% (v/v) L-glutamine. Cells in culture were passaged before confluence. All cells, cultures, and tissue rings were incubated at 37° C. and 5% $CO_2$.

2. Mouse Embryonic Stem Cells (mESCs). A feeder layer of mouse embryonic fibroblasts (CF-1 mitomycin-C inactivated MEFs) was pre-plated 2 d prior to stem cell culture at a density of $3\times10^4$ cells $cm^{-2}$ in DMEM with 10% (v/v) FBS, 1% (v/v) penicillin-streptomycin, and 1% (v/v) L-glutamine. HBG3 mESCs (Hb9-GFP) were thawed and expanded at a density of $5\times10^4$ cells $cm^{-2}$ on top of the MEF layer in mESC proliferation medium consisting of EmbryoMax ES DMEM with 15% (v/v) FBS, 1% (v/v) each of penicillin-streptomycin (5000 U $ml^{-1}$), L-glutamine, EmbryoMax nucleosides, and MEM non-essential amino acids, 0.1 mM β-mercaptoethanol, and 0.1% (v/v) mLIF. Cells were passaged before colonies reached confluence.

3. Embryoid Bodies (EBs) Containing Motor Neurons (MNs). As previously described (Wichterle H, Peljto M. Current Protocols in Stem Cell Biology. 2008, pp 1H.1.1-1H.1.9. and Uzel et al. Sci Adv 2016; 2: e1501429), to initiate differentiation, HBG3 mESCs were switched to neural differentiation medium containing 50% (v/v) Advanced DMEM/F12, 50% (v/v) Neurobasal, 10% (v/v) KnockOut serum replacement, 1% (v/v) penicillin-streptomycin (5000 U $ml^{-1}$), 1% (v/v) L-glutamine, and 0.1 mM β-mercaptoethanol. After 1 h of incubation in serum-free neural differentiation medium, cells were trypsinized, centrifuged, and replated at a density of $1\text{-}2.5\times10^6$ cells per 10 cm tissue culture dish (day 0). On day 1, floating cells in suspension were collected and replated in a new dish, and adhered cells were discarded. On day 2, floating EBs were collected and replated in differentiation medium with 1 µM purmorphamine and 1 µM retinoic acid. On day 5, floating EBs were collected and the medium was supplemented with 10 ng $ml^{-1}$ each of GDNF and CNTF (complete neural differentiation medium). Differentiated $GFP^+$ EBs were used between days 5-7.

Multi-Layered Tissue Ring Formation

For the formation of layer 1 of the multi-layered tissue rings, $5\times10^6$ cells $ml^{-1}$ (final density of C2C12s in the cell-gel solution) were combined with fibrinogen (4 mg $ml^{-1}$), thrombin (0.5 U $mg^{-1}$ fibrinogen), and Matrigel™ basement membrane (30% (v/v) of total cell-gel solution) on ice. Muscle growth medium was added to bring the cell-gel solution to its final volume (80 µl, $4\times10^5$ cells total per ring, unless otherwise noted), and the solution was added to the well of a hydrogel ring mold (day 0). Molds were previously aspirated of excess liquid to ensure consistent cell-gel densities. Tissue rings were allowed to incubate for 2 h before adding warm growth medium with 1 mg ml$^{-1}$ ACA, which was exchanged daily. On day 1, tissue rings were switched to muscle differentiation media consisting of DMEM with 10% (v/v) heat-inactivated horse serum, 1% (v/v) penicillin-streptomycin, 1% (v/v) L-glutamine, 1 mg ml$^{-1}$ ACA, and 50 ng ml$^{-1}$ IGF-1. On day 3, layer 2 was added to the hydrogel ring molds and allowed to compact around layer 1. Differentiated EBs were individually selected for being GFP$^{+}$ and mixed with the cell-gel solution. The cell-gel solution (60 µl, 3×10$^5$ cells total per ring) was otherwise identical to layer 1. Tissue rings were allowed to incubate for 2 h before adding warm complete neural differentiation medium with 1 mg ml$^{-1}$ ACA and 50 ng ml$^{-1}$ IGF-1.

Imaging

1. Immunocytochemistry. Samples were rinsed in PBS, fixed in 4% paraformaldehyde for 30 min, rinsed again, permeabilized with 0.25% Triton X-100 for 10 min, and blocked in Image-iT® FX overnight at 4° C. Samples were incubated with primary antibodies, MF-20 (1:400) or GFAP (1:1000), in Image-iT® FX at 4° C. overnight. After rinsing 3× with PBS, samples were incubated with secondary antibodies, either Alexa Fluor® 488 or Alexa Fluor® 568 goat anti-mouse (1:400), in Image-iT® FX in the dark at 4° C. overnight. After rinsing 3× with PBS, samples were incubated with DAPI (1:5,000 in sterilized de-ionized water) for 10 min, rinsed, and imaged in a 35-mm glass-bottom dish using a confocal microscope (LSM710, Zeiss). For imaging of acetylcholine receptors (AChRs), live samples were first incubated with TRITC-conjugated α-BTX (1:1000) in complete neural differentiation medium for one hour at 37° C., then fixed and imaged as detailed above.

2. Scanning Electron Microscopy (SEM). Samples were rinsed in PBS, fixed in 4% paraformaldehyde, and dehydrated using a series of ethanol solutions: 37% (10 min), 67% (10 min), 95% (10 min), and 100% (3×10 min). HMDS was added for 5 minutes, then allowed to vaporize. Gold/palladium was deposited on the dried sample for 70 s using a sputter coater (Desk II, TSC). Images were acquired using an environmental scanning electron microscope (XL30, Philips/FEI).

3. Area Measurements. A digital camera (Flex, SPOT Imaging Solutions) on a stereomicroscope (MZ FL III, Leica Microsystems) was used to take images of the multi-layered tissue rings during compaction. SPOT Software (v5.2, SPOT Imaging Solutions) and ImageJ software (National Institutes of Health) were used to measure tissue area dimensions over time.

4. Neurite Growth Measurements. After day 9 of differentiation, EBs were plated on either collagen I or Matrigel™ coated dishes in complete neural differentiation medium. EBs containing motor neurons expressed GFP+ and thus did not require additional cell markers. Live samples were imaged on days 10-14 using an inverted fluorescent microscope for 2D cultures (IX81, Olympus) or a confocal microscope for 3D tissue rings (LSM710, Zeiss). The NeuronJ plug-in (ImageScience) for ImageJ was used to measure neurite growth distances (FIG. 17).

Chemical Stimulation of Multi-Layered Tissue Rings

To stimulate motor neurons in tissue rings, glutamate was added to cell culture medium in a bath application of either 200 µM or 400 µM, as noted. Tissues were then transferred to fresh medium. After chemical stimulation, the nicotinic AChR antagonist curare was added to cell culture medium in a bath application of 25 µM. Tissues were then rinsed in PBS and transferred to fresh medium.

Video Capture and Movement Tracking

Muscle contraction within tissue rings was captured using a digital camera on a stereomicroscope with a capture rate of 5-10 frames s$^{-1}$. Image sequences were exported to .avi files. A custom Matlab script was used to calculate x-y displacement of user-specified regions of interest using normalized 2D cross-correlation, as described previously[3].

Statistical Analysis

All results are presented as mean±standard deviation. OriginPro software (v9.1) was used to calculate significance (one-way ANOVA followed by Tukey's Multiple Comparison Test).

Example 6. Differentiation of Embryoid Bodies Containing Motor Neurons

To attain motor neurons (MNs), we induced mouse embryonic stem cells (HBG3 mESCs, from a transgenic mouse cell line) to directly differentiate using a protocol that recapitulates spinal motor neuron maturation in embryonic development in vivo. Temporal addition of relevant growth and signaling factors pushed cells to become neural progenitor cells and then MNs. First, HBG3 mESCs were proliferated on a feeder layer of mouse embryonic fibroblasts (MEFs) to support their propagation, preserve pluripotent capacity, and prevent differentiation. When colonies became confluent (FIG. 22a), cells were switched to differentiation medium, trypsinized, centrifuged, and replated in a cell culture dish. MEFs adhered to the dish while HBG3 mESCs differentiated in suspension and aggregated to become spherical EBs (FIG. 11a). We added retinoic acid and purmorphamine (caudalizing and ventralizing signaling molecules that drive neural progenitors first toward spinal and then motor neuron identities, respectively) on day 2, and supplemented EB cultures with glial cell line-derived neurotrophic factor and ciliary neurotrophic factor (GDNF and CNTF, neural growth factors that promote MN survival[27]) on day 5. EBs increased in size and circularity over time, with the initial cell seeding density on day 0 playing a role in the size of differentiated EBs (FIG. 12b).

Cells expressed green fluorescent protein (GFP) under the control of the postmitotic motor neuron-specific Hb9 promoter (FIG. 19a); thus, we could visually confirm differentiation of MNs without the addition of exogenous factors or antibodies. Fluorescent imaging revealed that EBs also contained proliferating glia (FIG. 19), which are known to contribute to the formation and maintenance of the NMJ as well as differentiation and survival of MNs[11].

When allowed to adhere to natural ECM substrates such as collagen I13A and Matrigel™ (FIG. 13b and FIG. 19b), EBs containing MNs attached readily and extended neurites across the gels. Neurites grew 417.5±154.8 and 999.1+356.9 µm after 4 days of attachment (propagating at nearly linear rates of 88.6 and 264.8 µm day$^{-1}$) on collagen I and Matrigel™ surfaces, respectively (FIG. 13c). Similarly, EBs adhered to (and extended neurites across) the surface of 2D layers of differentiated C2C12s (FIG. 13d and FIG. 19c). After 5 days of co-culture, we identified clusters of postsynaptic acetylcholine receptors (visualized with fluorescently-conjugated α-BTX, which binds to a subunit of AChR) near the termination of neurite extensions on myotubes (FIG. 13e).

Example 7. Development of Multi-Layered Tissue Rings in Hydrogel Molds

To fabricate the macroscopic structures necessary for the development and co-culture of engineered tissue rings, we used a stereolithography apparatus to 3D print poly(ethylene) glycol-(PEG-)based hydrogels. We designed and 3D printed a hydrogel ring mold to guide the formation of a liquid cell-gel solution into a solid engineered muscle tissue. The mold contained rectangular-shaped wells that forced the compacting cells and ECM into a ring-shaped tissue (FIG. 14a and FIG. 20a). A cell-gel solution consisting of 80 µl of C2C12 myoblast precursor skeletal muscle cells and ECM proteins (Matrigel™ and fibrinogen) was injected into the mold. The polymerization of the matrix proteins (thrombin was added to cleave fibrinogen and form a cross-linked fibrin network) as well as the traction forces exerted by the myoblasts on surrounding proteins resulted in compaction of the tissue into a solid ring (FIG. 14b (i)). After 1 day, we added differentiation medium containing 10% horse serum in order to induce fusion of myoblasts into mature muscle fibers, or myotubes (FIG. 18b). Medium was also supplemented with aminocaproic acid (ACA, an inhibitor to prevent degradation of the ECM by cell-secreted proteases) and insulin-like growth factor (IGF-1, which is known to increase myoblast fusion and muscle hypertrophy).

After 3 days of allowing the first muscle layer to compact and differentiate in the hydrogel ring mold, we added a second layer of cell-gel solution (FIG. 14b(ii)). This mixture contained the same C2C12 and ECM components as the first layer, as well as differentiated EBs that were individually selected for being predominantly GFP$^+$ (thus containing MNs). Co-culture medium was switched to complete neural differentiation medium supplemented with ACA and IGF-1.

Layer 2 compacted around the first and the cross-sectional tissue area decreased daily to a lower limit of 17.9±1.6 mm$^2$, or approximately 22% of the original area dictated by the hydrogel ring mold, after 5 days of co-culture (FIG. 14c). We controlled the thickness of the tissue by varying the initial cell-gel volume; initial volumes of 60, 80, and 90 µl (containing 3×10$^5$, 4×10$^5$, and 4.5×10$^5$ cells in each ring) resulted in ring tissues with layer 1 cross-sectional areas of 11.7±1.6, 13.9±2.4, and 17.1±4.6 mm$^2$ (14.3, 17.1, and 21.0% of the original area) after 5 days, respectively (FIG. 21).

Various imaging modalities confirmed the presence of both differentiated muscle as well as GFP$^+$ EBs in the multi-layered tissue rings. Compaction of layer 2 brought the EBs in close contact with layer 1 during the first 24 h of co-culture (FIG. 14d). By this time, the myoblasts in layer 1 had differentiated to form elongated, multinucleated myotubes that expressed mature myosin protein (FIG. 14e).

Example 8 Spontaneous Muscle Contraction in Co-Culture

Following the addition of layer 2 with MN-containing EBs to the hydrogel ring molds (FIG. 15a-i), we observed spontaneous contraction of differentiated muscle in layer 1 as early as 2 h after co-culture. Two regions of muscle in layer 1, approximately 600 and 800 µm from the nearest group of EBs, twitched at approximately 1.6 contractions sec$^{-1}$, with local displacements measuring 9.9±1.8 and 6.8±1.9 µm per twitch for regions 1 and 2, respectively (FIG. 15a-ii). After 24 h of co-culture, after layer 2 had begun to compact into a solid ring (FIG. 15b-i), we observed continued spontaneous contraction. The muscle twitched with decreased frequency (approximately 0.9 contractions sec$^{-1}$) and amplitude (6.5±0.9 and 8.7±1.6 µm per twitch) compared to hour 2 (FIG. 15b-ii), and spontaneous contraction eventually ceased.

Example 9 Transfer of Multi-Layered Tissue Rings to Hydrogel Skeletons

When both layers fused into one tissue, the compliant ring was physically placed onto a 3D printed structure (FIG. 16a). We designed and fabricated a stationary skeleton, composed of a beam connecting two stiff pillars, representing a physiological muscle-tendon-bone arrangement (FIG. 20b). The beam of the skeleton was chemically tethered to a glass slide and thus provided a static mechanical stretch to the tissue rings.

Within the multi-layered tissue rings, EBs began to extend neurites from GFP$^+$ MNs. Using confocal imaging, we confirmed that the extension propagated in 3D throughout the tissue, both in the direction of other EBs as well as toward differentiated muscle (FIG. 16b). Neurite length significantly increased between days 3 and 9 of co-culture, from 207.4±153.2 to 433.6±372.5 µm (FIG. 16c).

Chemical Stimulation of MNs in Multi-Layered Tissue Rings

On day 9 after co-culture, we chemically stimulated MNs by adding glutamate. Multi-layered tissue rings were first subjected to a bath application of 200 µM glutamate in complete neural differentiation medium. Through video recordings, we observed that local muscle contraction began in response to chemical stimulation of MNs (FIG. 16d). When we increased the glutamate concentration from 200 to 400 µM, the frequency of muscle twitching increased from 1.08 to 1.33 contractions sec$^{-1}$, while the average displacement decreased from 6.3±0 to 4.4±0.2 µm per twitch (FIG. 16e). The addition of 25 µM tubocurarine chloride (curare), an irreversible nicotinic NMJ antagonist and muscle relaxant that blocks AChRs, halted the contractions; no further muscle twitching was observed.

REFERENCES

1. Melchels, F. P. W., Feijen, J. & Grijpma, D. W. A review on stereolithography and its applications in biomedical engineering. *Biomaterials* 31, 6121-30 (2010).
2. Raman, R. & Bashir, R. in *Essentials of 3D Biofabrication and Translation* 89-121 (2015).
3. Raman, R. et al. High-Resolution Projection Microstereolithography for Patterning of Neovasculature. *Adv. Healthc. Mater.* 1-10 (2015). doi:10.1002/adhm.201500721
4. Sears, N. A. A Review of 3D Printing in Tissue Engineering. *Tissue Eng. Part B Rev.* 1-39 (2016).
5. Peltola, S. M., Grijpma, D. W., Melchels, F. P. W. & Kellomaki, M. A review of rapid prototyping techniques for tissue engineering purposes. *Ann. Med.* 40, 268-280 (2008).
6. Bajaj, P., Schweller, R. M., Khademhosseini, A., West, J. L. & Bashir, R. 3D Biofabrication Strategies for Tissue Engineering and Regenerative Medicine. *Annu. Rev. Biomed. Eng.* 16, 247-276 (2013).
7. Kamm, R. D. & Bashir, R. Creating Living Cellular Machines. *Ann. Biomed. Eng.* 42, 445-459 (2014).
8. Feinberg, A. W. Biological Soft Robotics. *Annu. Rev. Biomed. Eng.* 17, 243-65 (2015).
9. Chan, V., Asada, H. H. & Bashir, R. Utilization and control of bioactuators across multiple length scales. *Lab Chip* 14, 653-670 (2014).
10. Sambasivan, R. & Tajbakhsh, S. Vertebrate Myogenesis. 56, 191-213 (2015).
11. Duffy, R. M. & Feinberg, A. W. Engineered skeletal muscle tissue for soft robotics: fabrication strategies, current applications, and future challenges. *Wiley Interdiscip. Rev. Nanomed. Nanobiotechnol.* 6, 178-195 (2014).
12. Bian, W., Liau, B., Badie, N. & Bursac, N. Mesoscopic hydrogel molding to control the 3D geometry of bioartificial muscle tissues. *Nat. Protoc.* 4, 1522-34 (2009).
13. Cvetkovic, C. et al. Three-dimensionally printed biological machines powered by skeletal muscle. *Proc. Natl. Acad. Sci. U.S.A* 111, 10125-30 (2014).
14. Raman, R. et al. Optogenetic skeletal muscle-powered adaptive biological machines. *Proc. Natl. Acad. Sci.* (2016). doi:10.1073/pnas.1516139113
15. Feinberg, A. W. et al. Muscular thin films for building actuators and powering devices. *Science* (80-.). 317, 1366-70 (2007).
16. Nawroth, J. C. et al. A tissue-engineered jellyfish with biomimetic propulsion. *Nat. Biotechnol.* 30, 792-7 (2012).
17. Chan, V. et al. Multi-material bio-fabrication of hydrogel cantilevers and actuators with stereolithography. *Lab Chip* 12, 88-98 (2012).
18. Chan, V. et al. Development of miniaturized walking biological machines. *Sci. Rep.* 2, 857 (2012).
19. Park, S.-J. et al. Phototactic guidance of a tissue-engineered soft-robotic ray. *Science* (80-.). 353, 158-162 (2016).
20. Bian, W. & Bursac, N. Engineered skeletal muscle tissue networks with controllable architecture. *Biomaterials* 30, 1401-12 (2009).
21. Hinds, S., Bian, W., Dennis, R. G. & Bursac, N. The role of extracellular matrix composition in structure and function of bioengineered skeletal muscle. *Biomaterials* 32, 3575-83 (2011).
22. Sakar, M. S. et al. Formation and optogenetic control of engineered 3D skeletal muscle bioactuators. *Lab Chip* 12, 4976-85 (2012).
23. Rangarajan, S., Madden, L. & Bursac, N. Use of Flow, Electrical, and Mechanical Stimulation to Promote Engineering of Striated Muscles. *Ann. Biomed. Eng.* 42, 1391-1405 (2014).
24. Dennis, R. G., Kosnik, P. E., Gilbert, M. E. & Faulkner, J. a. Excitability and contractility of skeletal muscle engineered from primary cultures and cell lines. *Am. J. Physiol. Cell Physiol.* 280, C288-C295 (2001).
25. Herr, H. & Dennis, R. G. A swimming robot actuated by living muscle tissue. *J. Neuroeng. Rehabil.* 1, 6 (2004).
26. Kaur, G. & Dufour, J. M. Cell lines: Valuable tools or useless artifacts. *Spermatogenesis* 2, 1-5 (2012).
27. Chan, V., Zorlutuna, P., Jeong, J. H., Kong, H. & Bashir, R. Three-dimensional photopatterning of hydrogels using stereolithography for long-term cell encapsulation. *Lab Chip* 10, 2062-70 (2010).
28. Neiman, J. A. S. et al. Photopatterning of hydrogel scaffolds coupled to filter materials using stereolithography for perfused 3D culture of hepatocytes. *Biotechnol. Bioeng.* 112, 777-787 (2015).
29. Raman, R. et al. 3D printing enables separation of orthogonal functions within a hydrogel particle. *Biomed. Microdevices* 18, 49 (2016).
30. Novosel, E. C., Kleinhans, C. & Kluger, P. J. Vascularization is the key challenge in tissue engineering. *Adv. Drug Deliv. Rev.* 63, 300-11 (2011).
31. Barolet, D. Light-Emitting Diodes (LEDs) in Dermatology. *Semin. Cutan. Med. Surg.* 27, 227-238 (2008).
32. Moreira, M. C., Prado, R. & Campos, A. in *Applied Biomedical Engineering* 3-20 (2011).
33. Donnelly, K. et al. A novel bioreactor for stimulating skeletal muscle in vitro. *Tissue Eng. Part C. Methods* 16, 711-718 (2010).
34. Powell, C. a, Smiley, B. L., Mills, J. & Vandenburgh, H. H. Mechanical stimulation improves tissue-engineered human skeletal muscle. *Am. J. Physiol. Cell Physiol.* 283, C1557-65 (2002).
35. Duan, C., Ren, H. & Gao, S. Insulin-like growth factors (IGFs), IGF receptors, and IGF-binding proteins: roles in skeletal muscle growth and differentiation. *Gen. Comp. Endocrinol.* 167, 344-51 (2010).
36. Uzel, S. G. M. et al. Microfluidic platform for the formation of optically excitable, three-dimensional, compartmentalized motor units. *Sci. Adv.* (2015).
37. Cordeli, F. Manual Tracking. *NIH* 1-3 (2005).

What is claimed is:

1. A biological machine comprising:
    a skeleton comprising two or more hydrogel pillars having top and bottom base end surfaces, wherein the two or more hydrogel pillars are coupled to one or more hydrogel beams at their top base end surfaces, wherein the hydrogel beam extends between the two or more hydrogel pillars; and
    at least one layered tissue ring comprising a first ring shaped layer comprising differentiated myoblasts in a gel; and a second ring shaped layer comprising motor neurons;
wherein the first and second layers are fused into a layered tissue ring;
    wherein the layered tissue ring surrounds the two or more pillars.

2. The biological machine of claim 1, wherein the two or more hydrogel pillars have caps on their bottom base end surfaces.

3. The biological machine of claim 1, wherein the differentiated myoblasts are elongated, contractile myotubes.

4. The biological machine of claim 1, wherein the biological machine has active force generation of about 150, 200, or 300 µN or about 0.3, 0.4, or 0.5 kPa.

5. The biological machine of claim 1, wherein the one or more layered tissue rings have motor neuron induced muscle contraction.

6. The biological machine of claim 1, wherein the layered tissue ring contracts in response to electrical stimulation, chemical stimulation, optical stimulation, or combinations thereof.

7. The biological machine of claim 1, wherein the motor neurons are responsive to at least one excitatory neurotransmitter.

8. The biological machine of claim 7, wherein the at least one excitatory neurotransmitter is glutamate.

9. The biological machine of claim 1, wherein the layered tissue ring comprises neuromuscular junctions.

10. The biological machine of claim 1, wherein one or more of the cells of the layered tissue ring express one or more heterologous light-sensitive proteins.

11. The biological machine of claim 1, wherein the biological machine is capable of locomotion.

12. A method of making the biological machine of claim 1, comprising:
    (a) making the two or more hydrogel pillars coupled to one or more hydrogel beams with a stereo-lithographic apparatus or a molding apparatus and polymerizable liquid materials;
    (b) making a layered tissue ring; and
    (c) surrounding the two or more pillars with the layered tissue ring.

13. A method of inducing the biological machine of claim 1 to locomote comprising contacting a portion of the layered tissue ring or the entire layered tissue ring with light, electrical pulses, or a chemical capable of inducing contraction of the layered tissue ring such that the biological machine locomotes.

14. The biological machine of claim 1, wherein the motor neurons of the second ring shaped layer are present in a gel.

15. The biological machine of claim 1, wherein the layered tissue ring is 500 to 750 μM thick.

* * * * *